(12) United States Patent
Jung et al.

(10) Patent No.: US 10,072,276 B2
(45) Date of Patent: Sep. 11, 2018

(54) GENETICALLY ENGINEERED YEAST CELL HAVING INCREASED NADPH PRODUCTION, METHOD OF INCREASING NADPH LEVEL IN YEAST CELL, METHOD OF PREPARING YEAST CELL, AND METHOD OF PRODUCING LACTATE USING YEAST CELL

(71) Applicant: SAMSUNG ELECTRONICS CO., LTD., Suwon-si, Gyeonggi-do (KR)

(72) Inventors: Yukyung Jung, Hwaseong-si (KR); Kwangmyung Cho, Seongnam-si (KR); Jinha Kim, Namyangju-si (KR); Soonchun Chung, Seoul (KR)

(73) Assignee: SAMSUNG ELECTRONICS CO., LTD., Suwon-ki (KR)

( * ) Notice: Subject to any disclaimer, the term of this patent is extended or adjusted under 35 U.S.C. 154(b) by 42 days.

(21) Appl. No.: 15/066,775

(22) Filed: Mar. 10, 2016

(65) Prior Publication Data

US 2016/0340698 A1 Nov. 24, 2016

(30) Foreign Application Priority Data

May 18, 2015 (KR) .................. 10-2015-0069117

(51) Int. Cl.
| | | |
|---|---|---|
| *C12N 15/52* | (2006.01) | |
| *C12P 7/56* | (2006.01) | |
| *C12N 9/12* | (2006.01) | |
| *C12N 9/02* | (2006.01) | |
| *C12N 9/04* | (2006.01) | |

(52) U.S. Cl.
CPC .............. *C12P 7/56* (2013.01); *C12N 9/0006* (2013.01); *C12N 9/0008* (2013.01); *C12N 9/0036* (2013.01); *C12N 9/1205* (2013.01); *C12N 15/52* (2013.01); *C12Y 101/01001* (2013.01); *C12Y 101/01027* (2013.01); *C12Y 101/01049* (2013.01); *C12Y 102/0101* (2013.01); *C12Y 102/01012* (2013.01); *C12Y 106/01001* (2013.01); *C12Y 207/01023* (2013.01); *C12Y 207/01086* (2013.01)

(58) Field of Classification Search
CPC ................ C12Y 101/01049; C12Y 101/01027
See application file for complete search history.

(56) References Cited

U.S. PATENT DOCUMENTS

| | | |
|---|---|---|
| 2003/0017557 A1 | 1/2003 | Hanke |
| 2008/0305533 A1 | 12/2008 | Yi et al. |
| 2010/0009418 A1 | 1/2010 | San et al. |
| 2012/0164703 A1 | 6/2012 | Yi et al. |
| 2016/0333380 A1 | 11/2016 | Chung et al. |

FOREIGN PATENT DOCUMENTS

| | | |
|---|---|---|
| KR | 2002-0048928 | 6/2002 |
| KR | 2007-0108155 | 11/2007 |
| KR | 10-2016-0133308 A | 11/2016 |
| WO | WO 00/03021 A2 | 1/2000 |

OTHER PUBLICATIONS

Gorsich et al. 2006; Tolerance to furfural-induced stress is associated with pentose phosphate pathway genes ZFW1, GND1, RPE1, and TKL1 in *Saccharomyces cerevisiae*. Appl Microbiol Biotechnol. 71: 339-349.*

Angermayr et al., Engineering a Cyanobacterial Cell Factory for Production of Lactic Acid, *Applied and Environmental Biology*, 78(19): 7098-7106 (2012).

* cited by examiner

*Primary Examiner* — Karen Cochrane Carlson
(74) *Attorney, Agent, or Firm* — Leydig, Voit & Mayer, Ltd.

(57) ABSTRACT

Provided is a genetically engineered yeast cell having increased NADPH production, a method of increasing a NADPH level in a yeast cell, a method of preparing the genetically engineered yeast cell, and a method of producing lactate using the genetically engineered yeast cell.

8 Claims, 2 Drawing Sheets
Specification includes a Sequence Listing.

SEQUENCE LISTING

<160> NUMBER OF SEQ ID NOS: 149

<210> SEQ ID NO 1
<211> LENGTH: 946
<212> TYPE: PRT
<213> ORGANISM: Saccharomyces cerevisiae

<400> SEQUENCE: 1

Met Ala Gly Gln Val Leu Asp Gly Lys Ala Cys Ala Gln Gln Phe Arg
1               5                   10                  15

Ser Asn Ile Ala Asn Glu Ile Lys Ser Ile Gln Gly His Val Pro Gly
            20                  25                  30

Phe Ala Pro Asn Leu Ala Ile Ile Gln Val Gly Asn Arg Pro Asp Ser
        35                  40                  45

Ala Thr Tyr Val Arg Met Lys Arg Lys Ala Ala Glu Glu Ala Gly Ile
    50                  55                  60

Val Ala Asn Phe Ile His Leu Asp Glu Ser Ala Thr Glu Phe Glu Val
65                  70                  75                  80

Leu Arg Tyr Val Asp Gln Leu Asn Glu Asp Pro His Thr His Gly Ile
                85                  90                  95

Ile Val Gln Leu Pro Leu Pro Ala His Leu Asp Glu Asp Arg Ile Thr
            100                 105                 110

Ser Arg Val Leu Ala Glu Lys Asp Val Asp Gly Phe Gly Pro Thr Asn
        115                 120                 125

Ile Gly Glu Leu Asn Lys Lys Asn Gly His Pro Phe Phe Leu Pro Cys
    130                 135                 140

Thr Pro Lys Gly Ile Ile Glu Leu Leu His Lys Ala Asn Val Thr Ile
145                 150                 155                 160

Glu Gly Ser Arg Ser Val Val Ile Gly Arg Ser Asp Ile Val Gly Ser
                165                 170                 175

Pro Val Ala Glu Leu Leu Lys Ser Leu Asn Ser Thr Val Thr Ile Thr
            180                 185                 190

His Ser Lys Thr Arg Asp Ile Ala Ser Tyr Leu His Asp Ala Asp Ile
        195                 200                 205

Val Val Val Ala Ile Gly Gln Pro Glu Phe Val Lys Gly Glu Trp Phe
    210                 215                 220

Lys Pro Arg Asp Gly Thr Ser Ser Asp Lys Lys Thr Val Val Ile Asp
225                 230                 235                 240

Val Gly Thr Asn Tyr Val Ala Asp Pro Ser Lys Lys Ser Gly Phe Lys
                245                 250                 255

Cys Val Gly Asp Val Glu Phe Asn Glu Ala Ile Lys Tyr Val His Leu
            260                 265                 270

Ile Thr Pro Val Pro Gly Gly Val Gly Pro Met Thr Val Ala Met Leu
        275                 280                 285

Met Gln Asn Thr Leu Ile Ala Ala Lys Arg Gln Met Glu Glu Ser Ser
    290                 295                 300

Lys Pro Leu Gln Ile Pro Pro Leu Pro Leu Lys Leu Leu Thr Pro Val
305                 310                 315                 320

Pro Ser Asp Ile Asp Ile Ser Arg Ala Gln Gln Pro Lys Leu Ile Asn
                325                 330                 335

Gln Leu Ala Gln Glu Leu Gly Ile Tyr Ser His Glu Leu Glu Leu Tyr
            340                 345                 350

Gly His Tyr Lys Ala Lys Ile Ser Pro Lys Val Ile Glu Arg Leu Gln
        355                 360                 365

```
Thr Arg Gln Asn Gly Lys Tyr Ile Leu Val Ser Gly Ile Thr Pro Thr
    370                 375                 380

Pro Leu Gly Glu Gly Lys Ser Thr Thr Thr Met Gly Leu Val Gln Ala
385                 390                 395                 400

Leu Thr Ala His Leu Gly Lys Pro Ala Ile Ala Asn Val Arg Gln Pro
                405                 410                 415

Ser Leu Gly Pro Thr Leu Gly Val Lys Gly Ala Ala Gly Gly Gly
                420                 425                 430

Tyr Ser Gln Val Ile Pro Met Asp Glu Phe Asn Leu His Leu Thr Gly
        435                 440                 445

Asp Ile His Ala Ile Gly Ala Ala Asn Asn Leu Leu Ala Ala Ala Ile
450                 455                 460

Asp Thr Arg Met Phe His Glu Thr Thr Gln Lys Asn Asp Ala Thr Phe
465                 470                 475                 480

Tyr Asn Arg Leu Val Pro Arg Lys Asn Gly Lys Arg Lys Phe Thr Pro
                485                 490                 495

Ser Met Gln Arg Arg Leu Asn Arg Leu Gly Ile Gln Lys Thr Asn Pro
                500                 505                 510

Asp Asp Leu Thr Pro Glu Glu Ile Asn Lys Phe Ala Arg Leu Asn Ile
                515                 520                 525

Asp Pro Asp Thr Ile Thr Ile Lys Arg Val Val Asp Ile Asn Asp Arg
530                 535                 540

Met Leu Arg Gln Ile Thr Ile Gly Gln Ala Pro Thr Glu Lys Asn His
545                 550                 555                 560

Thr Arg Val Thr Gly Phe Asp Ile Thr Val Ala Ser Glu Leu Met Ala
                565                 570                 575

Ile Leu Ala Leu Ser Lys Asp Leu Arg Asp Met Lys Glu Arg Ile Gly
                580                 585                 590

Arg Val Val Ala Ala Asp Val Asn Arg Ser Pro Val Thr Val Glu
        595                 600                 605

Asp Val Gly Cys Thr Gly Ala Leu Thr Ala Leu Leu Arg Asp Ala Ile
        610                 615                 620

Lys Pro Asn Leu Met Gln Thr Leu Glu Gly Thr Pro Val Leu Val His
625                 630                 635                 640

Ala Gly Pro Phe Ala Asn Ile Ser Ile Gly Ala Ser Ser Val Ile Ala
                645                 650                 655

Asp Arg Val Ala Leu Lys Leu Val Gly Thr Glu Pro Glu Ala Lys Thr
                660                 665                 670

Glu Ala Gly Tyr Val Val Thr Glu Ala Gly Phe Asp Phe Thr Met Gly
        675                 680                 685

Gly Glu Arg Phe Phe Asn Ile Lys Cys Arg Ser Ser Gly Leu Thr Pro
        690                 695                 700

Asn Ala Val Val Leu Val Ala Thr Val Arg Ala Leu Lys Ser His Gly
705                 710                 715                 720

Gly Ala Pro Asp Val Lys Pro Gly Gln Pro Leu Pro Ser Ala Tyr Thr
                725                 730                 735

Glu Glu Asn Ile Glu Phe Val Glu Lys Gly Ala Ala Asn Met Cys Lys
                740                 745                 750

Gln Ile Ala Asn Ile Lys Gln Phe Gly Val Pro Val Val Ala Ile
        755                 760                 765

Asn Lys Phe Glu Thr Asp Thr Glu Gly Glu Ile Ala Ala Ile Arg Lys
770                 775                 780

Ala Ala Leu Glu Ala Gly Ala Phe Glu Ala Val Thr Ser Asn His Trp
```

```
Ala Glu Gly Gly Lys Gly Ala Ile Asp Leu Ala Lys Ala Val Ile Glu
                805                 810                 815

Ala Ser Asn Gln Pro Val Asp Phe His Phe Leu Tyr Asp Val Asn Ser
            820                 825                 830

Ser Val Glu Asp Lys Leu Thr Thr Ile Val Gln Lys Met Tyr Gly Gly
        835                 840                 845

Ala Ala Ile Asp Ile Leu Pro Glu Ala Gln Arg Lys Ile Asp Met Tyr
    850                 855                 860

Lys Glu Gln Gly Phe Gly Asn Leu Pro Ile Cys Ile Ala Lys Thr Gln
865                 870                 875                 880

Tyr Ser Leu Ser His Asp Ala Thr Leu Lys Gly Val Pro Thr Gly Phe
                885                 890                 895

Thr Phe Pro Ile Arg Asp Val Arg Leu Ser Asn Gly Ala Gly Tyr Leu
            900                 905                 910

Tyr Ala Leu Ala Ala Glu Ile Gln Thr Ile Pro Gly Leu Ala Thr Tyr
        915                 920                 925

Ala Gly Tyr Met Ala Val Glu Val Asp Asp Asp Gly Glu Ile Asp Gly
    930                 935                 940

Leu Phe
945

<210> SEQ ID NO 2
<211> LENGTH: 2841
<212> TYPE: DNA
<213> ORGANISM: Saccharomyces cerevisiae

<400> SEQUENCE: 2
atggctggtc aagtgttgga cggcaaagca tgcgctcagc agtttagaag caatattgct      60
aatgaaatca aaagcattca aggtcacgtg cctgggtttg cacctaacct tgccatcatt     120
caagtaggca acagaccaga ctcagccaca tatgtacgca tgaagcgtaa ggcagctgaa     180
gaggccggca ttgttgctaa tttcattcat ttagatgaat ccgctactga atttgaagtt     240
ctgcgttacg tggaccagct gaatgaggac ccacatacac acggtattat cgtgcaacta     300
ccattacccg ctcatttgga cgaggataga atcacctcga gagtgttggc agaaaaggac     360
gtggacgggt cgggcccac caacattggc gaattgaata agaagaacgg acacccattc     420 ttttttgccct gcacgcccaa ggggatcatt gagctgcttc acaaggccaa cgtcacgatt     480
gaaggttccc ggtccgttgt gatcggaaga tctgacattg ttggctctcc tgttgcagaa     540
ttgttaaaat ctctaaactc caccgtcacc atcactcatt ctaaaacccg tgatatcgca     600
tcatacttac acgacgcgga catcgtagtc gttgccatcg ccaaccagaa atttgtgaag     660
ggtgaatggt tcaaaccaag agacggcact tccagtgata gaaaaccgt ggtaattgat     720 gttggcacca actacgttgc tgatccttcc aaaaagtccg gtttcaaatg tgttggtgac     780
gttgagttca tgaagcaat caaatacgtc catctaatca ctccagtgcc cggtggtgtg     840
ggccccatga cggtggctat gttaatgcaa ataccttga ttgctgccaa acgccaaatg     900
gaagaatcct cgaagccttt gcagattcct cccttgccat gaagttgct aacacctgtt     960 ccttccgata tagacatctc cagagcacaa cagccaaagc ttatcaacca gcttgctcaa    1020
gaattgggta tttactctca tgagttggag ctgtacggac attcaaggc caaaatttct    1080 cctaaagtca tcgaaaggct gcagacgcgc caaaatggta gtacatctt ggtgtctggt    1140 atcacaccaa caccactggg agagggtaaa tccactacaa caatgggtct gtccaggca    1200
```

-continued

```
ctaacggctc acttgggcaa gccagccatt gcgaacgtca gacaaccctc cctaggaccc   1260
actttaggtg tcaaaggtgg tgctgcgggt ggtggttatt cccaagtcat cccaatggac   1320
gaattcaact acatttgac tggtgacatt cacgccattg gtgcggctaa caacctactt    1380
gctgccgcta ttgacactag aatgttccat gagaccactc aaaagaacga cgctaccttc   1440
tacaacagac tagtgcctag aaagaacgga aagagaaagt ttactccctc catgcaaaga   1500
agattgaaca gactgggtat tcaaaagacc aaccccgatg atctaacacc cgaagagatc   1560
aacaaattcg ccagattgaa cattgacccg gacactatta ctatcaagag ggtggtcgat   1620
atcaacgaca gaatgttaag acaaatcacc attggtcaag cccctaccga agaaccac    1680
acaagagtta ctggattcga tatcaccgtt gcttctgaat tgatggctat tcttgctctt   1740
tcaaaggact tgagggacat gaaggaacgt attggaagag tcgttgttgc tgctgacgta   1800
aacaggtctc cagtcactgt tgaagatgtg ggttgtaccg gtgccttaac cgctttatta   1860
agagacgcta tcaagcccaa cttgatgcaa actttagaag gtactcctgt cttggtccat   1920
gccggcccat ttgccaacat ctctatcggt gcctcttctg ttattgctga tcgcgtggct   1980
ttgaaattgg ttggtaccga gccagaggca aaaacagaag ctggttatgt ggttactgaa   2040
gcagggttcg atttcactat gggtggtgaa agattcttca acatcaagtg ccgttcctct   2100
ggattgacac taatgctgt ggtcttggtt gctactgtta gggcattgaa gtcacacggt   2160
ggtgctccag atgtcaaacc tggccaacct ttaccttccg catacactga agagaatatc   2220
gagtttgtcg aaaaaggtgc cgctaacatg tgtaaacaaa ttgccaacat taagcaattt   2280
ggcgtccccg tcgttgtcgc aattaacaag tttgaaactg cactgaagg tgaaatagcc   2340
gccattagaa aagccgcttt ggaagctggt gcatttgaag ccgtaacctc taaccattgg   2400
gccgaaggtg gtaaaggtgc tatcgacttg gccaaggccg tcatcgaagc ttccaaccaa   2460
ccagtggact ccatttcct atatgacgtt aactcctccg ttgaagacaa attaactact   2520
atcgttcaaa agatgtacgg tggtgccgca atcgatatct tgcctgaagc acaacgcaag   2580
attgacatgt acaaggaaca aggtttcggt aacttgccaa tttgtatcgc caagacacaa   2640
tactctttat cccacgatgc aactttgaaa ggtgttccaa ccgggttcac tttcccccatc  2700
agagacgtca gattgtctaa tggtgctgga tacttatacg ctcttgccgc cgaaatacaa   2760
accattcctg gtttggctac ctatgctggt tacatggccg tggaagtcga tgatgacggt   2820
gagatcgatg gcctgttcta a                                             2841
```

<210> SEQ ID NO 3
<211> LENGTH: 469
<212> TYPE: PRT
<213> ORGANISM: Saccharomyces cerevisiae

<400> SEQUENCE: 3

Met Pro Tyr Thr Leu Ser Asp Ala His His Lys Leu Ile Thr Ser His
1               5                   10                  15

Leu Val Asp Thr Asp Pro Glu Val Asp Ser Ile Ile Lys Asp Glu Ile
            20                  25                  30

Glu Arg Gln Lys His Ser Ile Asp Leu Ile Ala Ser Glu Asn Phe Thr
        35                  40                  45

Ser Thr Ser Val Phe Asp Ala Leu Gly Thr Pro Leu Ser Asn Lys Tyr
    50                  55                  60

Ser Glu Gly Tyr Pro Gly Ala Arg Tyr Tyr Gly Gly Asn Glu His Ile
65                  70                  75                  80

Asp Arg Met Glu Ile Leu Cys Gln Gln Arg Ala Leu Lys Ala Phe His
            85                  90                  95

Val Thr Pro Asp Lys Trp Gly Val Asn Val Gln Thr Leu Ser Gly Ser
        100                 105                 110

Pro Ala Asn Leu Gln Val Tyr Gln Ala Ile Met Lys Pro His Glu Arg
            115                 120                 125

Leu Met Gly Leu Tyr Leu Pro Asp Gly Gly His Leu Ser His Gly Tyr
        130                 135                 140

Ala Thr Glu Asn Arg Lys Ile Ser Ala Val Ser Thr Tyr Phe Glu Ser
145                 150                 155                 160

Phe Pro Tyr Arg Val Asn Pro Glu Thr Gly Ile Ile Asp Tyr Asp Thr
                165                 170                 175

Leu Glu Lys Asn Ala Ile Leu Tyr Arg Pro Lys Val Leu Val Ala Gly
            180                 185                 190

Thr Ser Ala Tyr Cys Arg Leu Ile Asp Tyr Lys Arg Met Arg Glu Ile
        195                 200                 205

Ala Asp Lys Cys Gly Ala Tyr Leu Met Val Asp Met Ala His Ile Ser
210                 215                 220

Gly Leu Ile Ala Ala Gly Val Ile Pro Ser Pro Phe Glu Tyr Ala Asp
225                 230                 235                 240

Ile Val Thr Thr Thr Thr His Lys Ser Leu Arg Gly Pro Arg Gly Ala
                245                 250                 255

Met Ile Phe Phe Arg Arg Gly Val Arg Ser Ile Asn Pro Lys Thr Gly
            260                 265                 270

Lys Glu Val Leu Tyr Asp Leu Glu Asn Pro Ile Asn Phe Ser Val Phe
        275                 280                 285

Pro Gly His Gln Gly Gly Pro His Asn His Thr Ile Ala Ala Leu Ala
290                 295                 300

Thr Ala Leu Lys Gln Ala Ala Thr Pro Glu Phe Lys Glu Tyr Gln Thr
305                 310                 315                 320

Gln Val Leu Lys Asn Ala Lys Ala Leu Glu Ser Glu Phe Lys Asn Leu
                325                 330                 335

Gly Tyr Arg Leu Val Ser Asn Gly Thr Asp Ser His Met Val Leu Val
            340                 345                 350

Ser Leu Arg Glu Lys Gly Val Asp Gly Ala Arg Val Glu Tyr Ile Cys
        355                 360                 365

Glu Lys Ile Asn Ile Ala Leu Asn Lys Asn Ser Ile Pro Gly Asp Lys
370                 375                 380

Ser Ala Leu Val Pro Gly Gly Val Arg Ile Gly Ala Pro Ala Met Thr
385                 390                 395                 400

Thr Arg Gly Met Gly Glu Glu Asp Phe His Arg Ile Val Gln Tyr Ile
                405                 410                 415

Asn Lys Ala Val Glu Phe Ala Gln Gln Val Gln Gln Ser Leu Pro Lys
            420                 425                 430

Asp Ala Cys Arg Leu Lys Asp Phe Lys Ala Lys Val Asp Glu Gly Ser
        435                 440                 445

Asp Val Leu Asn Thr Trp Lys Lys Glu Ile Tyr Asp Trp Ala Gly Glu
450                 455                 460

Tyr Pro Leu Ala Val
465

<210> SEQ ID NO 4
<211> LENGTH: 1410

<212> TYPE: DNA
<213> ORGANISM: Saccharomyces cerevisiae

<400> SEQUENCE: 4

```
atgccttaca ctctatccga cgctcatcat aagttgatca cctctcattt ggtggacacc      60
gaccctgaag tggactccat tatcaaggat gaaattgaaa gacaaaagca ctccatcgat     120
ttgattgctt ctgaaaattt cacctcaacc tccgttttcg atgcccttgg aactccattg     180
tccaacaaat actctgaagg ttatccaggt gctcgttact acggtggtaa tgaacacatt     240
gacagaatgg aaattctatg tcaacaaaga gctttgaaag cttttccatgt tactccagac    300
aaatggggtg ttaacgtcca aactttatct ggttctcctg ctaacttgca ggtttatcaa     360
gctattatga agcctcatga agattgatg ggtctatacc taccagatgg tggtcatttg      420
tctcacggtt acgctactga aaacagaaaa atttctgctg tttccacata cttcgaatct    480
ttcccataca gagttaaccc agaaaccggt attatcgact acgatacttt agaaaagaac     540
gccatcctat atagaccaaa ggttcttgtt gctggtactt cagcatactg tcgtttaatt    600
gactacaaga gaatgagaga atcgccgac aaatgtggtg cttacttgat ggtagacatg      660
gcccacattt ctggtttgat cgccgcaggt gtcatcccat ctcctttcga atacgctgat    720
atcgttacca ccaccactca caagtctttg agaggtccac gtggtgctat gattttcttc    780
agaagaggtg tgagatctat caaccctaag accggtaagg aagttctata cgacttggaa    840
aacccaatta acttctctgt tttcccaggt caccaaggtg gtccacacaa ccataccatt    900
gctgctttgg ccactgcttt gaagcaagct gccactccag aattcaagga ataccaaact    960
caagtcttga gaatgctaa ggctttggaa agtgaattta agaacttggg ctacagatta   1020
gtttccaacg gtaccgattc tcacatggtt ctagtatcct tgagagaaaa gggtgttgat   1080
ggtgctcgtg ttgaatacat ttgtgaaaag attaacattg ctttgaacaa aaactctatt   1140
ccaggtgaca atctgctttt ggttccaggt ggtgtccgta ttggggctcc agccatgacc   1200
actagaggaa tgggtgaaga agatttccac agaattgttc aatacattaa caaggctgta   1260
gaattcgctc aacaagttca acaaagcttg ccaaaggatg cttgtagatt aaaggacttc   1320
aaagccaagg tcgacgaagg ctctgatgtt ttgaacacct ggaaaaagga aatttacgac   1380
tgggctggcg aatacccatt ggctgtgtaa                                     1410
```

<210> SEQ ID NO 5
<211> LENGTH: 320
<212> TYPE: PRT
<213> ORGANISM: Saccharomyces cerevisiae

<400> SEQUENCE: 5

```
Met Ser Lys Pro Gly Arg Thr Ile Leu Ala Ser Lys Val Ala Glu Thr
 1               5                  10                  15

Phe Asn Thr Glu Ile Ile Asn Asn Val Glu Glu Tyr Lys Lys Thr His
                20                  25                  30

Asn Gly Gln Gly Pro Leu Leu Val Gly Phe Leu Ala Asn Asn Asp Pro
            35                  40                  45

Ala Ala Lys Met Tyr Ala Thr Trp Thr Gln Lys Thr Ser Glu Ser Met
        50                  55                  60

Gly Phe Arg Tyr Asp Leu Arg Val Ile Glu Asp Lys Asp Phe Leu Glu
 65                  70                  75                  80

Glu Ala Ile Ile Gln Ala Asn Gly Asp Asp Ser Val Asn Gly Ile Met
                85                  90                  95
```

Val Tyr Phe Pro Val Phe Gly Asn Ala Gln Asp Gln Tyr Leu Gln Gln
                100                 105                 110

Val Val Cys Lys Glu Lys Asp Val Glu Gly Leu Asn His Val Tyr Tyr
            115                 120                 125

Gln Asn Leu Tyr His Asn Val Arg Tyr Leu Asp Lys Glu Asn Arg Leu
        130                 135                 140

Lys Ser Ile Leu Pro Cys Thr Pro Leu Ala Ile Val Lys Ile Leu Glu
145                 150                 155                 160

Phe Leu Lys Ile Tyr Asn Asn Leu Leu Pro Glu Gly Asn Arg Leu Tyr
                165                 170                 175

Gly Lys Lys Cys Ile Val Ile Asn Arg Ser Glu Ile Val Gly Arg Pro
            180                 185                 190

Leu Ala Ala Leu Leu Ala Asn Asp Gly Ala Thr Val Tyr Ser Val Asp
        195                 200                 205

Val Asn Asn Ile Gln Lys Phe Thr Arg Gly Glu Ser Leu Lys Leu Asn
210                 215                 220

Lys His His Val Glu Asp Leu Gly Glu Tyr Ser Glu Asp Leu Leu Lys
225                 230                 235                 240

Lys Cys Ser Leu Asp Ser Asp Val Val Ile Thr Gly Val Pro Ser Glu
                245                 250                 255

Asn Tyr Lys Phe Pro Thr Glu Tyr Ile Lys Glu Gly Ala Val Cys Ile
            260                 265                 270

Asn Phe Ala Cys Thr Lys Asn Phe Ser Asp Asp Val Lys Glu Lys Ala
        275                 280                 285

Ser Leu Tyr Val Pro Met Thr Gly Lys Val Thr Ile Ala Met Leu Leu
    290                 295                 300

Arg Asn Met Leu Arg Leu Val Arg Asn Val Glu Leu Ser Lys Glu Lys
305                 310                 315                 320

<210> SEQ ID NO 6
<211> LENGTH: 963
<212> TYPE: DNA
<213> ORGANISM: Saccharomyces cerevisiae

<400> SEQUENCE: 6
atgtcgaagc ctggtcgtac tattttagca agcaaggtcg ccgaaacttt caataccgaa       60
ataattaaca acgtagagga atacaagaag acacataatg gtcaaggtcc ccttcttgtg      120
ggattcctag ctaataatga tcctgctgca agatgtatg ctacatggac tcaaaagact       180
agcgagtcaa tggggttccg ctatgactta agggtcattg aagataagga ttttttggaa      240
gaagcgataa tacaagctaa cggcgatgac tctgtgaacg gtatcatggt atactttcct      300
gttttcggta tgctcaagat cagtatttg caacaggttg tgtgcaagga aaagatgta       360 gaagggttaa atcatgttta ctaccaaaac ctgtaccata atgtcagata cctggacaaa      420
gaaaaccgtt tgaaatccat tctaccttgc acaccactag ctatcgttaa gatattggaa      480
ttcttgaaaa tttacaacaa tttgttacca gaaggaaaca gactgtatgg aagaaatgc       540 atagtaatta acaggtcaga atcgtcggt agaccactgg cggcgctatt agccaatgac       600
ggtgccacag tatactctgt ggacgttaac aacattcaaa aattcacccg tggtgaaagt      660
ttgaaattaa acaagcatca tgtggaagac cttggggagt actctgaaga tctgttgaaa      720
aagtgttctc ttgattcaga tgtggtcatc actggtgtcc ctagtgaaaa ttacaaattc      780
cccaccgaat acatcaaaga aggtgccgtc tgcatcaatt ttgcatgcac caaaaatttt      840
agcgatgatg tcaaggaaaa agcttctctt tacgttccaa tgactggtaa agttaccatt      900
gcaatgttgt tgagaaacat gttacgttta gtaaggaacg tagaactgtc taaagaaaaa    960
tag                                                                  963

<210> SEQ ID NO 7
<211> LENGTH: 530
<212> TYPE: PRT
<213> ORGANISM: Saccharomyces cerevisiae

<400> SEQUENCE: 7

Met Lys Glu Asn Asp Met Asn Asn Gly Val Asp Lys Trp Val Asn Glu
1               5                   10                  15

Glu Asp Gly Arg Asn Asp His His Asn Asn Asn Asn Leu Met Lys
            20                  25                  30

Lys Ala Met Met Asn Asn Glu Gln Ile Asp Arg Thr Gln Asp Ile Asp
        35                  40                  45

Asn Ala Lys Glu Met Leu Arg Lys Ile Ser Ser Glu Ser Ser Ser Arg
    50                  55                  60

Arg Ser Ser Leu Leu Asn Lys Asp Ser Ser Leu Val Asn Gly Asn Ala
65                  70                  75                  80

Asn Ser Gly Gly Gly Thr Ser Ile Asn Gly Thr Arg Gly Ser Ser Lys
                85                  90                  95

Ser Ser Asn Thr His Phe Gln Tyr Ala Ser Thr Ala Tyr Gly Val Arg
            100                 105                 110

Met Leu Ser Lys Asp Ile Ser Asn Thr Lys Val Glu Leu Asp Val Glu
        115                 120                 125

Asn Leu Met Ile Val Thr Lys Leu Asn Asp Val Ser Leu Tyr Phe Leu
    130                 135                 140

Thr Arg Glu Leu Val Glu Trp Val Leu Val His Phe Pro Arg Val Thr
145                 150                 155                 160

Val Tyr Val Asp Ser Glu Leu Lys Asn Ser Lys Lys Phe Ala Ala Gly
                165                 170                 175

Glu Leu Cys Glu Asp Ser Lys Cys Arg Glu Ser Arg Ile Lys Tyr Trp
            180                 185                 190

Thr Lys Asp Phe Ile Arg Glu His Asp Val Phe Phe Asp Leu Val Val
        195                 200                 205

Thr Leu Gly Gly Asp Gly Thr Val Leu Phe Val Ser Ser Ile Phe Gln
    210                 215                 220

Arg His Val Pro Pro Val Met Ser Phe Ser Leu Gly Ser Leu Gly Phe
225                 230                 235                 240

Leu Thr Asn Phe Lys Phe Glu His Phe Arg Glu Asp Leu Pro Arg Ile
                245                 250                 255

Met Asn His Lys Ile Lys Thr Asn Leu Arg Leu Arg Leu Glu Cys Thr
            260                 265                 270

Ile Tyr Arg Arg His Arg Pro Glu Val Asp Pro Asn Thr Gly Lys Lys
        275                 280                 285

Ile Cys Val Val Glu Lys Leu Ser Thr His His Ile Leu Asn Glu Val
    290                 295                 300

Thr Ile Asp Arg Gly Pro Ser Pro Phe Leu Ser Met Leu Glu Leu Tyr
305                 310                 315                 320

Gly Asp Gly Ser Leu Met Thr Val Ala Gln Ala Asp Gly Leu Ile Ala
                325                 330                 335

Ala Thr Pro Thr Gly Ser Thr Ala Tyr Ser Leu Ser Ala Gly Gly Ser
            340                 345                 350

```
Leu Val Cys Pro Thr Val Asn Ala Ile Ala Leu Thr Pro Ile Cys Pro
            355                 360                 365

His Ala Leu Ser Phe Arg Pro Ile Ile Leu Pro Glu Ser Ile Asn Leu
        370                 375                 380

Lys Val Lys Val Ser Met Lys Ser Arg Ala Pro Ala Trp Ala Ala Phe
385                 390                 395                 400

Asp Gly Lys Asp Arg Ile Glu Leu Gln Lys Gly Asp Phe Ile Thr Ile
                405                 410                 415

Cys Ala Ser Pro Tyr Ala Phe Pro Thr Val Glu Ala Ser Pro Asp Glu
            420                 425                 430

Phe Ile Asn Ser Ile Ser Arg Gln Leu Asn Trp Asn Val Arg Glu Gln
        435                 440                 445

Gln Lys Ser Phe Thr His Ile Leu Ser Gln Lys Asn Gln Glu Lys Tyr
    450                 455                 460

Ala His Glu Ala Asn Lys Val Arg Asn Gln Ala Glu Pro Leu Glu Val
465                 470                 475                 480

Ile Arg Asp Lys Tyr Ser Leu Glu Ala Asp Ala Thr Lys Glu Asn Asn
                485                 490                 495

Asn Gly Ser Asp Asp Glu Ser Asp Glu Ser Val Asn Cys Glu Ala
            500                 505                 510

Cys Lys Leu Lys Pro Ser Ser Val Pro Lys Pro Ser Gln Ala Arg Phe
        515                 520                 525

Ser Val
    530

<210> SEQ ID NO 8
<211> LENGTH: 1593
<212> TYPE: DNA
<213> ORGANISM: Saccharomyces cerevisiae

<400> SEQUENCE: 8
atgaaggaga atgacatgaa taatggcgta gataaatggg taaatgagga agatggtcga      60
aatgatcatc ataacaacaa taataacttg atgaagaagg ccatgatgaa caatgagcaa     120
attgatagaa ctcaggatat cgacaacgcc aaagaaatgt tgaggaaaat atcaagtgaa     180
agcagctcgc gcagaagctc cctgttgaat aaagattcat ctctcgtgaa cggcaatgca     240
aacagtggcg gtggtacgag cattaacgga acaagaggaa gttctaagag tagtaataca     300
cactttcagt atgcctccac ggcgtatggt gtaagaatgt tgagtaaaga tatatctaat     360
accaaagtgg aactggatgt ggaaaatttg atgattgtta cgaaactcaa cgatgtctca     420
ctgtatttct taacaagaga gttggtagaa tgggttttgg tacattttcc acgtgtgact     480
gtttatgtgg attccgaatt gaaaacagc aaaaaatttg ccgctggcga gttatgtgaa     540
gatagtaaat gtagagaatc aaggatcaag tattggacaa aggatttcat cagggaacat     600
gatgtttttct tcgatttggt agtgactttg ggtggcgacg gtactgttct ttttgtaagt     660
tccatttttc agagacatgt accacccgtt atgtcgtttt cattagggtc tctaggattt     720
ttaacaaatt ttaagtttga acatttcagg gaggatttac ctcggattat gaatcataaa     780
atcaagacaa atttacggtt gaggttggag tgcacaattt atcgtagaca ccgccctgaa     840
gtagacccaa acacggggaa gaaatatgt gtggtggaaa actaagcac acaccacatt     900
ttgaacgaag tgaccatcga tcgtggtcca agtccttttc tatccatgtt agaattgtat     960
ggtgacggct cattaatgac cgttgcgcag gcggacggga tgattgctgc tactccgact    1020
gggtccacgg cctattcttt gagtgcaggt gggtcattgg tatgcccaac cgtcaatgca    1080
```

-continued

```
atcgctttaa cacccatttg tccacatgca ttgagtttca gacccatcat cttaccagaa    1140
agtataaatt taaaagtgaa agtctcgatg aagtcaaggg ctccagcatg ggcggctttt    1200
gatgggaaag atagaattga attgcaaaaa ggtgatttta taaccatatg cgccagccca    1260
tatgcttttc caaccgtgga agcctcgccc gatgagttta ttaacagtat cagtcgacaa    1320
ctaaactgga atgtgaggga acaacaaaag tcctttacgc atattttgtc ccaaaagaac    1380
caagaaaaat atgcacatga ggcgaacaaa gtcagaaatc aagcagaacc tttagaggta    1440
ataagagata aatactctct ggaagcagac gctactaagg aaaacaacaa cggaagcgat    1500
gatgagagcg acgatgagag tgtaaactgc gaagcttgca aattaaagcc ttcgagcgtc    1560
ccaaaacctt ctcaagcaag gttttcagta taa                                 1593
```

<210> SEQ ID NO 9
<211> LENGTH: 495
<212> TYPE: PRT
<213> ORGANISM: Saccharomyces cerevisiae

<400> SEQUENCE: 9

Met Lys Thr Asp Arg Leu Leu Ile Asn Ala Ser Pro Glu Thr Cys Thr
1               5                   10                  15

Lys Gly Asp Ala Glu Met Asp Thr Met Asp Thr Ile Asp Arg Met Thr
            20                  25                  30

Ser Val Lys Val Leu Ala Glu Gly Lys Val Leu Ser Asn Phe Glu Glu
        35                  40                  45

Pro Gly Leu Met Arg Cys Gly Tyr His Asp Ala Lys Asn Trp Val Arg
    50                  55                  60

Arg Leu Ser Ser Glu Thr Ile Val Gly Glu Asp Thr Ser Asn Leu Tyr
65                  70                  75                  80

Pro Phe Tyr Val Asp Thr Ala Tyr Asp Val Arg Arg Leu Arg Lys Asp
                85                  90                  95

Leu Ile Asn Ala Lys Val Asp Leu Gln Val Glu Asn Leu Ile Ile Ile
            100                 105                 110

Cys Asn Ile Asn Asp Ile Ser Thr Val Phe Leu Met Arg Glu Val Val
        115                 120                 125

Glu Trp Ile Leu Arg Asn Phe His Ser Ile Thr Val Tyr Val Gln Asp
    130                 135                 140

Ile Phe Lys Lys Ser Thr Gln Phe Ala Val Gly Asp Leu Cys Lys Asp
145                 150                 155                 160

Ser Asn Cys Ser Lys Asn Arg Val Lys Tyr Trp Ser Lys Glu Phe Val
                165                 170                 175

Lys Lys His Asp Ser Phe Phe Asp Leu Met Ile Thr Leu Gly Gly Asp
            180                 185                 190

Gly Thr Val Leu Phe Ala Ser Ser Ile Phe Thr Lys Asp Val Pro Pro
        195                 200                 205

Ile Val Pro Phe Ala Leu Gly Ser Leu Gly Phe Leu Thr Asn Phe Glu
    210                 215                 220

Phe Gln Asn Phe Lys Glu Thr Leu Lys His Ile Leu Thr Asp Glu Val
225                 230                 235                 240

Arg Ile Asn Leu Arg Met Arg Leu Gln Cys Lys Leu Tyr Arg Arg Asn
                245                 250                 255

Lys Pro Glu Ile Asp Ala Ala Thr Gly Arg Lys Ile Cys Tyr Ile Asp
            260                 265                 270

Phe Ile Ser Glu His His Val Leu Asn Glu Val Thr Ile Asp Arg Gly

```
                     275                 280                 285
          Pro Ala Pro Cys Leu Ser Leu Leu Glu Leu Tyr Gly Asn Asp Ser Leu
          290                 295                 300

Met Thr Lys Val Gln Gly Asp Gly Leu Ile Val Ala Thr Pro Thr Gly
          305                 310                 315                 320

Ser Thr Ala Tyr Ser Leu Ser Ala Gly Gly Ser Leu Ile Ser Pro Ser
                          325                 330                 335

Val Asn Ala Ile Ala Val Thr Pro Ile Cys Pro His Thr Leu Ser Phe
                      340                 345                 350

Arg Pro Ile Ile Leu Pro Asp Ser Met Glu Leu Lys Val Arg Val Asp
                  355                 360                 365

Met Asn Ser Arg Gly Thr Ser Trp Val Asn Phe Asp Gly Lys Asp Arg
          370                 375                 380

Val Glu Leu Lys Gln Gly Asp Tyr Val Val Ile Thr Ala Ser Pro Tyr
          385                 390                 395                 400

Ser Val Pro Thr Ile Glu Ser Ser Ala Ser Glu Phe Phe Glu Ser Ile
                          405                 410                 415

Ser Lys Asn Leu Asn Trp Asn Asp Arg Glu Glu Gln Lys Pro Phe Ala
                      420                 425                 430

His Ile Leu Ser Pro Lys Asn Gln Glu Lys Tyr Arg Leu Asp Ser Ser
                  435                 440                 445

Lys Asn Gly Asn Asp Thr Ile Ser Asn Pro Leu Glu Ser Ser Cys Ile
          450                 455                 460

Ser Ser Asp Ala Gln Asp Glu Glu Arg Lys Ser Val Thr Glu Thr Glu
          465                 470                 475                 480

Thr Glu Ile Val Val Glu Arg Thr Arg Gln Ala His Phe Ala Ile
                          485                 490                 495
```

<210> SEQ ID NO 10
<211> LENGTH: 1488
<212> TYPE: DNA
<213> ORGANISM: Saccharomyces cerevisiae

<400> SEQUENCE: 10

| | | | | | |
|---|---|---|---|---|---|
| atgaaaactg | atagattact | gattaacgct | tccccggaga | catgtaccaa | gggagatgct | 60 |
| gagatggata | ctatggatac | tattgacaga | atgacatcag | ttaaagtttt | agcggaaggc | 120 |
| aaggtattaa | gcaacttcga | agaaccgggc | ttaatgaggt | gcggttatca | tgatgcaaaa | 180 |
| aactgggtca | gaagattatc | gagcgaaaca | attgtcggtg | aggacacgag | taatttatac | 240 |
| ccatttatg | ttgatactgc | atacgatgta | aggcgtttga | gaaaggatct | tataaatgct | 300 |
| aaggttgact | tgcaggttga | aaacctgata | taatctgca | atattaatga | tatttccact | 360 |
| gtatttctca | tgagagaagt | ggtggaatgg | atcttacgca | atttccattc | aataactgta | 420 |
| tatgtacaag | atatttttaa | aaagtcaact | cagtttgctg | ttggtgaccct | ctgcaaagac | 480 |
| agcaattgca | gtaaaaacag | agtaaagtat | tggtcaaaag | aatttgttaa | aaacacgat | 540 |
| tcattctttg | acttgatgat | tacactaggg | ggtgatggaa | ctgtcctttt | tgcttcatct | 600 |
| atattcacga | aagatgttcc | gccgattgtt | ccatttgccc | ttggatcatt | aggatttcta | 660 |
| acaaattttg | aatttcaaaa | tttcaaagaa | acgttgaaac | atatcttaac | agatgaggtt | 720 |
| cgtattaatt | tacgaatgag | gttgcaatgc | aaactctacc | gtagaaataa | accagaaatt | 780 |
| gatgccgcaa | ctgggagaaa | aatatgttac | atcgatttca | tctccgaaca | tcacgtattg | 840 |
| aacgaagtaa | ccatagatag | aggtccagct | ccttgtttat | ccctattaga | actctatgga | 900 |

-continued

```
aacgactcac taatgactaa ggttcaggga gatggattga ttgttgccac gcctacggga    960
tccacggcat actccattgag tgcaggaggc tctttaatat cgccaagcgt aaatgccata   1020
gcggtgacgc ctatatgtcc tcatactttg agctttaggc ctataatttt accagatagc   1080
atggaattaa aagttagagt agatatgaac tcaagaggga cgtcgtgggt gaattttgac   1140
ggaaaagata gagttgaatt gaaacagggt gactatgttg tgataactgc aagcccctat   1200
tcggtaccga ctatcgagtc atctgccagt gaatttttg aaagtatcag taaaaatctt    1260
aattggaatg accgcgaaga gcagaagcca tttgcacata ttctctcgcc aaaaaatcaa   1320
gaaaaatata gattagactc atcgaaaaat ggaaacgaca ccataagtaa tcccctcgag   1380
agttcatgca taagctcaga tgcacaagat gaggagagga aatccgtaac ggaaacagaa   1440
acagaaatag ttgttgaacg gactcgtcag gctcattttg caatctaa                1488
```

<210> SEQ ID NO 11
<211> LENGTH: 414
<212> TYPE: PRT
<213> ORGANISM: Saccharomyces cerevisiae

<400> SEQUENCE: 11

```
Met Phe Val Arg Val Lys Leu Asn Lys Pro Val Lys Trp Tyr Arg Phe
 1               5                  10                  15

Tyr Ser Thr Leu Asp Ser His Ser Leu Lys Leu Gln Ser Gly Ser Lys
            20                  25                  30

Phe Val Lys Ile Lys Pro Val Asn Asn Leu Arg Ser Ser Ser Ser Ala
        35                  40                  45

Asp Phe Val Ser Pro Pro Asn Ser Lys Leu Gln Ser Leu Ile Trp Gln
    50                  55                  60

Asn Pro Leu Gln Asn Val Tyr Ile Thr Lys Lys Pro Trp Thr Pro Ser
65                  70                  75                  80

Thr Arg Glu Ala Met Val Glu Phe Ile Thr His Leu His Glu Ser Tyr
                85                  90                  95

Pro Glu Val Asn Val Ile Val Gln Pro Asp Val Ala Glu Glu Ile Ser
            100                 105                 110

Gln Asp Phe Lys Ser Pro Leu Glu Asn Asp Pro Asn Arg Pro His Ile
        115                 120                 125

Leu Tyr Thr Gly Pro Glu Gln Asp Ile Val Asn Arg Thr Asp Leu Leu
    130                 135                 140

Val Thr Leu Gly Gly Asp Gly Thr Ile Leu His Gly Val Ser Met Phe
145                 150                 155                 160

Gly Asn Thr Gln Val Pro Pro Val Leu Ala Phe Ala Leu Gly Thr Leu
                165                 170                 175

Gly Phe Leu Ser Pro Phe Asp Phe Lys Glu His Lys Lys Val Phe Gln
            180                 185                 190

Glu Val Ile Ser Ser Arg Ala Lys Cys Leu His Arg Thr Arg Leu Glu
        195                 200                 205

Cys His Leu Lys Lys Lys Asp Ser Asn Ser Ser Ile Val Thr His Ala
    210                 215                 220

Met Asn Asp Ile Phe Leu His Arg Gly Asn Ser Pro His Leu Thr Asn
225                 230                 235                 240

Leu Asp Ile Phe Ile Asp Gly Glu Phe Leu Thr Arg Thr Thr Ala Asp
                245                 250                 255

Gly Val Ala Leu Ala Thr Pro Thr Gly Ser Thr Ala Tyr Ser Leu Ser
            260                 265                 270
```

```
Ala Gly Gly Ser Ile Val Ser Pro Leu Val Pro Ala Ile Leu Met Thr
            275                 280                 285

Pro Ile Cys Pro Arg Ser Leu Ser Phe Arg Pro Leu Ile Leu Pro His
        290                 295                 300

Ser Ser His Ile Arg Ile Lys Ile Gly Ser Lys Leu Asn Gln Lys Pro
305                 310                 315                 320

Val Asn Ser Val Val Lys Leu Ser Val Asp Gly Ile Pro Gln Gln Asp
                325                 330                 335

Leu Asp Val Gly Asp Glu Ile Tyr Val Ile Asn Glu Val Gly Thr Ile
            340                 345                 350

Tyr Ile Asp Gly Thr Gln Leu Pro Thr Thr Arg Lys Thr Glu Asn Asp
        355                 360                 365

Phe Asn Asn Ser Lys Lys Pro Lys Arg Ser Gly Ile Tyr Cys Val Ala
    370                 375                 380

Lys Thr Glu Asn Asp Trp Ile Arg Gly Ile Asn Glu Leu Leu Gly Phe
385                 390                 395                 400

Asn Ser Ser Phe Arg Leu Thr Lys Arg Gln Thr Asp Asn Asp
            405                 410

<210> SEQ ID NO 12
<211> LENGTH: 1245
<212> TYPE: DNA
<213> ORGANISM: Saccharomyces cerevisiae

<400> SEQUENCE: 12
atgtttgtca gggttaaatt gaataaacca gtaaaatggt ataggttcta tagtacgttg      60
gattcacatt ccctaaagtt acagagcggc tcgaagtttg taaaaataaa gccagtaaat    120
aacttgagga gtagttcatc agcagatttc gtgtccccac caaattccaa attacaatct    180
ttaatctggc agaaccccttt acaaaatgtt tatataacta aaaaaccatg gactccatcc    240
acaagagaag cgatggttga attcataact catttacatg agtcataccc cgaggtgaac    300
gtcattgttc aacccgatgt ggcagaagaa atttcccagg atttcaaatc tcctttggag    360
aatgatccca accgacctca tatactttat actggtcctg aacaagatat cgtaaacaga    420
acagacttat tggtgacatt gggaggtgat gggactattt tacacggcgt atcaatgttc    480
ggaaatacgc aagttcctcc ggttttagca tttgctctgg gcactctggg ctttctatca    540
ccgtttgatt ttaaggagca taaaaaggtc tttcaggaag taatcagctc tagagccaaa    600
tgtttgcata gaacacggct agaatgtcat ttgaaaaaaa aggatagcaa ctcatctatt    660
gtgacccatg ctatgaatga catattctta catagggggta attcccctca tctcactaac    720
ctggacattt tcattgatgg ggaattttttg acaagaacga cagcagatgg tgttgcattg    780
gccactccaa cgggttccac agcatattca ttatcagcag gtggatctat tgtttcccca    840
ttagtccctg ctattttaat gacaccaatt tgtcctcgct ctttgtcatt ccgaccactg    900
attttgcctc attcatccca cattaggata aagatagtt ccaaattgaa ccaaaaacca    960
gtcaacagtg tggtaaaact ttctgttgat ggtattcctc aacaggattt agatgttggt   1020
gatgaaattt atgttataaa tgaggtcggc actatataca tagatggtac tcagcttccg   1080
acgacaagaa aaactgaaaa tgactttaat aattcaaaaa agcctaaaag gtcagggatt   1140
tattgtgtcg ccaagaccga gaatgactgg attagaggaa tcaatgaact tttaggattc   1200
aattctagct ttaggctgac caagagacag actgataatg attaa                   1245

<210> SEQ ID NO 13
```

<211> LENGTH: 371
<212> TYPE: PRT
<213> ORGANISM: Saccharomyces cerevisiae

<400> SEQUENCE: 13

Met Ser Ser Ser Ala Asp Phe Val Ser Pro Pro Asn Ser Lys Leu Gln
1               5                   10                  15

Ser Leu Ile Trp Gln Asn Pro Leu Gln Asn Val Tyr Ile Thr Lys Lys
            20                  25                  30

Pro Trp Thr Pro Ser Thr Arg Glu Ala Met Val Glu Phe Ile Thr His
        35                  40                  45

Leu His Glu Ser Tyr Pro Glu Val Asn Val Ile Val Gln Pro Asp Val
    50                  55                  60

Ala Glu Glu Ile Ser Gln Asp Phe Lys Ser Pro Leu Glu Asn Asp Pro
65                  70                  75                  80

Asn Arg Pro His Ile Leu Tyr Thr Gly Pro Glu Gln Asp Ile Val Asn
                85                  90                  95

Arg Thr Asp Leu Leu Val Thr Leu Gly Gly Asp Gly Thr Ile Leu His
            100                 105                 110

Gly Val Ser Met Phe Gly Asn Thr Gln Val Pro Pro Val Leu Ala Phe
        115                 120                 125

Ala Leu Gly Thr Leu Gly Phe Leu Pro Phe Asp Phe Lys Glu His
    130                 135                 140

Lys Lys Val Phe Gln Glu Val Ile Ser Ser Arg Ala Lys Cys Leu His
145                 150                 155                 160

Arg Thr Arg Leu Glu Cys His Leu Lys Lys Lys Asp Ser Asn Ser Ser
                165                 170                 175

Ile Val Thr His Ala Met Asn Asp Ile Phe Leu His Arg Gly Asn Ser
            180                 185                 190

Pro His Leu Thr Asn Leu Asp Ile Phe Ile Asp Gly Glu Phe Leu Thr
        195                 200                 205

Arg Thr Thr Ala Asp Gly Val Ala Leu Ala Thr Pro Thr Gly Ser Thr
    210                 215                 220

Ala Tyr Ser Leu Ser Ala Gly Gly Ser Ile Val Ser Pro Leu Val Pro
225                 230                 235                 240

Ala Ile Leu Met Thr Pro Ile Cys Pro Arg Ser Leu Ser Phe Arg Pro
                245                 250                 255

Leu Ile Leu Pro His Ser Ser His Ile Arg Ile Lys Ile Gly Ser Lys
            260                 265                 270

Leu Asn Gln Lys Pro Val Asn Ser Val Val Lys Leu Ser Val Asp Gly
        275                 280                 285

Ile Pro Gln Gln Asp Leu Asp Val Gly Asp Glu Ile Tyr Val Ile Asn
    290                 295                 300

Glu Val Gly Thr Ile Tyr Ile Asp Gly Thr Gln Leu Pro Thr Thr Arg
305                 310                 315                 320

Lys Thr Glu Asn Asp Phe Asn Asn Ser Lys Pro Lys Arg Ser Gly
                325                 330                 335

Ile Tyr Cys Val Ala Lys Thr Glu Asn Asp Trp Ile Arg Gly Ile Asn
            340                 345                 350

Glu Leu Leu Gly Phe Asn Ser Ser Phe Arg Leu Thr Lys Arg Gln Thr
        355                 360                 365

Asp Asn Asp
    370

<210> SEQ ID NO 14
<211> LENGTH: 1116
<212> TYPE: DNA
<213> ORGANISM: Saccharomyces cerevisiae

<400> SEQUENCE: 14

```
atgagttcat cagcagattt cgtgtcccca ccaaattcca aattacaatc tttaatctgg      60
cagaacccct tacaaaatgt ttatataact aaaaaaccat ggactccatc cacaagagaa     120
gcgatggttg aattcataac tcatttacat gagtcatacc ccgaggtgaa cgtcattgtt     180
caacccgatg tggcagaaga aatttcccag gatttcaaat ctccttttgga gaatgatccc    240
aaccgacctc atatacttta tactggtcct gaacaagata tcgtaaacag aacagactta    300
ttggtgacat tgggaggtga tgggactatt ttacacggcg tatcaatgtt cggaaatacg    360
caagttcctc cggttttagc atttgctctg ggcactctgg gctttctatt accgtttgat    420
tttaaggagc ataaaaaggt ctttcaggaa gtaatcagct ctagagccaa atgtttgcat    480
agaacacggc tagaatgtca tttgaaaaaa aaggatagca actcatctat tgtgacccat    540
gctatgaatg acatattctt acataggggt aattccccctc atctcactaa cctggacatt    600
ttcattgatg ggaattttt gacaagaacg acagcagatg tgttgcatt ggccactcca      660
acgggttcca cagcatattc attatcagca ggtggatcta ttgtttcccc attagtccct    720
gctatttaa tgacaccaat ttgtcctcgc tctttgtcat ccgaccact gattttgcct      780
cattcatccc acattaggat aaagataggt tccaaattga accaaaaacc agtcaacagt    840
gtggtaaaac tttctgttga tggtattcct caacaggatt tagatgttgg tgatgaaatt     900
tatgttataa atgaggtcgg cactatatac atagatggta ctcagcttcc gacgacaaga    960
aaaactgaaa atgactttaa taattcaaaa aagcctaaaa ggtcagggat ttattgtgtc   1020
gccaagaccg agaatgactg gattagagga atcaatgaac ttttaggatt caattctagc   1080
tttaggctga ccaagagaca gactgataat gattaa                            1116
```

<210> SEQ ID NO 15
<211> LENGTH: 353
<212> TYPE: PRT
<213> ORGANISM: Kluyveromyces maxianus

<400> SEQUENCE: 15

```
Met Thr His Glu Ser Ser Lys Ile Pro Gln Ile Asn Ile Gly Ile
  1               5                  10                  15

Asn Gly Phe Gly Arg Ile Gly Arg Leu Val Leu Arg Ala Ala Leu Ser
                 20                  25                  30

His Pro Glu Ile Lys Val Arg Leu Ile Asn Asn Pro Ser Thr Thr Pro
             35                  40                  45

Glu Tyr Ala Ala Tyr Leu Phe Lys Tyr Asp Ser Thr His Gly Lys Tyr
         50                  55                  60

Pro Gly Glu Val Glu Phe Asp Asp Glu Arg Ile Ile Gln Asn Asp
     65                  70                  75                  80

Glu Val Ser Ala His Ile Pro Leu Ser His Phe Arg Glu Pro Glu Arg
                 85                  90                  95

Ile Pro Trp Ser Ser Tyr Gln Val Asp Tyr Val Ile Ser Thr Gly
            100                 105                 110

Ala Phe Lys Glu Leu Asp Thr Ala Ser Arg His Lys Gly Ile Lys Lys
        115                 120                 125

Val Ile Ile Thr Ala Pro Ser Lys Thr Ala Pro Met Tyr Val Phe Gly
    130                 135                 140
```

```
Val Asn His Lys Lys Tyr Asp Pro Thr Arg Asp Asn Ile Val Ser Asn
145                 150                 155                 160

Ala Ser Cys Thr Thr Asn Cys Leu Ala Pro Leu Val Lys Ala Leu Asp
            165                 170                 175

Asp Glu Phe Gly Ile Glu Glu Ala Leu Met Thr Thr Ile His Ala Thr
        180                 185                 190

Thr Ala Ser Gln Lys Thr Val Asp Gly Thr Ser Gly Gly Lys Asp
    195                 200                 205

Trp Arg Gly Gly Arg Ser Cys Gln Gly Asn Ile Ile Pro Ser Ser Thr
210                 215                 220

Gly Ala Ala Lys Ala Val Gly Lys Ile Leu Pro Glu Leu Lys Asp Ser
225                 230                 235                 240

Ile Thr Gly Met Ser Ile Arg Val Pro Thr Ile Asn Ile Ser Leu Val
                245                 250                 255

Asp Leu Thr Phe Arg Thr Arg Lys Pro Thr Ser Tyr Asp Glu Ile Ile
            260                 265                 270

Ser Ala Leu Glu Leu Lys Ser Arg Arg Glu Met Lys Gly Val Leu Gly
        275                 280                 285

Val Thr Lys Asp Ala Val Val Ser Ser Asp Phe Thr Ser Asp Ser Arg
    290                 295                 300

Ser Ser Ile Val Asp Ala Lys Ala Gly Ile Gln Leu Asn Asp His Phe
305                 310                 315                 320

Phe Lys Val Leu Ser Trp Tyr Asp Asn Glu Tyr Gly Tyr Ser Ser Arg
                325                 330                 335

Val Val Asp Leu Thr Met Tyr Met Ala Gln Arg Asp Phe Glu Ala Gly
            340                 345                 350

Ile

<210> SEQ ID NO 16
<211> LENGTH: 1062
<212> TYPE: DNA
<213> ORGANISM: Kluyveromyces maxianus

<400> SEQUENCE: 16
atgacccacg aatcatcttc caagatacca caaattaaca ttgggattaa cggtttcggt      60
agaatcggta gacttgtgct acgtgccgcc ctttcccatc cagagatcaa ggttagattg     120
attaacaacc catctacaac tccggaatat gccgcttacc tattcaagta cgactctaca     180
catggtaagt accctggcga agtggagttc gatgatgagc gtattataat tcaaaacgac     240
gaggtttcgg cgcacattcc actatcccac ttcagggaac agaacgtat  cccatggtcc     300 tcttaccagg tggattacgt tatcgattcg accggtgctt caaggaatt  ggacaccgca     360 tccagacaca agggcattaa gaaagtcatt attactgcac catccaagac tgccccaatg     420
tacgtgtttg gtgtaaatca caagaagtac gatcctacca gggacaatat cgtctcgaat     480
gcttcttgta ccaccaattg tttggctcct ttggtgaagg ctctagacga cgaatttggt     540
attgaagaag ctttgatgac taccattcat gccacaactg cctcccaaaa gactgtcgac     600
ggtaccagct ctggtggtaa ggactggaga ggtggaagat catgccaagg taacatcatt     660
ccatcatcta ccggtgccgc caaggctgtc ggaaagattt tgcccgagct caaggacagc     720
attacaggta tgtctatcag agtacctacc atcaacattt cgctggttga tttgacattc     780
cggacacgta agccaacctc ttacgacgaa atcatcagtg cgctagaact aaagtcccgt     840
agagaaatga agggcgtgtt gggagtcact aaagacgccg tcgtctcttc tgatttcact     900
```

```
tcagactctc gttcttcaat tgttgatgcc aaagcaggta ttcaactaaa cgatcatttc    960
ttcaaggtcc tttcttggta cgacaatgaa tacggttatt cttcaagagt tgtcgatttg   1020
accatgtaca tggctcaaag agactttgag gcgggtatct aa                      1062
```

<210> SEQ ID NO 17
<211> LENGTH: 505
<212> TYPE: PRT
<213> ORGANISM: Saccharomyces cerevisiae

<400> SEQUENCE: 17

```
Met Ser Glu Gly Pro Val Lys Phe Glu Lys Asn Thr Val Ile Ser Val
 1               5                  10                  15

Phe Gly Ala Ser Gly Asp Leu Ala Lys Lys Lys Thr Phe Pro Ala Leu
            20                  25                  30

Phe Gly Leu Phe Arg Glu Gly Tyr Leu Asp Pro Ser Thr Lys Ile Phe
        35                  40                  45

Gly Tyr Ala Arg Ser Lys Leu Ser Met Glu Glu Asp Leu Lys Ser Arg
    50                  55                  60

Val Leu Pro His Leu Lys Lys Pro His Gly Glu Ala Asp Asp Ser Lys
65                  70                  75                  80

Val Glu Gln Phe Phe Lys Met Val Ser Tyr Ile Ser Gly Asn Tyr Asp
                85                  90                  95

Thr Asp Glu Gly Phe Asp Glu Leu Arg Thr Gln Ile Glu Lys Phe Glu
            100                 105                 110

Lys Ser Ala Asn Val Asp Val Pro His Arg Leu Phe Tyr Leu Ala Leu
        115                 120                 125

Pro Pro Ser Val Phe Leu Thr Val Ala Lys Gln Ile Lys Ser Arg Val
    130                 135                 140

Tyr Ala Glu Asn Gly Ile Thr Arg Val Ile Val Glu Lys Pro Phe Gly
145                 150                 155                 160

His Asp Leu Ala Ser Ala Arg Glu Leu Gln Lys Asn Leu Gly Pro Leu
                165                 170                 175

Phe Lys Glu Glu Glu Leu Tyr Arg Ile Asp His Tyr Leu Gly Lys Glu
            180                 185                 190

Leu Val Lys Asn Leu Leu Val Leu Arg Phe Gly Asn Gln Phe Leu Asn
        195                 200                 205

Ala Ser Trp Asn Arg Asp Asn Ile Gln Ser Val Gln Ile Ser Phe Lys
    210                 215                 220

Glu Arg Phe Gly Thr Glu Gly Arg Gly Gly Tyr Phe Asp Ser Ile Gly
225                 230                 235                 240

Ile Ile Arg Asp Val Met Gln Asn His Leu Leu Gln Ile Met Thr Leu
                245                 250                 255

Leu Thr Met Glu Arg Pro Val Ser Phe Asp Pro Glu Ser Ile Arg Asp
            260                 265                 270

Glu Lys Val Lys Val Leu Lys Ala Val Ala Pro Ile Asp Thr Asp Asp
        275                 280                 285

Val Leu Leu Gly Gln Tyr Gly Lys Ser Glu Asp Gly Ser Lys Pro Ala
    290                 295                 300

Tyr Val Asp Asp Asp Thr Val Asp Lys Asp Ser Lys Cys Val Thr Phe
305                 310                 315                 320

Ala Ala Met Thr Phe Asn Ile Glu Asn Glu Arg Trp Glu Gly Val Pro
                325                 330                 335

Ile Met Met Arg Ala Gly Lys Ala Leu Asn Glu Ser Lys Val Glu Ile
```

```
                340             345             350
Arg Leu Gln Tyr Lys Ala Val Ala Ser Gly Val Phe Lys Asp Ile Pro
            355                 360                 365

Asn Asn Glu Leu Val Ile Arg Val Gln Pro Asp Ala Ala Val Tyr Leu
        370                 375                 380

Lys Phe Asn Ala Lys Thr Pro Gly Leu Ser Asn Ala Thr Gln Val Thr
385                 390                 395                 400

Asp Leu Asn Leu Thr Tyr Ala Ser Arg Tyr Gln Asp Phe Trp Ile Pro
                405                 410                 415

Glu Ala Tyr Glu Val Leu Ile Arg Asp Ala Leu Leu Gly Asp His Ser
            420                 425                 430

Asn Phe Val Arg Asp Asp Glu Leu Asp Ile Ser Trp Gly Ile Phe Thr
        435                 440                 445

Pro Leu Leu Lys His Ile Glu Arg Pro Asp Gly Pro Thr Pro Glu Ile
    450                 455                 460

Tyr Pro Tyr Gly Ser Arg Gly Pro Lys Gly Leu Lys Glu Tyr Met Gln
465                 470                 475                 480

Lys His Lys Tyr Val Met Pro Glu Lys His Pro Tyr Ala Trp Pro Val
                485                 490                 495

Thr Lys Pro Glu Asp Thr Lys Asp Asn
                500                 505

<210> SEQ ID NO 18
<211> LENGTH: 1518
<212> TYPE: DNA
<213> ORGANISM: Saccharomyces cerevisiae

<400> SEQUENCE: 18
atgagtgaag cccccgtcaa attcgaaaaa aataccgtca tatctgtctt tggtgcgtca      60
ggtgatctgg caaagaagaa gactttttcc gccttatttg gcttttttcag agaaggttac    120 cttgatccat ctaccaagat cttcggttat gcccggtcca aattgtccat ggaggaggac    180
ctgaagtccc gtgtcctacc ccacttgaaa aaacctcacg gtgaagccga tgactctaag    240
gtcgaacagt tcttcaagat ggtcagctac atttcgggaa attacgacac agatgaaggc    300
ttcgacgaat taagaacgca gatcgagaaa ttcgagaaaa gtgccaacgt cgatgtccca    360
caccgtctct tctatctggc cttgccgcca agcgtttttt tgacggtggc caagcagatc    420
aagagtcgtg tgtacgcaga gaatggcatc acccgtgtaa tcgtagagaa accttttcggc    480 cacgacctgg cctctgccag ggagctgcaa aaaaacctgg ggcccctctt taaagaagaa    540
gagttgtaca gaattgacca ttacttgggt aaagagttgg tcaagaatct tttagtcttg    600
aggttcggta accagttttt gaatgcctcg tggaatagag acaacattca aagcgttcag    660
atttcgttta aagagaggtt cggcaccgaa ggccgtggcg ctatttcga ctctataggc    720 ataatcagag acgtgatgca gaaccatctg ttacaaatca tgactctctt gactatggaa    780
agaccggtgt cttttgaccc ggaatctatt cgtgacgaaa aggttaaggt tctaaaggcc    840
gtggccccca tcgacacgga cgacgtcctc ttgggccagt acggtaaatc tgaggacggg    900
tctaagcccg cctacgtgga tgatgacact gtagacaagg actctaaatg tgtcactttt    960
gcagcaatga ctttcaacat cgaaaacgag cgttgggagg gcgtccccat catgatgcgt    1020
gccggtaagg ctttgaatga gtccaaggtg gagatcagac tgcagtacaa agcggtcgca    1080
tcgggtgtct tcaagacat tccaaataac gaactggtca tcagagtgca gcccgatgcc    1140
gctgtgtacc taaagtttaa tgctaagacc cctggtctgt caaatgctac ccaagtcaca    1200
```

```
gatctgaatc taacttacgc aagcaggtac caagactttt ggattccaga ggcttacgag    1260
gtgttgataa gagacgccct actgggtgac cattccaact ttgtcagaga tgacgaattg    1320
gatatcagtt ggggcatatt cacccccatta ctgaagcaca tagagcgtcc ggacggtcca    1380
acaccggaaa tttaccccta cggatcaaga ggtccaaagg gattgaagga atatatgcaa    1440
aaacacaagt atgttatgcc cgaaaagcac ccttacgctt ggcccgtgac taagccagaa    1500
gatacgaagg ataattag                                                  1518
```

<210> SEQ ID NO 19
<211> LENGTH: 466
<212> TYPE: PRT
<213> ORGANISM: Escherichia coli

<400> SEQUENCE: 19

```
Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
```

```
                305                 310                 315                 320
Ala Ala Tyr Asp Gln Gly Arg Ile Ala Ala Gln Ala Leu Val Lys Gly
                    325                 330                 335

Glu Ala Thr Ala His Leu Ile Glu Asp Ile Pro Thr Gly Ile Tyr Thr
                    340                 345                 350

Ile Pro Glu Ile Ser Ser Val Gly Lys Thr Glu Gln Leu Thr Ala
                    355                 360                 365

Met Lys Val Pro Tyr Glu Val Gly Arg Ala Gln Phe Lys His Leu Ala
                    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                    405                 410                 415

Ala Ala Glu Ile Ile His Ile Gly Gln Ala Ile Met Glu Gln Lys Gly
                    420                 425                 430

Gly Gly Asn Thr Ile Glu Tyr Phe Val Asn Thr Thr Phe Asn Tyr Pro
                    435                 440                 445

Thr Met Ala Glu Ala Tyr Arg Val Ala Ala Leu Asn Gly Leu Asn Arg
    450                 455                 460

Leu Phe
465

<210> SEQ ID NO 20
<211> LENGTH: 1401
<212> TYPE: DNA
<213> ORGANISM: Escherichia coli

<400> SEQUENCE: 20
atgccacact catatgacta cgacgctatt gtcattggct caggccctgg gggagaaggc      60
gctgcgatgg ggctagtcaa acaaggagcc agagtagcag tgatcgaaag gtatcagaat     120 gtaggggggtg gctgtacaca ctggggtaca atcccatcta aagccttgag acatgctgta    180
tctagaatta tcgaattcaa ccagaaccca ttatactctg atcattccag attacttaga    240
tcctcttttg ctgatatctt gaatcacgca gacaacgtga ttaaccaaca aacgagaatg    300
agacaaggat tttacgaacg taatcactgt gaaattctac aaggtaatgc tagatttgtg    360
gatgagcaca ctttagctct ggattgtcct gatggtagtg tcgaaacatt gacagcagaa    420
aaattcgtta ttgcttgtgg ttctagacca taccatccta ctgacgttga ttttactcat    480
cctagaatat acgactcaga ctctatcttg agtatgcatc atgaaccaag acatgtacta    540
atctacggtg cgggtgtgat tggatgcgaa tatgcttcta tattcagagg catggatgtt    600
aaagttgact taatcaacac tagagatcgt ttactggcct ttttggacca agagatgagt    660
gatagtctgt cttaccattt ttggaattca ggtgttgtta tcaggcacaa tgaagagtac    720
gagaaaatag aaggttgtga tgatggtgtt atcatgcacc ttaagtctgg caaaaagttg    780
aaagctgact gcctattgta tgcaaacggt cgtacaggta atacagattc attggcatta    840
caaaacatcg ggcttgaaac agattctaga ggtcaactaa aggttaattc catgtatcaa    900
accgcccagc tcatgtgata cgccgtgggg gatgtcatag gttacccaag ccttgcatca    960
gcagcatacg atcaaggcag aattgccgca caggctctcg ttaagggtga agccactgcg   1020
cacttaatcg aggatatacc aactggaata tacacgatac agaaatttc atccgtcggc    1080 aaaccgaaac aacaattaac tgcaatgaag gtgcctacg aagttggcag agcacaattc    1140
aaacatttgg ctagggctca gattgtagga atgaacgttg gaacattgaa gattctcttt   1200
```

```
catcgagaaa ctaaggaaat cttgggtatt cattgctttg gagagagagc cgcagagatc    1260
atccatatcg gccaagctat tatggaacaa aaaggtggtg gtaacacaat tgagtacttc    1320
gttaatacaa ctttcaatta ccctaccatg gctgaagcct atagagtcgc agcccttaat    1380
ggactcaata gactgtttta a                                              1401
```

<210> SEQ ID NO 21
<211> LENGTH: 333
<212> TYPE: PRT
<213> ORGANISM: Lactobacillus delbrueckii

<400> SEQUENCE: 21

```
Met Thr Lys Ile Phe Ala Tyr Ala Ile Arg Glu Asp Glu Lys Pro Phe
1               5                   10                  15

Leu Lys Glu Trp Glu Asp Ala His Lys Asp Val Glu Val Glu Tyr Thr
            20                  25                  30

Asp Lys Leu Leu Thr Pro Glu Thr Ala Ala Leu Ala Lys Gly Ala Asp
        35                  40                  45

Gly Val Val Val Tyr Gln Gln Leu Asp Tyr Thr Ala Glu Thr Leu Gln
    50                  55                  60

Ala Leu Ala Asp Asn Gly Ile Thr Lys Met Ser Leu Arg Asn Val Gly
65                  70                  75                  80

Val Asp Asn Ile Asp Met Ala Lys Ala Lys Glu Leu Gly Phe Gln Ile
                85                  90                  95

Thr Asn Val Pro Val Tyr Ser Pro Asn Ala Ile Ala Glu His Ala Ala
            100                 105                 110

Ile Gln Ala Ala Arg Ile Leu Arg Gln Ala Lys Ala Met Asp Glu Lys
        115                 120                 125

Val Ala Arg His Asp Leu Arg Trp Ala Pro Thr Ile Gly Arg Glu Val
    130                 135                 140

Arg Asp Gln Val Val Gly Val Gly Thr Gly His Ile Gly Gln Val
145                 150                 155                 160

Phe Met Gln Ile Met Glu Gly Phe Gly Ala Lys Val Ile Ala Tyr Ala
                165                 170                 175

Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Lys Ser Ile Ala Lys
    210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
            260                 265                 270

Trp Glu Gly Lys Glu Phe Pro Asp Ala Arg Leu Ala Asp Leu Ile Ala
        275                 280                 285

Arg Pro Asn Val Leu Val Thr Pro His Thr Ala Phe Tyr Thr Thr His
    290                 295                 300

Ala Val Arg Asn Met Val Ile Lys Ala Phe Asp Asn Asn Leu Glu Leu
305                 310                 315                 320

Ile Glu Gly Lys Glu Ala Glu Thr Pro Val Lys Val Gly
                325                 330
```

<210> SEQ ID NO 22
<211> LENGTH: 1002
<212> TYPE: DNA
<213> ORGANISM: Lactobacillus delbrueckii sbusp. Bulgaricus

<400> SEQUENCE: 22

```
atgactaaaa tcttcgctta cgctataaga gaggacgaaa agccattttt gaaagagtgg      60
gaggatgcgc ataaagatgt tgaagttgag tacacggata aacttttaac tcctgaaact     120
gctgcattgg caagggtgc agacggcgta gtagtatatc aacagcttga ttatacagct     180
gaaaccctcc aagctctcgc tgataatggg attacaaaaa tgtctttgcg taatgtaggt     240
gttgacaaca tagacatggc caaagcaaag gaactaggct ttcaaatcac aaatgtgcct     300
gtgtactcac caaatgctat cgctgaacac gctgccatac aagccgctag aatcttaaga     360
caggcgaagg ctatggatga aaaggttgca agacatgatc taagatgggc tcctactatc     420
ggtagggaag taagagatca agttgtcggt gtggtgggaa caggacatat tggccaagtt     480
ttcatgcaga ttatggaagg attcggggca aaagtcattg cctacgctat ttttcgaaac     540
cctgagctgg agaaaaaggg ttactacgtt gattctctgg atgacctata caaacaagca     600
gatgttattt ctcttcatgt gccagatgtc ccagcaaatg tccacatgat caacgacaaa     660
tcaattgcca agatgaaaca agatgtcgta atcgttaatg tgagtagagg gcctttggtt     720
gacaccgacg ctgttataag gggtttggat ccggtaaag tatttggata tgcgatggat     780
gtttacgaag gtgaagtcgg tgtctttaac gaagattggg aaggcaaaga gttcccagac     840
gcaagattag ccgatttgat cgcaagacca aatgttttag taacaccaca cactgccttc     900
tatacaacac atgccgtgag aaacatggtt attaaggcat tgataataa cttagaattg     960
atcgaaggca aggaagctga aactccagtt aaggtcggtt aa                       1002
```

<210> SEQ ID NO 23
<211> LENGTH: 333
<212> TYPE: PRT
<213> ORGANISM: Artificial Sequence
<220> FEATURE:
<223> OTHER INFORMATION: Synthetic Lactobacillus delbrueckii subsp. bulgaicus

<400> SEQUENCE: 23

```
Met Thr Lys Ile Phe Ala Tyr Ala Ile Arg Glu Asp Glu Lys Pro Phe
  1               5                  10                  15

Leu Lys Glu Trp Glu Asp Ala His Lys Asp Val Glu Val Glu Tyr Thr
             20                  25                  30

Asp Lys Leu Leu Thr Pro Glu Thr Ala Ala Leu Ala Lys Gly Ala Asp
         35                  40                  45

Gly Val Val Val Tyr Gln Gln Leu Asp Tyr Thr Ala Glu Thr Leu Gln
     50                  55                  60

Ala Leu Ala Asp Asn Gly Ile Thr Lys Met Ser Leu Arg Asn Val Gly
 65                  70                  75                  80

Val Asp Asn Ile Asp Met Ala Lys Ala Lys Glu Leu Gly Phe Gln Ile
                 85                  90                  95

Thr Asn Val Pro Val Tyr Ser Pro Asn Ala Ile Ala Glu His Ala Ala
            100                 105                 110

Ile Gln Ala Ala Arg Ile Leu Arg Gln Ala Lys Ala Met Asp Glu Lys
        115                 120                 125

Val Ala Arg His Asp Leu Arg Trp Ala Pro Thr Ile Gly Arg Glu Val
```

```
                        130                 135                 140
Arg Asp Gln Val Val Gly Val Val Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
                180                 185                 190

Leu Asp Asp Leu Tyr Lys Gln Ala Asp Val Ile Ser Leu His Val Pro
                195                 200                 205

Asp Val Pro Ala Asn Val His Met Ile Asn Asp Lys Ser Ile Ala Lys
            210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
                260                 265                 270

Trp Glu Gly Lys Glu Phe Pro Asp Ala Arg Leu Ala Asp Leu Ile Ala
            275                 280                 285

Arg Pro Asn Val Leu Val Thr Pro His Thr Ala Phe Tyr Thr Thr His
290                 295                 300

Ala Val Arg Asn Met Val Ile Lys Ala Phe Asp Asn Asn Leu Glu Leu
305                 310                 315                 320

Ile Glu Gly Lys Glu Ala Glu Thr Pro Val Lys Val Gly
                325                 330

<210> SEQ ID NO 24
<211> LENGTH: 1002
<212> TYPE: DNA
<213> ORGANISM: Lactobacillus delbrueckii subsp. bulgaicus

<400> SEQUENCE: 24
atgactaaaa tcttcgctta cgctataaga gaggacgaaa agccattttt gaaagagtgg      60
gaggatgcgc ataaagatgt tgaagttgag tacacggata aacttttaac tcctgaaact     120
gctgcattgg caaagggtgc agacggcgta gtagtatatc aacagcttga ttatacagct     180
gaaacccctc caagctctcgc tgataatggg attacaaaaa tgtctttgcg taatgtaggt     240
gttgacaaca tagacatggc caaagcaaag gaactaggct tcaaatcac aaatgtgcct     300
gtgtactcac caaatgctat cgctgaacac gctgccatac aagccgctag aatcttaaga     360
caggcgaagg ctatggatga aaaggttgca agacatgatc taagatgggc tcctactatc     420
ggtagggaag taagagatca agttgtcggt gtggtgggaa caggacatat tggccaagtt     480
ttcatgcaga ttatggaagg attcggggca aaagtcattg cctacgacat ttttcgaaac     540
cctgagctgg agaaaaaggg ttactacgtt gattctctgg atgacctata caaacaagca     600
gatgttattt ctcttcatgt gccagatgtc ccagcaaatg tccacatgat caacgacaaa     660
tcaattgcca agatgaaaca agatgtcgta atcgttaatg tgagtagagg gcctttggtt     720
gacaccgacg ctgttataag gggtttggat tccggtaaag tatttggata tgcgatggat     780
gtttacgaag gtgaagtcgg tgtctttaac gaagattggg aaggcaaaga gttcccagac     840
gcaagattag ccgatttgat cgcaagacca aatgttttag taacaccaca cactgccttc     900
tatacaacac atgccgtgag aaacatggtt attaaggcat tgataataa cttagaattg     960
atcgaaggca aggaagctga aactccagtt aaggtcggtt aa                      1002
```

<210> SEQ ID NO 25
<211> LENGTH: 332
<212> TYPE: PRT
<213> ORGANISM: Bos Taurus

<400> SEQUENCE: 25

Met Ala Thr Leu Lys Asp Gln Leu Ile Gln Asn Leu Leu Lys Glu Glu
1               5                   10                  15

His Val Pro Gln Asn Lys Ile Thr Ile Val Gly Val Gly Ala Val Gly
            20                  25                  30

Met Ala Cys Ala Ile Ser Ile Leu Met Lys Asp Leu Ala Asp Glu Val
        35                  40                  45

Ala Leu Val Asp Val Met Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330

<210> SEQ ID NO 26
<211> LENGTH: 332
<212> TYPE: PRT
<213> ORGANISM: Pelodiscus sinensis japonicus

<400> SEQUENCE: 26

Met Ser Val Lys Glu Leu Leu Ile Gln Asn Val His Lys Glu His
1               5                   10                  15

Ser His Ala His Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Arg Gly Glu Met Leu Asp
        50                  55                  60

Leu Gln His Gly Ser Leu Phe Leu Arg Thr Pro Lys Ile Val Ser Gly
65                  70                  75                  80

Lys Asp Tyr Ser Val Thr Ala His Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
            165                 170                 175

Lys Leu Gly Ile His Ser Leu Ser Cys His Gly Trp Ile Ile Gly Glu
        180                 185                 190

His Gly Asp Ser Ser Val Pro Val Trp Ser Gly Val Asn Val Ala Gly
    195                 200                 205

Val Ser Leu Lys Ala Leu Tyr Pro Asp Leu Gly Thr Asp Ala Asp Lys
210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
            245                 250                 255

Ala Asp Leu Ala Glu Thr Val Met Lys Asn Leu Arg Arg Val His Pro
        260                 265                 270

Ile Ser Thr Met Val Lys Gly Met Tyr Gly Val Ser Ser Asp Val Phe
    275                 280                 285

Leu Ser Val Pro Cys Val Leu Gly Tyr Ala Gly Ile Thr Asp Val Val
290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
            325                 330

<210> SEQ ID NO 27
<211> LENGTH: 332
<212> TYPE: PRT
<213> ORGANISM: Ornithorhynchus anatinus

<400> SEQUENCE: 27

Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu

```
            35                 40                  45
Ala Leu Val Asp Val Ile Glu Asp Lys Leu Lys Gly Glu Met Met Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Pro Asn Val Val Lys Tyr Ser
            115                 120                 125

Pro Asn Cys Lys Leu Leu Val Val Ser Asn Pro Val Asp Ile Leu Thr
        130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Asp Leu Gly Thr Asp Ala Asp Lys
        210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
        290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 28
<211> LENGTH: 332
<212> TYPE: PRT
<213> ORGANISM: Tursiops truncatus

<400> SEQUENCE: 28

Met Ala Thr Val Lys Asp Gln Leu Ile Gln Asn Leu Leu Lys Glu Glu
 1               5                  10                  15

His Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
         50                  55                  60

Leu Gln His Gly Ser Leu Phe Leu Arg Thr Pro Lys Ile Val Ser Gly
 65                  70                  75                  80
```

```
Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330

<210> SEQ ID NO 29
<211> LENGTH: 332
<212> TYPE: PRT
<213> ORGANISM: Rattus norvegicus

<400> SEQUENCE: 29

Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125
```

```
Pro Gln Cys Lys Leu Leu Ile Val Ser Asn Pro Val Asp Ile Leu Thr
            130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 30
<211> LENGTH: 999
<212> TYPE: DNA
<213> ORGANISM: Bos Taurus

<400> SEQUENCE: 30
atggcaacat taaaagatca actaatccag aatttgttga agaggagca tgttccacaa      60 aacaaaatca caatcgtcgg cgtaggtgca gtaggtatgg cttgtgccat atccatcttg    120
atgaaagact tagctgatga ggtcgcgctg gttgatgtaa tggaggacaa acttaaagga    180
gaaatgatgg atcttcaaca tggttcactc tttttgagaa ctcctaaaat tgtatccggg    240
aaagattata acgttaccgc caattctaga cttgttataa tcacggctgg tgcaagacaa    300
caggaaggcg aatcaagact taacttagtt cagagaaacg taaacatttt caagtttatc    360
atcccaaata ttgtaaaata ctccccaaat tgcaagttgc tggttgtttc aaatcctgtt    420
gacatattga cttacgttgc ttggaagatt tcaggtttcc caaagaatag agtaatcgga    480
tctggttgca atctcgattc tgctcgtttt aggtatctga tgggtgaaag attaggggtt    540
catccattga gttgtcacgg atggattcta ggtgaacatg gagatagttc tgtgcctgtt    600
tggtcaggtg tcaacgtagc aggtgtctct ttgaaaaatc tacacccaga actaggaaca    660
gatgccgaca ggaacaatg gaaggccgtc acaaacaag tggtggattc tgcctacgaa    720
gtcatcaaat tgaagggcta cacatcttgg gcaattggct tatccgtcgc tgatctggct    780
gaatcaataa tgaaaaacct ccgtagagtg catcctataa gtactatgat taagggttta    840
tacgggatca aggaagatgt tttttctatct gtgccatgta ttttgggcca aaatggaatt    900
tctgacgttg ttaaagtgac acttactcat gaagaggaag cgtgtttgaa aaagagcgca    960
```
gacaccttat ggggcatcca aaaggaatta caattctaa                    999

<210> SEQ ID NO 31
<211> LENGTH: 563
<212> TYPE: PRT
<213> ORGANISM: Saccharomyces cerevisiae

<400> SEQUENCE: 31

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
                515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln

<210> SEQ ID NO 32
<211> LENGTH: 1692
<212> TYPE: DNA
<213> ORGANISM: Saccharomyces cerevisiae

<400> SEQUENCE: 32

```
atgtctgaaa ttactttggg taaatatttg ttcgaaagat taaagcaagt caacgttaac    60
accgttttcg gtttgccagg tgacttcaac ttgtccttgt tggacaagat ctacgaagtt   120
gaaggtatga gatgggctgg taacgccaac gaattgaacg ctgcttacgc cgctgatggt   180
tacgctcgta tcaagggtat gtcttgtatc atcaccacct tcggtgtcgg tgaattgtct   240
gctttgaacg gtattgccgg ttcttacgct gaacacgtcg gtgttttgca cgttgttggt   300
gtcccatcca tctctgctca agctaagcaa ttgttgttgc accacacctt gggtaacggt   360
gacttcactg ttttccacag aatgtctgcc aacatttctg aaaccactgc tatgatcact   420
gacattgcta ccgccccagc tgaaattgac agatgtatca gaaccactta cgtcaccccaa   480
agaccagtct acttaggttt gccagctaac ttggtcgact tgaacgtccc agctaagttg   540
ttgcaaactc caattgacat gtctttgaag ccaaacgatg ctgaatccga aaaggaagtc   600
attgacacca tcttggcttt ggtcaaggat gctaagaacc cagttatctt ggctgatgct   660
tgttgttcca gacacgacgt caaggctgaa actaagaagt tgattgactt gactcaattc   720
ccagctttcg tcaccccaat gggtaagggt tccattgacg aacaacaccc aagatacggt   780
ggtgtttacg tcggtaccct gtccaagcca gaagttaagg aagccgttga atctgctgac   840
ttgattttgt ctgtcggtgc ttgtgttgtct gatttcaaca ccggttcttt ctcttactct   900
tacaagacca agaacattgt cgaattccac tccgaccaca tgaagatcag aaacgccact   960
```

-continued

```
ttcccaggtg tccaaatgaa attcgttttg caaaagttgt tgaccactat tgctgacgcc     1020
gctaagggtt acaagccagt tgctgtccca gctagaactc cagctaacgc tgctgtccca     1080
gcttctaccc cattgaagca agaatggatg tggaaccaat gggtaactt cttgcaagaa      1140 ggtgatgttg tcattgctga accggtacc tccgctttcg gtatcaacca aaccactttc      1200
ccaaacaaca cctacggtat ctctcaagtc ttatggggtt ccattggttt caccactggt     1260
gctaccttgg gtgctgcttt cgctgctgaa gaaattgatc aaagaagag agttatctta     1320 ttcattggtg acggttcttt gcaattgact gttcaagaaa tctccaccat gatcagatgg     1380
ggcttgaagc atacttgtt cgtcttgaac aacgatggtt acaccattga aaagttgatt     1440
cacggtccaa aggctcaata acgaaatt caaggttggg accacctatc cttgttgcca      1500
actttcggtg ctaaggacta tgaaacccac agagtcgcta ccaccggtga atgggacaag    1560
ttgacccaag acaagtcttt caacgacaac tctaagatca gaatgattga aatcatgttg    1620
ccagtcttcg atgctccaca aaacttggtt gaacaagcta agttgactgc tgctaccaac    1680
gctaagcaat aa                                                          1692
```

<210> SEQ ID NO 33
<211> LENGTH: 563
<212> TYPE: PRT
<213> ORGANISM: Saccharomyces cerevisiae

<400> SEQUENCE: 33

```
Met Ser Glu Ile Thr Leu Gly Lys Tyr Leu Phe Glu Arg Leu Lys Gln
  1               5                  10                  15

Val Asn Val Asn Thr Ile Phe Gly Leu Pro Gly Asp Phe Asn Leu Ser
                 20                  25                  30

Leu Leu Asp Lys Ile Tyr Glu Val Asp Gly Leu Arg Trp Ala Gly Asn
             35                  40                  45

Ala Asn Glu Leu Asn Ala Ala Tyr Ala Ala Asp Gly Tyr Ala Arg Ile
         50                  55                  60

Lys Gly Leu Ser Val Leu Val Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ser Met Ile Thr Asp Ile Ala Thr
        130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240
```

```
Pro Ala Phe Val Thr Pro Leu Gly Lys Gly Ser Ile Asp Glu Gln His
            245                 250                 255

Pro Arg Tyr Gly Gly Val Tyr Val Gly Thr Leu Ser Lys Pro Asp Val
        260                 265                 270

Lys Gln Ala Val Glu Ser Ala Asp Leu Ile Leu Ser Val Gly Ala Leu
    275                 280                 285

Leu Ser Asp Phe Asn Thr Gly Ser Phe Ser Tyr Ser Tyr Lys Thr Lys
290                 295                 300

Asn Val Val Glu Phe His Ser Asp Tyr Val Lys Val Lys Asn Ala Thr
305                 310                 315                 320

Phe Pro Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 34
<211> LENGTH: 1693
<212> TYPE: DNA
<213> ORGANISM: Saccharomyces cerevisiae

<400> SEQUENCE: 34
atgtctgaaa ttactcttgg aaaatactta tttgaaagat tgaagcaagt taatgttaac      60 accattttg ggctaccagg cgacttcaac ttgtccctat ggacaagat ttacgaggta       120 gatggattga gatgggctgg taatgcaaat gagctgaacg ccgccatgc cgccgatggt      180 tacgcacgca tcaaggggttt atctgtgctg gtaactactt ttggcgtagg tgaattatct    240
gccttgaatg gtattgcagg atcgtatgca gaacacgtcg gtgtactgca tgttgttggt    300
```

```
gtcccctcta tctccgctca ggctaagcaa ttgttgttgc atcataccct gggtaacggt    360
gattttaccg tttttcacag gatgtccgcc aatatctcag aaactacatc aatgattaca    420
gacattgcta cagccccttc agaaatcgat aggttgatca ggacaacatt tataacacaa    480
aggcctagct acttggggtt gccagcgaat tggtagatc taaaggttcc tggttctctt    540
ttggaaaaac cgattgatct atcattaaaa cctaacgatc ctgaagctga aaaggaagtt    600
attgataccg tactagaatt gatccagaat tcgaaaaacc ctgtcatact atcggatgcc    660
tgtgcttcta ggcacaacgt taaaaaggaa acccagaagt taattgattt gacgcaattc    720
ccagcttttg tgcaccctt aggtaaaggg tcaatagatg aacagcatcc cagatatggc    780
ggtgtttatg tgggaacgct gtccaaacca gacgtgaaac aggccgttga gtcggctgat    840
ttgatccttt cggtcggtgc tttgctctct gattttaaca caggttcgtt ttcctactcc    900
tacaagacta aaaatgtagt ggagtttcat tccgattacg taaaggtgaa gaacgctacg    960
ttcccccggcg tacaaatgaa atttgcacta caaaacttac tgaaggttat tcccgatgtt   1020
gttaagggct acaagagcgt tcccgtacca accaaaactc ccgcaaacaa aggtgtacct   1080
gctagcacgc ccttgaaaca agagtggttg tggaacgaat tgtccaagtt cttgcaagaa   1140
ggtgatgtta tcatttccga gaccggcacg tctgccttcg gtatcaatca aactatcttt   1200
cctaaggacg cctacggtat ctcgcaagtg ttgtgggggt ctatcggttt tacaacagga   1260
gcaactttag gtgctgcctt tgccgctgag gagattgacc ccaacaagag agtcatctta   1320
ttcataggtg acgggtcttt tgcagttaacc gtccaagaaa tctccaccat gatcagatgg   1380
gggttaaagc cgtatctttt tgtccttaac aacgacggct acactatcga aaagctgatt   1440
catgggcctc acgcagagta caacgaaatc cagacctggg atcacctcgc cctgttgccc   1500
gcatttggtg cgaaaaagta cgaaaatcac aagatcgcca ctacgggcga gtgggacgcc   1560
ttaaccactg attcagagtt ccagaaaaac tcggtgatca gactaattga actgaaactg   1620
cccgtctttg atgctccgga aagtttgatc aaacaagcgc aattgactgc cgctacaaat   1680
gccaaacaat aaa                                                        1693

<210> SEQ ID NO 35
<211> LENGTH: 391
<212> TYPE: PRT
<213> ORGANISM: Saccharomyces cerevisiae

<400> SEQUENCE: 35

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
```

|   | 115 |   |   | 120 |   |   | 125 |   |
|---|---|---|---|---|---|---|---|---|

Phe Leu Pro Arg Ile Cys Ser Gln Leu Lys Gly His Val Asp Ser His
 130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
                195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
                275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
                370                 375                 380

Glu Leu Asp Leu His Glu Asp
385                 390

<210> SEQ ID NO 36
<211> LENGTH: 1176
<212> TYPE: DNA
<213> ORGANISM: Saccharomyces cerevisiae

<400> SEQUENCE: 36

```
atgtctgctg ctgctgatag attaaactta acttccggcc acttgaatgc tggtagaaag     60
agaagttcct cttctgtttc tttgaaggct gccgaaaagc ctttcaaggt tactgtgatt    120
ggatctggta actggggtac tactattgcc aaggtggttg ccgaaaattg taagggatac    180
ccagaagttt cgctccaat agtacaaatg tgggtgttcg aagaagagat caatggtgaa    240
aaattgactg aaatcataaa tactagacat caaaacgtga atacttgcc tggcatcact    300 ctacccgaca atttggttgc taatccagac ttgattgatt cagtcaagga tgtcgacatc    360
atcgttttca acattccaca tcaatttttg ccccgtatct gtagccaatt gaaaggtcat    420
gttgattcac acgtcagagc tatctcctgt ctaaagggtt ttgaagttgg tgctaaaggt    480
gtccaattgc tatcctctta catcactgag gaactaggta ttcaatgtgg tgctctatct    540
```

-continued

```
ggtgctaaca ttgccaccga agtcgctcaa gaacactggt ctgaaacaac agttgcttac      600
cacattccaa aggatttcag aggcgagggc aaggacgtcg accataaggt tctaaaggcc      660
ttgttccaca gaccttactt ccacgttagt gtcatcgaag atgttgctgg tatctccatc      720
tgtggtgctt tgaagaacgt tgttgcctta ggttgtggtt tcgtcgaagg tctaggctgg      780
ggtaacaacg cttctgctgc catccaaaga gtcggtttgg gtgagatcat cagattcggt      840
caaatgtttt tcccagaatc tagagaagaa acatactacc aagagtctgc tggtgttgct      900
gatttgatca ccacctgcgc tggtggtaga aacgtcaagg ttgctaggct aatggctact      960
tctggtaagg acgcctggga atgtgaaaag gagttgttga atggccaatc cgctcaaggt     1020
ttaattacct gcaaagaagt tcacgaatgg ttggaaacat gtggctctgt cgaagacttc     1080
ccattatttg aagccgtata ccaaatcgtt tacaacaact acccaatgaa gaacctgccg     1140
gacatgattg aagaattaga tctacatgaa gattag                               1176
```

<210> SEQ ID NO 37
<211> LENGTH: 587
<212> TYPE: PRT
<213> ORGANISM: Saccharomyces cerevisiae

<400> SEQUENCE: 37

```
Met Leu Trp Lys Arg Thr Cys Thr Arg Leu Ile Lys Pro Ile Ala Gln
 1               5                  10                  15

Pro Arg Gly Arg Leu Val Arg Arg Ser Cys Tyr Arg Tyr Ala Ser Thr
            20                  25                  30

Gly Thr Gly Ser Thr Asp Ser Ser Gln Trp Leu Lys Tyr Ser Val
        35                  40                  45

Ile Ala Ser Ser Ala Thr Leu Phe Gly Tyr Leu Phe Ala Lys Asn Leu
    50                  55                  60

Tyr Ser Arg Glu Thr Lys Glu Asp Leu Ile Glu Lys Leu Glu Met Val
65                  70                  75                  80

Lys Lys Ile Asp Pro Val Asn Ser Thr Leu Lys Leu Ser Ser Leu Asp
                85                  90                  95

Ser Pro Asp Tyr Leu His Asp Pro Val Lys Ile Asp Lys Val Val Glu
            100                 105                 110

Asp Leu Lys Gln Val Leu Gly Asn Lys Pro Glu Asn Tyr Ser Asp Ala
        115                 120                 125

Lys Ser Asp Leu Asp Ala His Ser Asp Thr Tyr Phe Asn Thr His His
    130                 135                 140

Pro Ser Pro Glu Gln Arg Pro Arg Ile Ile Leu Phe Pro His Thr Thr
145                 150                 155                 160

Glu Glu Val Ser Lys Ile Leu Lys Ile Cys His Asp Asn Asn Met Pro
                165                 170                 175

Val Val Pro Phe Ser Gly Gly Thr Ser Leu Glu Gly His Phe Leu Pro
            180                 185                 190

Thr Arg Ile Gly Asp Thr Ile Thr Val Asp Leu Ser Lys Phe Met Asn
        195                 200                 205

Asn Val Val Lys Phe Asp Lys Leu Asp Leu Asp Ile Thr Val Gln Ala
    210                 215                 220

Gly Leu Pro Trp Glu Asp Leu Asn Asp Tyr Leu Ser Asp His Gly Leu
225                 230                 235                 240

Met Phe Gly Cys Asp Pro Gly Pro Gly Ala Gln Ile Gly Gly Cys Ile
                245                 250                 255

Ala Asn Ser Cys Ser Gly Thr Asn Ala Tyr Arg Tyr Gly Thr Met Lys
```

Glu Asn Ile Ile Asn Met Thr Ile Val Leu Pro Asp Gly Thr Ile Val
            260                 265                 270

Lys Thr Lys Lys Arg Pro Arg Lys Ser Ser Ala Gly Tyr Asn Leu Asn
275                 280                 285

Gly Leu Phe Val Gly Ser Glu Gly Thr Leu Gly Ile Val Thr Glu Ala
290                 295                 300

Thr Val Lys Cys His Val Lys Pro Lys Ala Glu Thr Val Ala Val Val
305                 310                 315                 320

Ser Phe Asp Thr Ile Lys Asp Ala Ala Ala Cys Ala Ser Asn Leu Thr
            325                 330                 335

Gln Ser Gly Ile His Leu Asn Ala Met Glu Leu Leu Asp Glu Asn Met
            340                 345                 350

Met Lys Leu Ile Asn Ala Ser Glu Ser Thr Asp Arg Cys Asp Trp Val
        355                 360                 365

Glu Lys Pro Thr Met Phe Phe Lys Ile Gly Gly Arg Ser Pro Asn Ile
370                 375                 380

Val Asn Ala Leu Val Asp Glu Val Lys Ala Val Ala Gln Leu Asn His
385                 390                 395                 400

Cys Asn Ser Phe Gln Phe Ala Lys Asp Asp Glu Lys Leu Glu Leu
            405                 410                 415

Trp Glu Ala Arg Lys Val Ala Leu Trp Ser Val Leu Asp Ala Asp Lys
        420                 425                 430

Ser Lys Asp Lys Ser Ala Lys Ile Trp Thr Thr Asp Val Ala Val Pro
    435                 440                 445

Val Ser Gln Phe Asp Lys Val Ile His Glu Thr Lys Lys Asp Met Gln
450                 455                 460

Ala Ser Lys Leu Ile Asn Ala Ile Val Gly His Ala Gly Asp Gly Asn
465                 470                 475                 480

Phe His Ala Phe Ile Val Tyr Arg Thr Pro Glu Glu His Glu Thr Cys
            485                 490                 495

Ser Gln Leu Val Asp Arg Met Val Lys Arg Ala Leu Asn Ala Glu Gly
        500                 505                 510

Thr Cys Thr Gly Glu His Gly Val Gly Ile Gly Lys Arg Glu Tyr Leu
    515                 520                 525

Leu Glu Glu Leu Gly Glu Ala Pro Val Asp Leu Met Arg Lys Ile Lys
530                 535                 540

Leu Ala Ile Asp Pro Lys Arg Ile Met Asn Pro Asp Lys Ile Phe Lys
545                 550                 555                 560

Thr Asp Pro Asn Glu Pro Ala Asn Asp Tyr Arg
            565                 570                 575

<210> SEQ ID NO 38
<211> LENGTH: 1764
<212> TYPE: DNA
<213> ORGANISM: Saccharomyces cerevisiae

<400> SEQUENCE: 38
atgttgtgga agcgtacttg cacaaggcta ataaagccta ttgcacaacc tagaggaagg     60
ctggtgagaa gatcatgcta cagatacgcc tcaacaggca caggcagcac cgacagcagc    120
agccagtggt taaatactc tgtcatcgcc tcttcagcta ctctattcgg ttatttgttc    180
gctaagaacc tctattctag ggagactaag gaagatttga tagagaagct ggaaatggtc    240
aaaaagatcg acccagtaaa ttctacgtta aagctgtcct cattggactc accagactat    300

```
ttgcacgacc cggttaagat cgataaggtt gttgaggacc tgaagcaggt gctgggaaac    360
aagcctgaaa actactctga tgcgaaatcc gatttggacg cccattcaga tacctacttc    420
aacacgcatc accctctcc cgagcaaaga cctaggatta tattattccc tcatactacc    480
gaagaagttt ccaaaatttt gaaaatatgt cacgataaca acatgccagt tgtacccttc    540
tcgggcggaa cgtccttgga ggggcacttc ctgcctacaa gaattggaga taccataacc    600
gtagacctgt ccaagtttat gaataacgtc gtaaaatttg acaagctgga cctggacatc    660
accgtgcagg ccggtctacc ctgggaggat ttgaatgact atttgagcga ccacggtttg    720
atgtttggct gtgaccctgg tccaggtgca cagattggtg gttgcattgc taattcttgt    780
tcaggaacca acgcctaccg ttacggtacc atgaaggaga atattataaa catgactata    840
gtgttgccgg acgggaccat tgtcaagacg aagaaaagac ccagaaagtc gagcgctggc    900
tataacttaa atggtttatt tgtgggaagt gaaggtacct aggtattgt tactgaagct     960 actgtcaagt gtcatgtcaa gcccaaagct gaaactgttg cggtggtatc ctttgatact   1020
atcaaggatg cggccgcatg tgcttctaat ctgactcaga gtggtattca tttgaacgcc   1080
atggagttac tggatgaaaa tatgatgaag ttgatcaacg catctgaatc cacggacaga   1140
tgtgattggg tagagaaacc aactatgttt ttcaagattg gtgggagatc tcccaacatt   1200
gtcaatgctc ttgtggatga agttaaggct gtcgcccagt taaatcactg caacagtttt   1260
cagtttgcta aagatgatga cgaaaaattg gaattatggg aagctagaaa ggtcgcgcta   1320
tggtctgtgc tagacgctga taagagcaaa gacaaatcag ctaaaatttg gacaactgat   1380
gtagctgttc ctgtgtcgca gttcgacaag gttattcacg aaactaaaaa ggacatgcaa   1440
gctagtaagc tgatcaacgc cattgttggt catgcaggtg atggtaactt ccatgcattc   1500
atcgtctaca gaacccctga agaacacgaa acctgtagcc aacttgttga cagaatggtc   1560
aagagagcac tgaacgcaga aggcacttgc acgggtgaac acggtgttgg tattggtaaa   1620
agagagtact tgctcgaaga attaggtgaa gcacccgtcg atttgatgag aaagattaag   1680
ctagctattg acccaaagag aatcatgaac ccggacaaaa tctttaaaac tgatccaaac   1740
gagcccgcta atgattacag gtga                                          1764
```

<210> SEQ ID NO 39
<211> LENGTH: 591
<212> TYPE: PRT
<213> ORGANISM: Saccharomyces cerevisiae

<400> SEQUENCE: 39

Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

```
Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
                180                 185                 190

Lys Ser Leu Leu Pro Pro Leu Asp Asn Ile Ile Asn Leu Tyr Asp Phe
                195                 200                 205

Glu Tyr Leu Ala Ser Gln Thr Leu Thr Lys Gln Ala Trp Ala Tyr Tyr
        210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
                260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
        290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
                340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
        370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
                420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
                500                 505                 510

Arg Pro Phe Leu Tyr Ala Asn Ser Cys Tyr Gly Arg Asn Gly Val Glu
        515                 520                 525
```

Lys Ala Ile Glu Ile Leu Arg Asp Glu Ile Glu Met Ser Met Arg Leu
            530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590

<210> SEQ ID NO 40
<211> LENGTH: 1776
<212> TYPE: DNA
<213> ORGANISM: Saccharomyces cerevisiae

<400> SEQUENCE: 40

```
atgctaaaat acaaaccttt actaaaaatc tcgaagaact gtgaggctgc tatcctcaga      60
gcgtctaaga ctagattgaa cacaatccgc gcgtacggtt ctaccgttcc aaaatccaag     120
tcgttcgaac aagactcaag aaaacgcaca cagtcatgga ctgccttgag agtcggtgca     180
attctagccg ctactagttc cgtggcgtat ctaaactggc ataatggcca aatagacaac     240
gagccgaaac tggatatgaa taaacaaaag atttcgcccg ctgaagttgc caagcataac     300
aagcccgatg attgttgggt tgtgatcaat ggttacgtat acgacttaac gcgattccta     360
ccaaatcatc caggtgggca ggatgttatc aagtttaacg ccgggaaaga tgtcactgct     420 attttttgaac cactacatgc tcctaatgtc atcgataagt atatagctcc cgagaaaaaa     480
ttgggtcccc ttcaaggatc catgcctcct gaacttgtct gtcctcctta tgctcctggt     540
gaaactaagg aagatatcgc tagaaaagaa caactaaaat cgctgctacc tcctctagat     600
aatattatta acctttacga ctttgaatac ttggcctctc aaactttgac taaacaagcg     660
tgggcctact attcctccgg tgctaacgac gaagttactc acagagaaaa ccataatgct     720
tatcatagga ttttttttcaa accaaagatc cttgtagatg tacgcaaagt agacatttca     780
actgacatgt tgggttctca tgtggatgtt cccttctacg tgtctgctac agctttgtgt     840
aaactgggaa acccccttaga aggtgaaaaa gatgtcgcca gaggttgtgg ccaaggtgtg     900
acaaaagtcc cacaaatgat atctactttg gcttcatgtt cccctgagga aattattgaa     960
gcagcaccct ctgataaaca aattcaatgg taccaactat atgttaactc tgatagaaag    1020
atcactgatg atttggttaa aaatgtagaa aagctgggtg taaaggcatt atttgtcact    1080
gtggatgctc caagtttagg tcaaagagaa aaagatatga gctgaaatt ttccaataca    1140 aaggctggtc caaaagcgat gaagaaaact aatgtagaag aatctcaagg tgcttcgaga    1200
gcgttatcaa agtttattga cccctctttg acttggaaag atatagaaga gttgaagaaa    1260
aagacaaaac tacctattgt tatcaaaggt gttcaacgta ccgaagatgt tatcaaagca    1320
gcagaaatcg gtgtaagtgg ggtggttcta tccaatcatg gtggtagaca attagatttt    1380
tcaagggctc ccattgaagt cctggctgaa accatgccaa tcctggaaca acgtaacttg    1440
aaggataagt tggaagtttt cgtggacggt ggtgttcgtc gtggtacaga tgtcttgaaa    1500
gcgttatgtc taggtgctaa aggtgttggt ttgggtagac cattcttgta tcgaactca    1560 tgctatggtc gtaatggtgt tgaaaaagcc attgaaattt taagagatga aattgaaatg    1620
tctatgagac tattaggtgt tactagcatt gcggaattga gcctgatct tttagatcta    1680 tcaacactaa aggcaagaac agttggagta ccaaacgacg tgctgtataa tgaagtttat    1740
gagggaccta cttttaacaga atttgaggat gcatga                             1776
```

<210> SEQ ID NO 41
<211> LENGTH: 348
<212> TYPE: PRT
<213> ORGANISM: Saccharomyces cerevisiae

<400> SEQUENCE: 41

```
Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

<210> SEQ ID NO 42
<211> LENGTH: 1047
<212> TYPE: DNA

<213> ORGANISM: Saccharomyces cerevisiae

<400> SEQUENCE: 42

```
atgtctatcc cagaaactca aaaggtgtt atcttctacg aatcccacgg taagttggaa      60
tacaaagata ttccagttcc aaagccaaag gccaacgaat tgttgatcaa cgttaaatac    120
tctggtgtct gtcacactga cttgcacgct tggcacggtg actggccatt gccagttaag    180
ctaccattag tcggtggtca cgaaggtgcc ggtgtcgttg tcggcatggg tgaaaacgtt    240
aagggctgga agatcggtga ctacgccggt atcaaatggt tgaacggttc ttgtatggcc    300
tgtgaatact gtgaattggg taacgaatcc aactgtcctc acgctgactt gtctggttac    360
acccacgacg gttctttcca acaatacgct accgctgacg ctgttcaagc cgctcacatt    420
cctcaaggta ccgacttggc ccaagtcgcc cccatcttgt gtgctggtat caccgtctac    480
aaggctttga gtctgctaa cttgatggcc ggtcactggg ttgctatctc cggtgctgct    540
ggtggtctag ttctttggc tgttcaatac gccaaggcta tgggttacag agtcttgggt    600
attgacggtg gtgaaggtaa ggaagaatta ttcagatcca tcggtggtga agtcttcatt    660
gacttcacta aggaaaagga cattgtcggt gctgttctaa aggccactga cggtggtgct    720
cacggtgtca tcaacgtttc cgtttccgaa gccgctattg aagcttctac agatacgtt    780
agagctaacg gtaccaccgt tttggtcggt atgccagctg gtgccaagtg ttgttctgat    840
gtcttcaacc aagtcgtcaa gtccatctct attgttggtt cttacgtcgg taacagagct    900
gacaccagag aagctttgga cttcttcgcc agaggtttgg tcaagtctcc aatcaaggtt    960
gtcggcttgt ctaccttgcc agaaatttac gaaaagatgg aaaagggtca atcgttggt   1020
agatacgttg ttgacacttc taaataa                                      1047
```

<210> SEQ ID NO 43
<211> LENGTH: 351
<212> TYPE: PRT
<213> ORGANISM: Saccharomyces cerevisiae

<400> SEQUENCE: 43

```
Met Pro Ser Gln Val Ile Pro Glu Lys Gln Lys Ala Ile Val Phe Tyr
  1               5                  10                  15
Glu Thr Asp Gly Lys Leu Glu Tyr Lys Asp Val Thr Val Pro Glu Pro
                 20                  25                  30
Lys Pro Asn Glu Ile Leu Val His Val Lys Tyr Ser Gly Val Cys His
             35                  40                  45
Ser Asp Leu His Ala Trp His Gly Asp Trp Pro Phe Gln Leu Lys Phe
         50                  55                  60
Pro Leu Ile Gly Gly His Glu Gly Ala Gly Val Val Val Lys Leu Gly
     65                  70                  75                  80
Ser Asn Val Lys Gly Trp Lys Val Gly Asp Phe Ala Gly Ile Lys Trp
                 85                  90                  95
Leu Asn Gly Thr Cys Met Ser Cys Glu Tyr Cys Glu Val Gly Asn Glu
            100                 105                 110
Ser Gln Cys Pro Tyr Leu Asp Gly Thr Gly Phe Thr His Asp Gly Thr
        115                 120                 125
Phe Gln Glu Tyr Ala Thr Ala Asp Ala Val Gln Ala Ala His Ile Pro
    130                 135                 140
Pro Asn Val Asn Leu Ala Glu Val Ala Pro Ile Leu Cys Ala Gly Ile
145                 150                 155                 160
Thr Val Tyr Lys Ala Leu Lys Arg Ala Asn Val Ile Pro Gly Gln Trp
```

```
                165                 170                 175
Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

<210> SEQ ID NO 44
<211> LENGTH: 1056
<212> TYPE: DNA
<213> ORGANISM: Saccharomyces cerevisiae

<400> SEQUENCE: 44
atgccttcgc aagtcattcc tgaaaaacaa aaggctattg tcttttatga gacagatgga      60
aaattggaat ataaagacgt cacagttccg gaacctaagc ctaacgaaat tttagtccac     120
gttaaatatt ctggtgtttg tcatagtgac ttgcacgcgt ggcacggtga ttggccattt     180
caattgaaat ttccattaat cggtggtcac gaaggtgctg tgttgttgt taagtttggga     240 tctaacgtta agggctggaa agtcggtgat tttgcaggta aaaatggtt gaatgggact     300 tgcatgtcct gtgaatattg tgaagtaggt aatgaatctc aatgtcctta tttggatggt     360
actggcttca cacatgatgg tacttttcaa gaatacgcaa ctgccgatgc cgttcaagct     420
gcccatattc caccaaacgt caatcttgct gaagttgccc aatcttgtg tgcaggtatc     480 actgttata aggcgttgaa aagagccaat gtgataccag ccaatgggt cactatatcc     540 ggtgcatgcg gtggcttggg ttctctggca atccaatacg cccttgctat gggttacagg     600
gtcattggta tcgatggtgg taatgccaag cgaaagttat ttgaacaatt aggcggagaa     660
atattcatcg atttcacgga agaaaaagac attgttggtg ctataataaa ggccactaat     720
ggcggttctc atggagttat taatgtgtct gtttctgaag cagctatcga ggcttctacg     780
aggtattgta ggcccaatgg tactgtcgtc ctggttggta tgccagctca tgcttactgc     840
aattccgatg ttttcaatca agttgtaaaa tcaatctcca tcgttggatc ttgtgttgga     900
aatagagctg atacaaggga ggctttagat ttcttcgcca gaggtttgat caaatctccg     960
atccacttag ctggcctatc ggatgttcct gaattttttg caaagatgga aagggtgaa    1020 attgttggta gatatgttgt tgagacttct aaatga                            1056
```

<210> SEQ ID NO 45
<211> LENGTH: 500
<212> TYPE: PRT
<213> ORGANISM: Saccharomyces cerevisiae

<400> SEQUENCE: 45

```
Met Thr Lys Leu His Phe Asp Thr Ala Glu Pro Val Lys Ile Thr Leu
  1               5                  10                  15

Pro Asn Gly Leu Thr Tyr Glu Gln Pro Thr Gly Leu Phe Ile Asn Asn
             20                  25                  30

Lys Phe Met Lys Ala Gln Asp Gly Lys Thr Tyr Pro Val Glu Asp Pro
         35                  40                  45

Ser Thr Glu Asn Thr Val Cys Glu Val Ser Ser Ala Thr Thr Glu Asp
     50                  55                  60

Val Glu Tyr Ala Ile Glu Cys Ala Asp Arg Ala Phe His Asp Thr Glu
 65                  70                  75                  80

Trp Ala Thr Gln Asp Pro Arg Glu Arg Gly Arg Leu Leu Ser Lys Leu
                 85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380
```

```
Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
            405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
            435                 440                 445

Lys Met Leu Lys Ala Gly Thr Val Trp Ile Asn Thr Tyr Asn Asp Phe
450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
            485                 490                 495

Arg Ile Lys Leu
            500

<210> SEQ ID NO 46
<211> LENGTH: 1503
<212> TYPE: DNA
<213> ORGANISM: Saccharomyces cerevisiae

<400> SEQUENCE: 46
atgactaagc tacactttga cactgctgaa ccagtcaaga tcacacttcc aaatggtttg      60
acatacgagc aaccaaccgg tctattcatt aacaacaagt ttatgaaagc tcaagacggt     120
aagacctatc ccgtcgaaga tccttccact gaaaacaccg tttgtgaggt ctcttctgcc     180
accactgaag atgttgaata tgctatcgaa tgtgccgacc gtgctttcca cgacactgaa     240
tgggctaccc aagacccaag agaaagaggc cgtctactaa gtaagttggc tgacgaattg     300
gaaagccaaa ttgacttggt ttcttccatt gaagctttgg acaatggtaa aactttggcc     360
ttagcccgtg gggatgttac cattgcaatc aactgtctaa gagatgctgc tgcctatgcc     420
gacaaagtca acggtagaac aatcaacacc ggtgacggct acatgaactt caccaccta     480 gagccaatcg gtgtctgtgg tcaaattatt ccatggaact tccaataat gatgttggct     540 tggaagatcg ccccagcatt ggccatgggt aacgtctgta tcttgaaacc cgctgctgtc     600
acacctttaa atgccctata ctttgcttct ttatgtaaga aggttggtat tccagctggt     660
gtcgtcaaca tcgttccagg tcctggtaga actgttggtg ctgctttgac caacgaccca     720
agaatcagaa agctggcttt taccggttct acagaagtcg gtaagagtgt tgctgtcgac     780
tcttctgaat ctaacttgaa gaaaatcact ttggaactag gtggtaagtc cgcccatttg     840
gtctttgacg atgctaacat taagaagact ttaccaaatc tagtaaacgg tatttcaag     900 aacgctggtc aaatttgttc ctctggttct agaatttacg ttcaagaagg tatttacgac     960
gaactattgg ctgctttcaa ggcttacttg gaaaccgaaa tcaaagttgg taatccattt    1020
gacaaggcta acttccaagg tgctatcact aaccgtcaac aattcgacac aattatgaac    1080
tacatcgata tcggtaagaa agaaggcgcc aagatcttaa ctggtggcga aaaagttggt    1140
gacaagggtt acttcatcag accaaccgtt ttctacgatg ttaatgaaga catgagaatt    1200
gttaaggaag aaattttggg accagttgtc actgtcgcaa agttcaagac tttagaagaa    1260
ggtgtcgaaa tggctaacag ctctgaattc ggtctaggtt ctggtatcga aacagaatct    1320
ttgagcacag gtttgaaggt ggccaagatg ttgaaggccg gtaccgtctg gatcaacaca    1380
```

```
tacaacgatt ttgactccag agttccattc ggtggtgtta agcaatctgg ttacggtaga    1440
gaaatgggtg aagaagtcta ccatgcatac actgaagtaa aagctgtcag aattaagttg    1500
taa                                                                  1503
```

<210> SEQ ID NO 47
<211> LENGTH: 316
<212> TYPE: PRT
<213> ORGANISM: Escherichia coli

<400> SEQUENCE: 47

```
Met Ser Lys Arg Lys Val Ala Ile Ile Gly Ser Gly Asn Ile Gly Thr
  1               5                  10                  15

Asp Leu Met Ile Lys Ile Leu Arg His Gly Gln His Leu Glu Met Ala
                 20                  25                  30

Val Met Val Gly Ile Asp Pro Gln Ser Asp Gly Leu Ala Arg Ala Arg
             35                  40                  45

Arg Met Gly Val Ala Thr Thr His Glu Gly Val Ile Gly Leu Met Asn
         50                  55                  60

Met Pro Glu Phe Ala Asp Ile Asp Ile Val Phe Asp Ala Thr Ser Ala
 65                  70                  75                  80

Gly Ala His Val Lys Asn Asp Ala Ala Leu Arg Glu Ala Lys Pro Asp
                 85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
    210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala
305                 310                 315
```

<210> SEQ ID NO 48
<211> LENGTH: 951
<212> TYPE: DNA
<213> ORGANISM: Escherichia coli -continued

```
<400> SEQUENCE: 48
atgagtaagc gtaaagtcgc cattatcggt tctggcaaca ttggtaccga tctgatgatt    60
aaaattttgc gtcacggtca gcatctggag atggcggtga tggttggcat tgatcctcag   120
tccgacggtc tggcgcgcgc cagacgtatg ggcgtcgcca ccacccatga agggggtgatc   180
ggactgatga acatgcctga atttgctgat atcgacattg tatttgatgc gaccagcgcc   240
ggtgctcatg tgaaaaacga tgccgcttta cgcgaagcaa accggatat cgcttaatt    300
gacctgacgc ctgctgccat cggcccttac tgcgtgccgg tggttaacct cgaggcgaac   360
gtcgatcaac tgaacgtcaa catggtcacc tgcggcggcc aggccaccat tccaatggtg   420
gcggcagttt cacgcgtggc gcgtgttcat tacgccgaaa ttatcgcttc tatcgccagt   480
aaatctgccg gacctggcac gcgtgccaat atcgatgaat ttacggaaac cacttcccga   540
gccattgaag tggtgggcgg cgcggcaaaa gggaaggcga ttattgtgct taacccagca   600
gagccaccgt tgatgatgcg tgacacggtg tatgtattga cgacgaagc ttcacaagat    660
gatatcgaag cctcaatcaa tgaaatggct gaggcggtgc aggcttacgt accgggttat   720
cgcctgaaac agcgcgtgca gtttgaagtt atcccgcagg ataaaccggt caatttaccg   780
ggcgtggggc aattctccgg actgaaaaca gcggtctggc tggaagtcga aggcgcagcg   840
cattatctgc ctgcctatgc gggcaacctc gacattatga cttccagtgc gctggcgaca   900
gcggaaaaaa tggcccagtc actggcgcgc aaggcaggag aagcggcatg a             951

<210> SEQ ID NO 49
<211> LENGTH: 512
<212> TYPE: PRT
<213> ORGANISM: Saccharomyces cerevisiae

<400> SEQUENCE: 49

Met Ser Val Asn Pro Glu Phe Ile Ala Asp Gly Ile Asp Phe Tyr Pro
1               5                  10                 15

Thr Thr Pro Asp Ala Ala Tyr Phe Asn Ala Ala Asp Gly Lys Asn Lys
            20                  25                  30

Val Asn Arg Ile Asn Gly Asn Ser Glu Asn Leu His His Ser Phe Ala
        35                  40                  45

Ser Gly Cys Arg Arg Ser Ser Leu Ser Val Asp Phe Asn Val Thr Ser
    50                  55                  60

Ser Asp Ser Glu Lys Ser Glu Gln Ser Cys Leu Glu Asn Asn Ser Gln
65                  70                  75                  80

Glu Asp Glu Tyr Phe Cys Asp Ile Phe Ser Thr Glu Leu Lys Leu Asp
                85                  90                  95

Glu Thr Ser Asn Lys Ser Thr Asp Tyr Ser Ser Ser Asn His Gln Tyr
            100                 105                 110

Pro Glu Gln Leu Glu Leu His Asn Tyr Lys Leu Leu Asn Lys Ile Gly
        115                 120                 125

Glu Gly Ala Phe Ser Arg Val Phe Lys Ala Val Gly Ile Asn Thr Asp
    130                 135                 140

Asp Gln Ala Pro Val Ala Ile Lys Ala Ile Lys Lys Gly Ile Ser
145                 150                 155                 160

Ser Asp Ala Ile Leu Lys Gly Asn Asp Arg Ile Gln Gly Ser Ser Arg
                165                 170                 175

Lys Lys Val Leu Asn Glu Val Ala Ile His Lys Leu Val Ser Lys Asn
            180                 185                 190
```

Asn Pro His Cys Thr Lys Phe Ile Ala Phe Gln Glu Ser Ala Asn Tyr
        195                 200                 205

Tyr Tyr Leu Val Thr Glu Leu Val Thr Gly Gly Glu Ile Phe Asp Arg
        210                 215                 220

Ile Val Gln Leu Thr Cys Phe Ser Glu Asp Leu Ala Arg His Val Ile
225                 230                 235                 240

Thr Gln Val Ala Ile Ala Ile Lys His Met His Tyr Met Gly Ile Val
                245                 250                 255

His Arg Asp Val Lys Pro Glu Asn Leu Leu Phe Glu Pro Ile Pro Phe
                260                 265                 270

Tyr Gly Leu Asp Gly Asp Met Gln Lys Glu Asp Glu Phe Thr Leu Gly
        275                 280                 285

Val Gly Gly Gly Ile Gly Leu Val Lys Leu Met Asp Phe Gly Leu
        290                 295                 300

Ala Lys Lys Leu Arg Asn Asn Thr Ala Lys Thr Pro Cys Gly Thr Ile
305                 310                 315                 320

Glu Tyr Val Ala Ser Glu Val Phe Thr Ser Lys Arg Tyr Ser Met Lys
                325                 330                 335

Val Asp Met Trp Ser Ile Gly Cys Val Leu Phe Thr Leu Leu Cys Gly
                340                 345                 350

Tyr Pro Pro Phe Tyr Glu Lys Asn Glu Lys Thr Leu Leu Lys Lys Ile
        355                 360                 365

Ser Arg Gly Asp Tyr Glu Phe Leu Ala Pro Trp Trp Asp Asn Ile Ser
        370                 375                 380

Ser Gly Ala Lys Asn Ala Val Thr His Leu Leu Glu Val Asp Pro Asn
385                 390                 395                 400

Lys Arg Tyr Asp Ile Asp Asp Phe Leu Asn Asp Pro Trp Leu Asn Ser
                405                 410                 415

Tyr Asp Cys Leu Lys Asp Ser Asn Ser Asn Ser Tyr Ala Ser Val Gln
                420                 425                 430

Ser Ile Leu Asn Asp Ser Phe Asp Glu Arg Ala Glu Thr Leu His Cys
        435                 440                 445

Ala Leu Ser Cys Gln Ser Glu Lys Gln Asp Asp Thr Glu Phe Ser Arg
450                 455                 460

Ser Glu Ser Ser Glu Tyr Ile Phe Met Thr Glu Glu Asp Arg Asn Leu
465                 470                 475                 480

Arg Gly Ser Trp Ile Gly Pro Lys Glu Cys Phe Thr Leu Asp Leu
                485                 490                 495

Ala Thr Ser Ser Ile Tyr Arg Arg Lys Asn Lys Ile Phe Phe Trp
                500                 505                 510

<210> SEQ ID NO 50
<211> LENGTH: 1539
<212> TYPE: DNA
<213> ORGANISM: Saccharomyces cerevisiae

<400> SEQUENCE: 50
atgtcagtaa acccagaatt tatagccgat ggcatcgatt tttatccaac aacgcccgat      60
gccgcgtatt tcaatgccgc tgatggtaaa aataaagtta acaggataaa tggtaactca     120
gaaaatttac accactcctt tgcatcgggt tgccgtagat catctctttc agtcgacttt     180
aatgttacct cgtccgattc agaaaaaagt gaacagagct gcttggaaaa caactctcaa     240
gaagacgaat atttttgtga cattttttcc actgaattaa aattagatga aacttctaac     300
aagtcaaccg attattccag ttcaaatcac cagtatcctg aacaactgga gttgcacaat     360

```
tataaactgc tcaataaaat tggtgaaggg gcattttcca gagtatttaa agcagtaggc   420
atcaacacgg atgaccaagc tcctgttgcc atcaaagcaa tcataaagaa aggcatttcg   480
agcgatgcca tcttaaaagg gaatgataga atccaaggtt ccagcagaaa gaaagtctta   540
aacgaagttg ccatccacaa actggtttcg aaaataatc cgcattgtac aaaatttatc    600
gcattccagg aatcggcgaa ctactattac ttagtgacgg agttagtcac aggtggggaa   660
atatttgata ggatcgtcca actaacatgc tttagtgaag acttagctcg tcatgtcatt   720
actcaggtag caattgcaat taaacatatg cactacatgg gtattgtgca tcgtgatgtc   780
aaaccagaaa acctactatt tgaacctatc ccatttatg gccttgatgg ggacatgcaa    840
aaagaagacg agtttacatt aggtgtcggc ggaggcggta ttggtttagt gaagctaatg   900
gacttcggac tagccaagaa acttcggaac aataccgcaa aaactccctg cggaacgata   960
gaatacgtcg catcagaagt attcacctcc aaacgatatt ccatgaaagt tgatatgtgg  1020
agtattggct gcgtactatt cacgttattg tgtggatatc ctccgtttta cgaaaagaac  1080
gaaaaaacat tattgaagaa aatatcgaga ggagattacg aattcttggc gccatggtgg  1140
gacaacataa gttctggcgc taagaacgca gttacccatc ttttggaggt tgacccaaac  1200
aagagatacg atatcgatga cttcctaaat gatccttggt taaattcgta cgattgtttg  1260
aaggattcaa actcaaattc ttatgccagc gtgcaaagca tactaaatga ttcattcgat  1320
gagagagcag agaccctaca ttgtgcatta agctgccaat ctgaaaaaca agatgacacc  1380
gagttttcca gaagtgaaag ctcggaatac atatttatga cggaagaaga cagaaaccta  1440
cggggcagtt ggatcggtga gccaaaagag tgttttacct tagaccttgc aacatcttct  1500
atataccgaa gaaggaagaa caagatattc ttctggtaa                         1539
```

<210> SEQ ID NO 51
<211> LENGTH: 610
<212> TYPE: PRT
<213> ORGANISM: Saccharomyces cerevisiae

<400> SEQUENCE: 51

```
Met Leu Lys Ile Lys Ala Leu Phe Ser Lys Lys Pro Asp Gln Ala
1               5                   10                  15

Asp Leu Ser Gln Glu Ser Lys Lys Pro Phe Lys Gly Lys Thr Arg Ser
            20                  25                  30

Ser Gly Thr Asn Asn Lys Asp Val Ser Gln Ile Thr Ser Ser Pro Lys
        35                  40                  45

Lys Ser Phe Gln Asp Lys Asn Ile Val Gln Tyr Pro Ser Val Val Ala
    50                  55                  60

Asp Asp His His Met Lys Ser Leu Thr Asp Glu Leu Val Thr Thr Ile
65                  70                  75                  80

Asp Ser Asp Ser Ser Pro Ser Asp Asn Ile Thr Thr Glu Asn Val Glu
                85                  90                  95

Thr Val Thr Ser Val Pro Ala Ile Asp Val His Glu Ser Ser Glu Gly
            100                 105                 110

Gln Leu Ser Ser Asp Pro Leu Ile Ser Asp Glu Ser Leu Ser Glu Gln
        115                 120                 125

Ser Glu Ile Ile Ser Asp Ile Gln Asp Asp Ser Thr Asp Asp Asn
    130                 135                 140

Met Glu Asp Glu Ile Pro Glu Lys Ser Phe Leu Glu Gln Lys Glu Leu
145                 150                 155                 160
```

Ile Gly Tyr Lys Leu Ile Asn Lys Ile Gly Glu Gly Ala Phe Ser Lys
            165                 170                 175

Val Phe Arg Ala Ile Pro Ala Lys Asn Ser Asn Glu Phe Leu Thr
        180                 185                 190

Lys Asn Tyr Lys Ala Val Ala Ile Lys Val Ile Lys Lys Ala Asp Leu
        195                 200                 205

Ser Ser Ile Asn Gly Asp His Arg Lys Lys Asp Lys Gly Lys Asp Ser
    210                 215                 220

Thr Lys Thr Ser Ser Arg Asp Gln Val Leu Lys Glu Val Ala Leu His
225                 230                 235                 240

Lys Thr Val Ser Ala Gly Cys Ser Gln Ile Val Ala Phe Ile Asp Phe
                245                 250                 255

Gln Glu Thr Asp Ser Tyr Tyr Ile Ile Gln Glu Leu Leu Thr Gly
            260                 265                 270

Gly Glu Ile Phe Gly Glu Ile Val Arg Leu Thr Tyr Phe Ser Glu Asp
        275                 280                 285

Leu Ser Arg His Val Ile Lys Gln Leu Ala Leu Ala Val Lys His Met
    290                 295                 300

His Ser Leu Gly Val Val His Arg Asp Ile Lys Pro Glu Asn Leu Leu
305                 310                 315                 320

Phe Glu Pro Ile Glu Phe Thr Arg Ser Ile Lys Pro Lys Leu Arg Lys
                325                 330                 335

Ser Asp Asp Pro Gln Thr Lys Ala Asp Glu Gly Ile Phe Thr Pro Gly
            340                 345                 350

Val Gly Gly Gly Ile Gly Ile Val Lys Leu Ala Asp Phe Gly Leu
        355                 360                 365

Ser Lys Gln Ile Phe Ser Lys Asn Thr Lys Thr Pro Cys Gly Thr Val
    370                 375                 380

Gly Tyr Thr Ala Pro Glu Val Val Lys Asp Glu His Tyr Ser Met Lys
385                 390                 395                 400

Val Asp Met Trp Gly Ile Gly Cys Val Leu Tyr Thr Met Leu Cys Gly
                405                 410                 415

Phe Pro Pro Phe Tyr Asp Glu Lys Ile Asp Thr Leu Thr Glu Lys Ile
            420                 425                 430

Ser Arg Gly Glu Tyr Thr Phe Leu Lys Pro Trp Trp Asp Glu Ile Ser
    435                 440                 445

Ala Gly Ala Lys Asn Ala Val Ala Lys Leu Leu Glu Leu Glu Pro Ser
    450                 455                 460

Lys Arg Tyr Asp Ile Asp Gln Phe Leu Asp Asp Pro Trp Leu Asn Thr
465                 470                 475                 480

Phe Asp Cys Leu Pro Lys Glu Gly Glu Ser Ser Gln Lys Lys Ala Gly
                485                 490                 495

Thr Ser Glu Arg Arg His Pro His Lys Lys Gln Phe Gln Leu Phe Gln
            500                 505                 510

Arg Asp Ser Ser Leu Leu Phe Ser Pro Ala Ala Val Ala Met Arg Asp
    515                 520                 525

Ala Phe Asp Ile Gly Asn Ala Val Lys Arg Thr Glu Glu Asp Arg Met
        530                 535                 540

Gly Thr Arg Gly Gly Leu Gly Ser Leu Ala Glu Asp Glu Leu Glu
545                 550                 555                 560

Asp Ser Tyr Ser Gly Ala Gln Gly Asp Glu Gln Leu Glu Gln Asn Met
                565                 570                 575

Phe Gln Leu Thr Leu Asp Thr Ser Thr Ile Leu Gln Arg Arg Lys Lys 580                 585                 590
Val Gln Glu Asn Asp Val Gly Pro Thr Ile Pro Ile Ser Ala Thr Ile
            595                 600                 605

Arg Glu
    610

<210> SEQ ID NO 52
<211> LENGTH: 1833
<212> TYPE: DNA
<213> ORGANISM: Saccharomyces cerevisiae

<400> SEQUENCE: 52

| | | | | | |
|---|---|---|---|---|---|
| atgcttaaaa | taaaggccct | tttctcgaaa | agaaaccgg | atcaggcaga | tttgtctcag | 60 |
| gaatctaaaa | aaccattcaa | gggtaagacc | aggtcaagcg | gtacaaataa | caaagatgtt | 120 |
| tcccagatta | cttcttcccc | taagaaaagc | tttcaggaca | aaaatatagt | tcagtacccg | 180 |
| agtgttgtcg | cagatgacca | tcatatgaag | tctttaaccg | atgaattagt | aaccacgata | 240 |
| gactcggact | cttcaccgag | tgataatatt | accacgaaa | atgtggaaac | agttacttcc | 300 |
| gtgccagcta | tcgatgtcca | tgaaagtagt | gaaggtcaat | taagttccga | ccccttaata | 360 |
| tctgacgaat | ctctttcgga | acaaagcgag | attatcagtg | atatccagga | tgacagtact | 420 |
| gatgatgaca | atatggaaga | tgaaattccg | gaaaaatcct | tcctcgaaca | aaaggaattg | 480 |
| ataggttaca | agctgatcaa | taaatcggt | gaaggtgctt | tttcaaaagt | ctttagagcc | 540 |
| atacctgcta | aaaatagttc | taatgaattt | ttaactaaaa | actataaagc | tgttgccatt | 600 |
| aaagttatca | aaaaggcaga | tttatcctcg | attaatggtg | atcatcgtaa | gaaggacaaa | 660 |
| gggaaggaca | gcactaaaac | ttcttccaga | gatcaagtct | tgaaggaagt | tgcactacat | 720 |
| aagacggttt | ccgctggttg | ttcacaaatt | gtcgcgttca | tagacttcca | agaaacagat | 780 |
| agctattatt | atattattca | agagttacta | accggtgggg | aaatcttcgg | cgaaattgtt | 840 |
| aggttgaccct | atttcagtga | agatttatca | aggcatgtaa | tcaaacaatt | agcactggct | 900 |
| gttaaacata | tgcattcact | aggtgtagtg | catcgtgata | aaaacctga | gaatcttctt | 960 |
| tttgaaccga | ttgaattcac | acgctctata | aaaccaaaat | tgaggaaatc | ggatgatccg | 1020 |
| caaacaaagg | cagacgaggg | aattttcaca | ccaggagttg | gtggtggtgg | aattggtata | 1080 |
| gtaaaactag | ctgattttgg | tttgtctaaa | caaatatttt | ccaagaacac | caagactcct | 1140 |
| tgtggtacag | tcggttacac | tgcccctgaa | gttgtcaaag | atgagcatta | ttctatgaaa | 1200 |
| gtggatatgt | gggggattgg | ttgcgttttg | tacacaatgt | tatgtgggtt | cccgccattc | 1260 |
| tatgatgaga | aaattgacac | tttaactgaa | aaaatatcaa | ggggtgagta | taccttctg | 1320 |
| aaaccttggt | gggatgaaat | cagcgccggt | gccaagaatg | ccgtggctaa | gctattagaa | 1380 |
| ctagagccgt | ctaaaagata | cgacattgac | cagttttgg | acgacccatg | gttaaataca | 1440 |
| ttcgattgtt | taccaaagga | gggcgaatct | tcacaaaaga | aagcaggtac | ttccgaaaga | 1500 |
| cgccatccgc | ataagaaaca | attccaacta | tttcaaagag | actcctcgct | actgttttca | 1560 |
| ccagctgctg | ttgctatgcg | tgacgccttt | gatattggta | atgctgtgaa | acgtaccgaa | 1620 |
| gaagaccgta | tgggaacacg | tggaggatta | ggctcgcttg | ctgaggacga | agaattggaa | 1680 |
| gatagttaca | gtggcgccca | aggcgatgaa | cagctggaac | aaaatatgtt | ccaattaacg | 1740 |
| ctggatacgt | ccacgattct | gcaaagaaga | aaaaagttc | aagaaaatga | cgtagggcct | 1800 |
| acaattccaa | taagcgccac | tatcagggaa | tag | | | 1833 |

<210> SEQ ID NO 53
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 53

```
atttggcgag cgttggttgg tggatcaagc ccacgcgtag gcaatcctcg agcagatccg      60
ccaggcgtgt atatatagcg tggatggcca ggcaacttta gtgctgacac atacaggcat     120
atatatatgt gtgcgacgac acatgatcat atggcatgca tgtgctctgt atgtatataa     180
aactcttgtt ttcttctttt ctctaaatat tctttcctta tacattagga cctttgcagc     240
ataaattact atacttctat agacacgcaa acacaaatac acacactaa                 289
```

<210> SEQ ID NO 54
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 54

```
atagcttcaa aatgtttcta ctccttttt actcttccag attttctcgg actccgcgca       60
tcgccgtacc acttcaaaac acccaagcac agcatactaa atttcccctc tttcttcctc     120
tagggtgtcg ttaattaccc gtactaaagg tttggaaaag aaaaaagaga ccgcctcgtt     180
tctttttctt cgtcgaaaaa ggcaataaaa atttttatca cgtttctttt tcttgaaaat     240
ttttttttg attttttttct ctttcgatga cctcccattg atatttaagt taataaacgg     300
tcttcaattt ctcaagtttc agtttcattt tcttgttct attacaactt ttttacttc      360
ttgctcatta gaaagaaagc atagcaatct aatctaagtt t                         401
```

<210> SEQ ID NO 55
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 55

```
agtttatcat tatcaatact cgccatttca aagaatacgt aaataattaa tagtagtgat      60
tttcctaact ttatttagtc aaaaaattag ccttttaatt ctgctgtaac ccgtacatgc     120
ccaaaatagg gggcgggtta cacagaatat ataacatcgt aggtgtctgg gtgaacagtt     180
tattcctggc atccactaaa tataatggag cccgcttttt aagctggcat ccagaaaaaa     240
aaagaatccc agcaccaaaa tattgttttc ttcaccaacc atcagttcat aggtccattc     300
tcttagcgca actacagaga acaggggcac aaacaggcaa aaacgggca caacctcaat     360
ggagtgatgc aacctgcctg gagtaaatga tgacacaagg caattgaccc acgcatgtat     420
ctatctcatt ttcttacacc ttctattacc ttctgctctc tctgatttgg aaaaagctga     480
aaaaaaaggt tgaaaccagt tccctgaaat tattccccta cttgactaat aagtatataa     540
agacggtagg tattgattgt aattctgtaa atctatttct taaacttctt aaattctact     600
tttatagtta gtcttttttt tagttttaaa acaccagaac ttagtttcga cggat         655
```

<210> SEQ ID NO 56
<211> LENGTH: 1468
<212> TYPE: DNA

<213> ORGANISM: Artificial Sequence
<220> FEATURE:
<221> NAME/KEY: MISC_FEATURE
<222> LOCATION: (1)..(1468)
<223> OTHER INFORMATION: ADH promoter

<400> SEQUENCE: 56

```
gccgggatcg aagaaatgat ggtaaatgaa ataggaaatc aaggagcatg aaggcaaaag      60
acaaatataa gggtcgaacg aaaaataaag tgaaaagtgt tgatatgatg tatttggctt     120
tgcggcgccg aaaaaacgag tttacgcaat tgcacaatca tgctgactct gtggcggacc     180
cgcgctcttg ccggcccggc gataacgctg ggcgtgaggc tgtgcccggc ggagttttttt   240
gcgcctgcat tttccaaggt ttaccctgcg ctaaggggcg agattggaga agcaataaga     300
atgccggttg gggttgcgat gatgacgacc acgacaactg tgtcattat ttaagttgcc      360
gaaagaacct gagtgcattt gcaacatgag tatactagaa gaatgagcca agacttgcga     420
gacgcgagtt tgccggtggt gcgaacaata gagcgaccat gaccttgaag gtgagacgcg     480
cataaccgct agagtacttt gaagaggaaa cagcaatagg gttgctacca gtataaatag     540
acaggtacat acaacactgg aaatggttgt ctgtttgagt acgctttcaa ttcatttggg     600
tgtgcacttt attatgttac aatatggaag gaactttac acttctccta tgcacatata     660
ttaattaaag tccaatgcta gtagagaagg ggggtaacac ccctccgcgc tcttttccga    720
ttttttttcta aaccgtggaa tatttcggat atcctttttgt tgtttccggg tgtacaatat    780
ggacttcctc ttttctggca accaaaccca tacatcggga ttcctataat accttcgttg      840
gtctccctaa catgtaggtg gcggagggga gatatacaat agaacagata ccagacaaga    900
cataatgggc taaacaagac tacaccaatt acactgcctc attgatggtg gtacataacg     960
aactaatact gtagccctag acttgatagc catcatcata tcgaagtttc actacccttt    1020
ttccatttgc catctattga agtaataata ggcgcatgca acttcttttc tttttttttc    1080
ttttctctct ccccgttgt tgtctcacca tatccgcaat gacaaaaaaa tgatggaaga    1140
cactaaagga aaaattaac gacaaagaca gcaccaacag atgtcgttgt tccagagctg    1200
atgaggggta tctcgaagca cacgaaactt tttccttcct tcattcacgc acactactct    1260
ctaatgagca acggtatacg gccttccttc cagttacttg aatttgaaat aaaaaaagt     1320
ttgctgtctt gctatcaagt ataaatagac ctgcaattat taatcttttg ttttcctcgtc    1380
attgttctcg ttccctttct tccttgtttc tttttctgca caatatttca agctatacca    1440
agcatacaat caactccaag ctggccgc                                       1468
```

<210> SEQ ID NO 57
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 57

```
ttcgcggcca cctacgccgc tatctttgca acaactatct gcgataactc agcaaatttt      60
gcatattcgt gttgcagtat tgcgataatg ggagtcttac ttccaacata acggcagaaa     120
gaaatgtgag aaaattttgc atcctttgcc tccgttcaag tatataaagt cggcatgctt     180
gataatcttt ctttccatcc tacattgttc taattattct tattctcctt tattctttcc    240
taacatacca agaaattaat cttctgtcat tcgcttaaac actatatcaa ta             292
```

<210> SEQ ID NO 58
<211> LENGTH: 676
<212> TYPE: DNA
<213> ORGANISM: Artificial Sequence
<220> FEATURE:
<223> OTHER INFORMATION: Synthetic HHT2 promoter

<400> SEQUENCE: 58

```
attttattgt attgattgtt gttttgcta ctctttgaa caagatgtag gaaaaaagat    60
agagaaaaga ataaattaag cgaaaaaaaa aaatctctt tcaccgcctc atcctaatat   120
acttatatat gatataacta catacgcaca aacacgtatg tatctagccg aataacaaca   180
gcccaggcgc gagtgaacaa catattaaat taaacgcctt cttgtcagtt gttttgttct   240
ggtctggtct gcatttcgcg cccgaaaaag cttgagacgc gaagctccca gaacgtcctg   300
ccatacaaat gcgaaactct cggtctagta ccactttccc ggtgccaaac gaccacagtt   360
gtccgttccg agcacttcgc attaagcgcg tgaaactatt ggcacgccct aaggggctcc   420
tacggatggg agttggtcat ttagcgttca ttatcgccca atgtgacgca caatcacggc   480
tatggctcgg tgtcaaaaca tagtttgcgt gataacagcg tgttgtgctc tctcgcgttg   540
cttcttgtga ccgcagttgt atataaataa tcttttttctt gttctttttat ataggaccac   600
tgttttgtga cttccacttt ggcccttcca actgttcttc ccctttact aaaggatcca   660
agcaaacact ccacaa                                                   676
```

<210> SEQ ID NO 59
<211> LENGTH: 500
<212> TYPE: DNA
<213> ORGANISM: Artificial Sequence
<220> FEATURE:
<223> OTHER INFORMATION: Synthetic TPI promoter

<400> SEQUENCE: 59

```
atttaaactg tgaggacctt aatacattca gacacttctg cggtatcacc ctacttattc    60
ccttcgagat tatatctagg aacccatcag gttggtggaa gattacccgt tctaagactt   120
ttcagcttcc tctattgatg ttacacctgg acaccccttt tctggcatcc agttttttaat   180
cttcagtggc atgtgagatt ctccgaaatt aattaaagca atcacacaat tctctcggat   240
accacctcgg ttgaaactga caggtggttt gttacgcatg ctaatgcaaa ggagcctata   300
tacctttggc tcggctgctg taacagggaa tataaagggc agcataattt aggagtttag   360
tgaacttgca acatttacta ttttcccttc ttacgtaaat attttctttt ttaattctaa   420
atcaatcttt ttcaattttt tgtttgtatt cttttcttgc ttaaatctat aactacaaaa   480
aacacataca taaactaaaa                                                500
```

<210> SEQ ID NO 60
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 60

```
tcatgtaatt agttatgtca cgcttacatt cacgccctcc ccccacatcc gctctaaccg    60
aaaaggaagg agttagacaa cctgaagtct aggtccctat ttatttttt atagttatgt   120
tagtattaag aacgttattt atatttcaaa tttttctttt ttttctgtac agacgcgtgt   180
acgcatgtaa cattatactg aaaaccttgc ttgagaaggt tttgggacgc tcgaaggctt   240
```
taatttgcgg cc                                                                              252

<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61
cgagctcttc gcggccacct acgccgctat c                                                          31

<210> SEQ ID NO 62
<211> LENGTH: 32
<212> TYPE: DNA
<213> ORGANISM: Artificial Sequence
<220> FEATURE:
<223> OTHER INFORMATION: primer

<400> SEQUENCE: 62
gctctagata ttgatatagt gtttaagcga at                                                         32

<210> SEQ ID NO 63
<211> LENGTH: 27
<212> TYPE: DNA
<213> ORGANISM: Artificial Sequence
<220> FEATURE:
<223> OTHER INFORMATION: primer

<400> SEQUENCE: 63
cggccatggc gggagctcgc atgcaag                                                               27

<210> SEQ ID NO 64
<211> LENGTH: 28
<212> TYPE: DNA
<213> ORGANISM: Artificial Sequence
<220> FEATURE:
<223> OTHER INFORMATION: primer

<400> SEQUENCE: 64
cgggatatca ctagtgagct cgctccgc                                                              28

<210> SEQ ID NO 65
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 65
gccgggagag ctcgcatgca agtaacctat tcaaagtaat atctcataca tgtttcatga     60
gggtaacaac atgcgactgg gtgagcatat gttccgctga tgtgatgtgc aagataaaca    120
agcaaggcag aaactaactt cttcttcatg taataaacac accccgcgtt tatttaccta    180
tctctaaact tcaacacctt atatcataac taatatttct tgagataagc acactgcacc    240
cataccttcc ttaaaaacgt agcttccagt ttttggtggt tccggcttcc ttcccgattc    300
cgcccgctaa acgcatattt ttgttgcctg gtggcatttg caaaatgcat aacctatgca    360
tttaaaagat tatgtatgct cttctgactt tcgtgtgat gaggctcgtg gaaaaaatga    420
ataatttatg aatttgagaa caattttgtg ttgttacggt attttactat ggaataatca    480
atcaattgag gattttatgc aaatatcgtt tgaatatttt ccgacccctt gagtactttt    540
tcttcataat tgcataatat tgtccgctgc ccctttttct gttagacggt gtcttgatct    600

```
acttgctatc gttcaacacc accttatttt ctaactatttt tttttttagc tcatttgaat    660
cagcttatgg tgatggcaca ttttttgcata aacctagctg tcctcgttga acataggaaa    720
aaaaaatata taaacaaggc tctttcactc tccttgcaat cagatttggg tttgttccct    780
ttattttcat atttcttgtc atattccttt ctcaattatt attttctact cataacctca    840
cgcaaaataa cacagtcaaa tcctcgagat gaaaaagcct gaactcaccg cgacgtctgt    900
cgagaagttt ctgatcgaaa agttcgacag cgtctccgac ctgatgcagc tctcggaggg    960
cgaagaatct cgtgctttca gcttcgatgt aggagggcgt ggatatgtcc tgcgggtaaa   1020
tagctgcgcc gatggtttct acaaagatcg ttatgtttat cggcactttg catcggccgc   1080
gctcccgatt ccggaagtgc ttgacattgg ggaattcagc gagagcctga cctattgcat   1140
ctcccgccgt gcacagggtg tcacgttgca agacctgcct gaaaccgaac tgcccgctgt   1200
tctgcagccg gtcgcggagg ccatggatgc gatcgctgcg gccgatctta gccagacgag   1260
cgggttcggc ccattcggac cgcaaggaat cggtcaatac actacatggc gtgatttcat   1320
atgcgcgatt gctgatcccc atgtgtatca ctggcaaact gtgatggacg acaccgtcag   1380
tgcgtccgtc gcgcaggctc tcgatgagct gatgctttgg gccgaggact gccccgaagt   1440
ccggcacctc gtgcacgcgg atttcggctc caacaatgtc ctgacggaca atggccgcat   1500
aacagcggtc attgactgga gcgaggcgat gttcggggat tcccaatacg aggtcgccaa   1560
catcttcttc tggaggccgt ggttggcttg tatggagcag cagacgcgct acttcgagcg   1620
gaggcatccg gagcttgcag gatcgccgcg gctccgggcg tatatgctcc gcattggtct   1680
tgaccaactc tatcagagct tggttgacgg caatttcgat gatgcagctt gggcgcaggg   1740
tcgatgcgac gcaatcgtcc gatccggagc cgggactgtc gggcgtacac aaatcgcccg   1800
cagaagcgcg gccgtctgga ccgatggctg tgtagaagta ctcgccgata gtggaaaccg   1860
acgccccagc actcgtccgg atcgggagat ggggagggct aactgaggat ccgtagatac   1920
attgatgcta tcaatcaaga gaactggaaa gattgtgtaa ccttgaaaaa cggtgaaact   1980
tacgggtcca agattgtcta cagattttcc tgatttgcca gcttactatc cttcttgaaa   2040
atatgcactc tatatctttt agttcttaat tgcaacacat agatttgctg tataacgaat   2100
tttatgctat tttttaaatt tggagttcag tgataaaagt gtcacagcga atttcctcac   2160
atgtagggac cgaattgttt acaagttctc tgtaccacca tggagacatc aaaaattgaa   2220
aatctatgga aagatatgga cggtagcaac aagaatatag cacgagccgc ggagcgagct   2280
cggccgcact agtgatatcc cgcggccatg gcggccggga g                        2321
```

<210> SEQ ID NO 66
<211> LENGTH: 18
<212> TYPE: DNA
<213> ORGANISM: Artificial Sequence
<220> FEATURE:
<223> OTHER INFORMATION: primer

<400> SEQUENCE: 66

```
gaaacagcta tgaccatg                                                    18
```

<210> SEQ ID NO 67
<211> LENGTH: 32
<212> TYPE: DNA
<213> ORGANISM: Artificial Sequence
<220> FEATURE:
<223> OTHER INFORMATION: primer

<400> SEQUENCE: 67
gacatgacga gctcgaattg ggtaccggcc gc							32

<210> SEQ ID NO 68
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 68

| | |
|---|---|
| gatgacggtg aaaacctctg acacatgcag ctcccggaga cggtcacagc ttgtctgtaa | 60 |
| gcggatgccg ggagcagaca agcccgtcag ggcgcgtcag cgggtgttgg cgggtgtcgg | 120 |
| ggctggctta actatgcggc atcagagcag attgtactga gagtgcacca tatgcggtgt | 180 |
| gaaataccgc acagatgcgt aaggagaaaa taccgcatca ggcgccattc gccattcagg | 240 |
| ctgcgcaact gttgggaagg gcgatcggtg cgggcctctt cgctattacg ccagctggcg | 300 |
| aaagggggat gtgctgcaag gcgattaagt tgggtaacgc cagggttttc ccagtcacga | 360 |
| cgttgtaaaa cgacggccag tgaattcgag ctcggtacct cgcgaatgca tctagatatc | 420 |
| ggatcccgac gagctgcacc gcggtggcgg ccgtatcttt acccatacg atgttcctga | 480 |
| ctatgcgggc tatccctatg acgtcccgga ctatgcagga tcctatccat atgacgttcc | 540 |
| agattacgct gctcagtgcg gccgcctgag agtgcaccat accacagctt ttcaattcaa | 600 |
| ttcatcattt ttttttattt ctttttttg atttcggttt ctttgaaatt ttttttgattc | 660 |
| ggtaatctcc gaacagaagg aagaacgaag gaaggagcac agacttagat tggtatatat | 720 |
| acgcatatgt agtgttgaag aaacatgaaa ttgcccagta ttcttaaccc aactgcacag | 780 |
| aacaaaaacc tgcaggaaac gaagataaat catgtcgaaa gctacatata aggaacgtgc | 840 |
| tgctactcat cctagtcctg ttgctgccaa gctatttaat atcatgcacg aaaagcaaac | 900 |
| aaacttgtgt gcttcattgg atgttcgtac caccaaggaa ttactggagt tagttgaagc | 960 |
| attaggtccc aaaatttgtt tactaaaaac acatgtggat atcttgactg attttttccat | 1020 |
| ggagggcaca gttaagccgc taaaggcatt atccgccaag tacaattttt tactcttcga | 1080 |
| agacagaaaa tttgctgaca ttggtaatac agtcaaattg cagtactctg cgggtgtata | 1140 |
| cagaatagca gaatgggcag acattacgaa tgcacgggt gtggtgggcc caggtattgt | 1200 |
| tagcggtttg aagcaggcgg cagaagaagt aacaaaggaa cctagaggcc ttttgatgtt | 1260 |
| agcagaattg tcatgcaagg gctccctatc tactggagaa tatactaagg gtactgttga | 1320 |
| cattgcgaag agcgacaaag attttgttat cggctttatt gctcaaagag acatgggtgg | 1380 |
| aagagatgaa ggttacgatt ggttgattat gacaccggt gtgggtttag atgcaaggg | 1440 |
| agacgcattg ggtcaacagt atagaaccgt ggatgatgtg gtctctacag gatctgacat | 1500 |
| tattattgtt ggaagaggac tatttgcaaa gggaagggat gctaaggtag agggtgaacg | 1560 |
| ttacagaaaa gcaggctggg aagcatattt gagaagatgc ggccagcaaa actaaaaaac | 1620 |
| tgtattataa gtaaatgcat gtatactaaa ctcacaaatt agagcttcaa tttaattata | 1680 |
| tcagttatta ccctatgcgg tgtgaaatac cgcacagatg cgtaaggaga aataccgca | 1740 |
| tcaggaaatt gtagcggccg cgaatttgag cttatctttt acccatacga tgttcctgac | 1800 |
| tatgcgggct atccctatga cgtcccggac tatgcaggat cctatccata tgacgttcca | 1860 |
| gattacgcta ctagcggggg gcccggtgac gggcccgtcg actgcagagg cctgcatgca | 1920 |
| agcttggcgt aatcatggtc atagctgttt cctgtgtgaa attgttatcc gctcacaatt | 1980 |

```
ccacacaaca tacgagccgg aagcataaag tgtaaagcct ggggtgccta atgagtgagc    2040
taactcacat taattgcgtt gcgctcactg cccgctttcc agtcgggaaa cctgtcgtgc    2100
cagctgcatt aatgaatcgg ccaacgcgcg gggagaggcg gtttgcgtat tgggcgctct    2160
tccgcttcct cgctcactga ctcgctgcgc tcggtcgttc ggctgcggcg agcggtatca    2220
gctcactcaa aggcggtaat acggttatcc acagaatcag gggataacgc aggaaagaac    2280
atgtgagcaa aaggccagca aaaggccagg aaccgtaaaa aggccgcgtt gctggcgttt    2340
ttccataggc tccgcccccc tgacgagcat cacaaaaatc gacgctcaag tcagaggtgg    2400
cgaaacccga caggactata agataccagg cgtttccccc tggaagctc cctcgtgcgc    2460 tctcctgttc cgaccctgcc gcttaccgga tacctgtccg cctttctccc ttcgggaagc    2520
gtggcgcttt ctcatagctc acgctgtagg tatctcagtt cggtgtaggt cgttcgctcc    2580
aagctgggct gtgtgcacga accccccgtt cagcccgacc gctgcgcctt atccggtaac    2640
tatcgtcttg agtccaaccc ggtaagacac gacttatcgc cactggcagc agccactggt    2700
aacaggatta gcagagcgag gtatgtaggc ggtgctacag agttcttgaa gtggtggcct    2760
aactacggct acactagaag aacagtattt ggtatctgcg ctctgctgaa gccagttacc    2820
ttcggaaaaa gagttggtag ctcttgatcc ggcaaacaaa ccaccgctgg tagcggtggt    2880
ttttttgttt gcaagcagca gattacgcgc agaaaaaaag gatctcaaga agatcctttg    2940
atcttttcta cggggtctga cgctcagtgg aacgaaaact cacgttaagg gattttggtc    3000
atgagattat caaaaaggat cttcacctag atccttttaa attaaaaatg aagttttaaa    3060
tcaatctaaa gtatatatga gtaaacttgg tctgacagtt accaatgctt aatcagtgag    3120
gcacctatct cagcgatctg tctatttcgt tcatccatag ttgcctgact ccccgtcgtg    3180
tagataacta cgatacggga gggcttacca tctggcccca gtgctgcaat gataccgcga    3240
gacccacgct caccggctcc agatttatca gcaataaacc agccagccgg aagggccgag    3300
cgcagaagtg gtcctgcaac tttatccgcc tccatccagt ctattaattg ttgccgggaa    3360
gctagagtaa gtagttcgcc agttaatagt ttgcgcaacg ttgttgccat tgctacaggc    3420
atcgtggtgt cacgctcgtc gtttggtatg gcttcattca gctccggttc ccaacgatca    3480
aggcgagtta catgatcccc catgttgtgc aaaaaagcgg ttagctcctt cggtcctccg    3540
atcgttgtca gaagtaagtt ggccgcagtg ttatcactca tggttatggc agcactgcat    3600
aattctctta ctgtcatgcc atccgtaaga tgcttttctg tgactggtga gtactcaacc    3660
aagtcattct gagaatagtg tatgcggcga ccgagttgct cttgcccggc gtcaatacgg    3720
gataataccg cgccacatag cagaacttta aaagtgctca tcattggaaa acgttcttcg    3780
gggcgaaaac tctcaaggat cttaccgctg ttgagatcca gttcgatgta acccactcgt    3840
gcacccaact gatcttcagc atcttttact ttcaccagcg tttctgggtg agcaaaaaca    3900
ggaaggcaaa atgccgcaaa aaagggaata agggcgacac ggaaatgttg aatactcata    3960
ctcttccttt ttcaatatta ttgaagcatt tatcagggtt attgtctcat gagcggatac    4020
atatttgaat gtatttagaa aaataaacaa ataggggttc cgcgcacatt tccccgaaaa    4080
gtgccacctg acgtctaaga aaccattatt atcatgacat taacctataa aataggcgt    4140 atcacgaggc cctttcgtct cgcgcgtttc ggt                                 4173

<210> SEQ ID NO 69
<211> LENGTH: 62
<212> TYPE: DNA
```

<213> ORGANISM: Artificial Sequence
<220> FEATURE:
<223> OTHER INFORMATION: primer

<400> SEQUENCE: 69
gcttataaaa ctttaactaa taattagaga ttaaatcgct taaggtttcc cgactggaaa    60
gc    62

<210> SEQ ID NO 70
<211> LENGTH: 64
<212> TYPE: DNA
<213> ORGANISM: Artificial Sequence
<220> FEATURE:
<223> OTHER INFORMATION: primer

<400> SEQUENCE: 70
ctactcataa cctcacgcaa aataacacag tcaaatcaat caaaccagtc acgacgttgt    60
aaaa    64

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
ggacgtaaag ggtagcctcc    20

<210> SEQ ID NO 72
<211> LENGTH: 22
<212> TYPE: DNA
<213> ORGANISM: Artificial Sequence
<220> FEATURE:
<223> OTHER INFORMATION: primer

<400> SEQUENCE: 72
gaagcggacc cagacttaag cc    22

<210> SEQ ID NO 73
<211> LENGTH: 70
<212> TYPE: DNA
<213> ORGANISM: Artificial Sequence
<220> FEATURE:
<223> OTHER INFORMATION: primer

<400> SEQUENCE: 73
ccctatgtct ctggccgatc acgcgccatt gtccctcaga aacaaatcaa ccagtcacga    60
cgttgtaaaa    70

<210> SEQ ID NO 74
<211> LENGTH: 70
<212> TYPE: DNA
<213> ORGANISM: Artificial Sequence
<220> FEATURE:
<223> OTHER INFORMATION: primer

<400> SEQUENCE: 74
tagaagcaac tgtgccgaca gcctctgaat gagtggtgtt gtaaccaccc aggtttcccg    60
actggaaagc    70

<210> SEQ ID NO 75
<211> LENGTH: 25

```
<212> TYPE: DNA
<213> ORGANISM: Artificial Sequence
<220> FEATURE:
<223> OTHER INFORMATION: primer

<400> SEQUENCE: 75
tcaatgagac tgttgtcctc ctact                                          25

<210> SEQ ID NO 76
<211> LENGTH: 24
<212> TYPE: DNA
<213> ORGANISM: Artificial Sequence
<220> FEATURE:
<223> OTHER INFORMATION: primer

<400> SEQUENCE: 76
tacatccttg tcgagccttg ggca                                           24

<210> SEQ ID NO 77
<211> LENGTH: 65
<212> TYPE: DNA
<213> ORGANISM: Artificial Sequence
<220> FEATURE:
<223> OTHER INFORMATION: primer

<400> SEQUENCE: 77
ccgaaatgat tccctttcct gcacaacacg agatctttca cgcatccagt cacgacgttg    60
taaaa                                                                65

<210> SEQ ID NO 78
<211> LENGTH: 64
<212> TYPE: DNA
<213> ORGANISM: Artificial Sequence
<220> FEATURE:
<223> OTHER INFORMATION: primer

<400> SEQUENCE: 78
aaagtagcct taaagctagg ctataatcat gcatcctcaa attctaggtt tcccgacgga    60
aagc                                                                 64

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
cgcaagaacg tagtatccac atgcc                                          25

<210> SEQ ID NO 80
<211> LENGTH: 21
<212> TYPE: DNA
<213> ORGANISM: Artificial Sequence
<220> FEATURE:
<223> OTHER INFORMATION: primer

<400> SEQUENCE: 80
ggatatttac agaacgatgc g                                              21

<210> SEQ ID NO 81
<211> LENGTH: 37
<212> TYPE: DNA
<213> ORGANISM: Artificial Sequence
<220> FEATURE:
```

<223> OTHER INFORMATION: primer

<400> SEQUENCE: 81
caggaattca aaacgatgac taaaatcttc gcttacg                                37

<210> SEQ ID NO 82
<211> LENGTH: 35
<212> TYPE: DNA
<213> ORGANISM: Artificial Sequence
<220> FEATURE:
<223> OTHER INFORMATION: primer

<400> SEQUENCE: 82
cgcttaagcc tcgagttaac cgaccttaac tggag                                  35

<210> SEQ ID NO 83
<211> LENGTH: 71
<212> TYPE: DNA
<213> ORGANISM: Artificial Sequence
<220> FEATURE:
<223> OTHER INFORMATION: primer

<400> SEQUENCE: 83
agtataaata aaaacccaa gtaatatagc aaaaacatat tgccaacaaa ccagtcacga        60
cgttgtaaaa c                                                            71

<210> SEQ ID NO 84
<211> LENGTH: 70
<212> TYPE: DNA
<213> ORGANISM: Artificial Sequence
<220> FEATURE:
<223> OTHER INFORMATION: primer

<400> SEQUENCE: 84
aatttattta tttgcaacaa taattcgttt ttgagtacac tactaatggc aggtttcccg       60
actggaaagc                                                              70

<210> SEQ ID NO 85
<211> LENGTH: 19
<212> TYPE: DNA
<213> ORGANISM: Artificial Sequence
<220> FEATURE:
<223> OTHER INFORMATION: primer

<400> SEQUENCE: 85
ttgtgctatt gcagtcctc                                                    19

<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86
ttgagtacac tactaatggc                                                   20

<210> SEQ ID NO 87
<211> LENGTH: 80
<212> TYPE: DNA
<213> ORGANISM: Artificial Sequence
<220> FEATURE:
<223> OTHER INFORMATION: primer

<400> SEQUENCE: 87
caactatctc atatacaatg tctatcccag aaactcaaaa aggtgttatc ttctacgaat    60
ccagtcacga cgttgtaaaa                                                80

<210> SEQ ID NO 88
<211> LENGTH: 80
<212> TYPE: DNA
<213> ORGANISM: Artificial Sequence
<220> FEATURE:
<223> OTHER INFORMATION: primer

<400> SEQUENCE: 88
ataagaaatt cgcttattta gaagtgtcaa caacgtatct accaacgatt tgacccttt    60 aggtttcccg actggaaagc                                               80

<210> SEQ ID NO 89
<211> LENGTH: 20
<212> TYPE: DNA
<213> ORGANISM: Artificial Sequence
<220> FEATURE:
<223> OTHER INFORMATION: primer

<400> SEQUENCE: 89
tcaagctata ccaagcatac                                                20

<210> SEQ ID NO 90
<211> LENGTH: 19
<212> TYPE: DNA
<213> ORGANISM: Artificial Sequence
<220> FEATURE:
<223> OTHER INFORMATION: primer

<400> SEQUENCE: 90
acctcatgct atacctgag                                                 19

<210> SEQ ID NO 91
<211> LENGTH: 64
<212> TYPE: DNA
<213> ORGANISM: Artificial Sequence
<220> FEATURE:
<223> OTHER INFORMATION: primer

<400> SEQUENCE: 91
caagaaacat ctttaacata cacaaacaca tactatcaga atacccagtc acgacgttgt    60
aaaa                                                                 64

<210> SEQ ID NO 92
<211> LENGTH: 65
<212> TYPE: DNA
<213> ORGANISM: Artificial Sequence
<220> FEATURE:
<223> OTHER INFORMATION: primer

<400> SEQUENCE: 92
gtattttgtg tatatgacgg aaagaaatgc aggttggtac attacaggtt tcccgactgg    60
aaagc                                                                65

<210> SEQ ID NO 93
<211> LENGTH: 24
<212> TYPE: DNA
<213> ORGANISM: Artificial Sequence
<220> FEATURE:
<223> OTHER INFORMATION: primer

```
<400> SEQUENCE: 93
gcatcgggaa cgtatgtaac attg                                           24

<210> SEQ ID NO 94
<211> LENGTH: 19
<212> TYPE: DNA
<213> ORGANISM: Artificial Sequence
<220> FEATURE:
<223> OTHER INFORMATION: primer

<400> SEQUENCE: 94
tgacgtaaga ccaagtaag                                                 19

<210> SEQ ID NO 95
<211> LENGTH: 55
<212> TYPE: DNA
<213> ORGANISM: Artificial Sequence
<220> FEATURE:
<223> OTHER INFORMATION: primer

<400> SEQUENCE: 95
ctatagggcg aattggctag cttatcatta tcaatactcg ccatttcaaa gaata         55

<210> SEQ ID NO 96
<211> LENGTH: 66
<212> TYPE: DNA
<213> ORGANISM: Artificial Sequence
<220> FEATURE:
<223> OTHER INFORMATION: primer

<400> SEQUENCE: 96
ctcgaggggg ggcccggtac ctcgaaacta agttctggtg ttttaaaact aaaaaaaaga    60
ctaact                                                               66

<210> SEQ ID NO 97
<211> LENGTH: 6110
<212> TYPE: DNA
<213> ORGANISM: Artificial Sequence
<220> FEATURE:
<223> OTHER INFORMATION: Synthetic pCS-Ex1 vector

<400> SEQUENCE: 97
ctaaattgta agcgttaata ttttgttaaa attcgcgtta aatttttgtt aaatcagctc    60
attttttaac caataggccg aaatcggcaa atcccttat aaatcaaaag aatagaccga    120
gatagggttg agtacgcatt taagcataaa cacgcactat gccgttcttc tcatgtatat    180
atatatacag gcaacacgca gatataggtg cgacgtgaac agtgagctgt atgtgcgcag    240
ctcgcgttgc attttcggaa gcgctcgttt tcggaaacgc tttgaagttc ctattccgaa    300
gttcctattc tctagctaga aagtatagga acttcagagc gcttttgaaa accaaaagcg    360
ctctgaagac gcactttcaa aaaccaaaa acgcaccgga ctgtaacgag ctactaaaat    420
attgcgaata ccgcttccac aaacattgct caaaagtatc tctttgctat atatctctgt    480
gctatatccc tatataacct acccatccac ctttcgctcc ttgaacttgc atctaaactc    540
gacctctaca ttttttatgt ttatctctag tattactctt tagacaaaaa aattgtagta    600
agaactattc atagagtgaa tcgaaaacaa tacgaaaatg taaacatttc ctatacgtag    660
tatatagaga caaaatagaa gaaaccgttc ataattttct gaccaatgaa gaatcatcaa    720
cgctatcact ttctgttcac aaagtatgcg caatccacat cggtatagaa tataatcggg    780
gatgccttta tcttgaaaaa atgcacccgc agcttcgcta gtaatcagta aacgcgggaa    840
```

```
gtggagtcag gcttttttta tggaagagaa aatagacacc aaagtagcct tcttctaacc    900
ttaacggacc tacagtgcaa aaagttatca agagactgca ttatagagcg cacaaaggag    960
aaaaaaagta atctaagatg ctttgttaga aaaatagcgc tctcgggatg cattttgta   1020
gaacaaaaaa gaagtataga ttctttgttg gtaaaatagc gctctcgcgt tgcatttctg   1080
ttctgtaaaa atgcagctca gattctttgt ttgaaaaatt agcgctctcg cgttgcattt   1140
ttgttttaca aaaatgaagc acagattctt cgttggtaaa atagcgcttt cgcgttgcat   1200
ttctgttctg taaaaatgca gctcagattc tttgtttgaa aaattagcgc tctcgcgttg   1260
cattttgtt ctacaaaatg aagcacagat gcttcgttaa tgtgctgcaa ggcgattaag   1320
ttgggtaacg ccagggtttt cccagtcacg acgttgtaaa acgacggcca gtgaattgta   1380
atacgactca ctatagggcg aattggctag cttatcatta tcaatactcg ccatttcaaa   1440
gaatacgtaa ataattaata gtagtgattt tcctaacttt atttagtcaa aaaattagcc   1500
ttttaattct gctgtaaccc gtacatgccc aaaatagggg gcgggttaca cagaatatat   1560
aacatcgtag gtgtctgggt gaacagttta ttcctggcat ccactaaata taatggagcc   1620
cgcttttaa gctggcatcc agaaaaaaaa agaatcccag caccaaaata ttgttttctt   1680
caccaaccat cagttcatag gtccattctc ttagcgcaac tacagagaac aggggcacaa   1740
acaggcaaaa aacgggcaca acctcaatgg agtgatgcaa cctgcctgga gtaaatgatg   1800
acacaaggca attgacccac gcatgtatct atctcatttt cttacacctt ctattacctt   1860
ctgctctctc tgatttggaa aaagctgaaa aaaaaggttg aaaccagttc cctgaaatta   1920
ttcccctact tgactaataa gtatataaag acggtaggta ttgattgtaa ttctgtaaat   1980
ctatttctta aacttcttaa attctacttt tatagttagt cttttttta gttttaaaac   2040
accagaactt agtttcgagg taccgggccc ccctcgagg tcgacggtat cgataagctt   2100
gatatcgaat tcctgcagcc cggggggatcc actagttcta gagcggccgc caccgcggtg   2160
gagctcggtt ctgcttatcc ttacgacgtg cctgactacg cctgaacccg atgcaaatga   2220
gacgatcgtc tattcctggt ccggtttcct ctgccctctc ttctattcac tttttttata   2280
ctttatataa aattatataa atgacataac tgaaacgcca cacgtcctct cctattcgtt   2340
aacgcctgtc tgtagcgctg ttactgaagc tgcgcaagta gttttttcac cgtataggcc   2400
ctcttttct ctctctttct ttctctcccg cgctgatctc ttcttcgaaa cacagagtgc   2460
accataccac ctttcaatt catcattttt tttttattct tttttttgat ttcggtttcc   2520
ttgaaatttt tttgattcgg taatctccga acagaaggaa gaacgaagga aggagcacag   2580
acttagattg gtatatatac gcatatgtag tgttgaagaa acatgaaatt gcccagtatt   2640
cttaacccaa ctgcacagaa caaaaacctc caggaaacga agataaatca tgtcgaaagc   2700
tacatataag gaacgtgctg ctactcatcc tagtcctgtt gctgccaagc tatttaatat   2760
catgcacgaa aagcaaacaa acttgtgtgc ttcattggat gttcgtacca ccaaggaatt   2820
actggagtta gttgaagcat taggtcccaa aatttgttta ctaaaacac atgtggatat   2880
cttgactgat ttttccatgg agggcacagt taagccgcta aaggcattat ccgccaagta   2940
caatttttta ctcttcgaag acagaaaatt tgctgacatt ggtaatacag tcaaattgca   3000
gtactctgcg ggtgtataca gaatagcaga atgggcagac attacgaatg cacacggtgt   3060
ggtgggccca ggtattgtta gcggtttgaa gcaggcggca gaagaagtaa caaaggaacc   3120
tagaggcctt ttgatgttag cagaattgtc atgcaagggc tccctatcta ctggagaata   3180
```

```
tactaagggt actgttgaca ttgcgaagag cgacaaagat tttgttatcg gctttattgc    3240
tcaaagagac atgggtggaa gagatgaagg ttacgattgg ttgattatga cacccggtgt    3300
gggtttagat gacaagggag acgcattggg tcaacagtat agaaccgtgg atgatgtggt    3360
ctctacagga tctgacatta ttattgttgg aagaggacta tttgcaaagg aagggatgc    3420 taaggtagag ggtgaacgtt acagaaaagc aggctgggaa gcatatttga gaagatgcgg    3480
ccagcaaaac taatcatgta attagttatg tcacgcttac attcacgccc tcccccaca    3540 tccgctctaa ccgaaaagga aggagttaga caacctgaag tctaggtccc tatttatttt    3600
tttatagtta tgttagtatt aagaacgtta tttatatttc aaatttttct ttttttctg    3660 tacagacgcg tgtacgcatg taacattata ctgaaaacct tgcttgagaa ggttttggga    3720
cgctcgaagg ctttaatttg cgtctgtagc gctgttactg aagctgcgca agtagttttt    3780
tcaccgtata ggccctcttt ttctctctct ttctttctct cccgcgctga tctcttcttc    3840
gaaacatcat gaataaaaag aaaaaggaaa tcaagaaaaa aaagccataa tttatcccac    3900 atttttttt attgtcgctg ttcacaccgc ataacgaaga tattggctag ctaaccagct    3960
tttgttccct ttagtgaggg ttaatttcga gcttggcgta atcatggtca tagctgtttc    4020
ctgtgtgaaa ttgttatccg ctcacaattc cacacaacat acgagccgga agcataaagt    4080
gtaaagcctg gggtgcctaa tgagtgagct aactcacatt aattgcgttg cgctcactgc    4140
ccgctttcca gtcgggaaac ctgtcgtgcc agctgcatta atgaatcggc caacgcgcgg    4200
ggagaggcgg tttgcgtatt gggcgctctt ccgcttcctc gctcactgac tcgctgcgct    4260
cggtcgttcg gctgcggcga gcggtatcag ctcactcaaa ggcggtaata cggttatcca    4320
cagaatcagg ggataacgca ggaaagaaca tgtgagcaaa aggccagcaa aaggccagga    4380
accgtaaaaa ggccgcgttg ctggcgtttt tccataggct ccgcccccct gacgagcatc    4440
acaaaaatcg acgctcaagt cagaggtggc gaaacccgac aggactataa agataccagg    4500
cgtttccccc tggaagctcc ctcgtgcgct ctcctgttcc gaccctgccg cttaccggat    4560
acctgtccgc ctttctccct tcgggaagcg tggcgctttc tcatagctca cgctgtaggt    4620
atctcagttc ggtgtaggtc gttcgctcca agctgggctg tgtgcacgaa ccccccgttc    4680
agcccgaccg ctgcgcctta tccggtaact atcgtcttga gtccaacccg gtaagacacg    4740
acttatcgcc actggcagca gccactggta acaggattag cagagcgagg tatgtaggcg    4800
gtgctacaga gttcttgaag tggtggccta actacggcta cactagaagg acagtatttg    4860
gtatctgcgc tctgctgaag ccagttacct tcggaaaaag agttggtagc tcttgatccg    4920
gcaaacaaac caccgctggt agcggtggtt tttttgtttg caagcagcag attacgcgca    4980
gaaaaaaagg atctcaagaa gatcctttga tcttttctac ggggtctgac gctcagtgga    5040
acgaaaactc acgttaaggg attttggtca tgagattatc aaaaaggatc ttcacctaga    5100
tccttttaaa ttaaaaatga agttttaaat caatctaaag tatatatgag taaacttggt    5160
ctgacatcag aagaactcgt caagaaggcg atagaaggcg atgcgctgcg aatcgggagc    5220
ggcgataccg taaagcacga ggaagcggtc agcccattcg ccgccaagct cttcagcaat    5280
atcacgggta gccaacgcta tgtcctgata gcggtccgcc acacccagcc ggccacagtc    5340
gatgaatcca gaaaagcggc cattttccac catgatattc ggcaagcagg catcgccatg    5400
ggtcacgacg agatcctcgc cgtcgggcat gctcgccttg agcctggcga acagttcggc    5460
tggcgcgagc ccctgatgct cttcgtccag atcatcctga tcgacaagac cggcttccat    5520
ccgagtacgt gctcgctcga tgcgatgttt cgcttggtgg tcgaatgggc aggtagccgg    5580
```

```
atcaagcgta tgcagccgcc gcattgcatc agccatgatg gatactttct cggcaggagc    5640
aaggtgagat gacaggagat cctgccccgg cacttcgccc aatagcagcc agtcccttcc    5700
cgcttcagtg acaacgtcga gcacagctgc gcaaggaacg cccgtcgtgg ccagccacga    5760
tagccgcgct gcctcgtctt gcagttcatt cagggcaccg gacaggtcgg tcttgacaaa    5820
aagaaccggg cgcccctgcg ctgacagccg gaacacggcg gcatcagagc agccgattgt    5880
ctgttgtgcc cagtcatagc cgaatagcct ctccacccaa gcggccggag aacctgcgtg    5940
caatccatct tgttcaattc gagtgcattc aacatcagcc atactcttcc tttttcaata    6000
ttattgaagc atttatcagg gttattgtct catgagcgga tacatatttg aatgtattta    6060
gaaaaataaa caaatagggg ttccgcgcac atttccccga aaagtgccac                6110

<210> SEQ ID NO 98
<211> LENGTH: 55
<212> TYPE: DNA
<213> ORGANISM: Artificial Sequence
<220> FEATURE:
<223> OTHER INFORMATION: primer

<400> SEQUENCE: 98
accagaactt agtttcgaga aacaatgaat caacaggata ttgaacaggt ggtga          55

<210> SEQ ID NO 99
<211> LENGTH: 50
<212> TYPE: DNA
<213> ORGANISM: Artificial Sequence
<220> FEATURE:
<223> OTHER INFORMATION: primer

<400> SEQUENCE: 99
gtaaggataa gcagaaccgt taaacaatgc gaaacgcatc gactaataca               50

<210> SEQ ID NO 100
<211> LENGTH: 7413
<212> TYPE: DNA
<213> ORGANISM: Artificial Sequence
<220> FEATURE:
<223> OTHER INFORMATION: Synthetic MD1040 vector

<400> SEQUENCE: 100
ctaaattgta agcgttaata ttttgttaaa attcgcgtta aattttttgtt aaatcagctc    60 attttttaac caataggccg aaatcggcaa atcccttat aaatcaaaag aatagaccga    120
gatagggttg agtacgcatt taagcataaa cacgcactat gccgttcttc tcatgtatat    180
atatatacag gcaacacgca gatataggtg cgacgtgaac agtgagctgt atgtgcgcag    240
ctcgcgttgc atttcggaa gcgctcgttt tcggaaacgc tttgaagttc ctattccgaa    300
gttcctattc tctagctaga aagtatagga acttcagagc gcttttgaaa accaaaagcg    360
ctctgaagac gcactttcaa aaaaccaaaa acgcaccgga ctgtaacgag ctactaaaat    420
attgcgaata ccgcttccac aaacattgct caaaagtatc tctttgctat atatctctgt    480
gctatatccc tatataacct acccatccac ctttcgctcc ttgaacttgc atctaaactc    540
gacctctaca ttttttatgt ttatctctag tattactctt tagacaaaaa aattgtagta    600
agaactattc atagagtgaa tcgaaaacaa tacgaaaatg taaacatttc ctatacgtag    660
tatatagaga caaaatagaa gaaaccgttc ataattttct gaccaatgaa gaatcatcaa    720
cgctatcact ttctgttcac aaagtatgcg caatccacat cggtatagaa tataatcggg    780
```

```
gatgccttta tcttgaaaaa atgcacccgc agcttcgcta gtaatcagta aacgcgggaa    840
gtggagtcag gctttttta tggaagagaa aatagacacc aaagtagcct tcttctaacc    900
ttaacggacc tacagtgcaa aaagttatca agagactgca ttatagagcg cacaaaggag    960
aaaaaaagta atctaagatg ctttgttaga aaaatagcgc tctcgggatg cattttgta    1020 gaacaaaaaa gaagtataga ttctttgttg gtaaaatagc gctctcgcgt tgcatttctg    1080
ttctgtaaaa atgcagctca gattctttgt ttgaaaaatt agcgctctcg cgttgcattt    1140
ttgttttaca aaatgaagc acagattctt cgttggtaaa atagcgcttt cgcgttgcat    1200
ttctgttctg taaaaatgca gctcagattc tttgtttgaa aaattagcgc tctcgcgttg    1260 cattttgtt ctacaaaatg aagcacagat gcttcgttaa tgtgctgcaa ggcgattaag    1320
ttgggtaacg ccagggtttt cccagtcacg acgttgtaaa acgacggcca gtgaattgta    1380
atacgactca ctatagggcg aattggctag cttatcatta tcaatactcg ccatttcaaa    1440
gaatacgtaa ataattaata gtagtgattt tcctaacttt atttagtcaa aaaattagcc    1500
ttttaattct gctgtaaccc gtacatgccc aaaataggg gcgggttaca cagaatatat    1560
aacatcgtag gtgtctgggt gaacagttta ttcctggcat ccactaaata taatggagcc    1620 cgcttttaa gctggcatcc agaaaaaaaa agaatcccag caccaaaata ttgttttctt    1680
caccaaccat cagttcatag gtccattctc ttagcgcaac tacagagaac aggggcacaa    1740
acaggcaaaa acgggcaca acctcaatgg agtgatgcaa cctgcctgga gtaaatgatg    1800
acacaaggca attgacccac gcatgtatct atctcatttt cttacacctt ctattacctt    1860
ctgctctctc tgatttggaa aaagctgaaa aaaaaggttg aaaccagttc cctgaaatta    1920
ttcccctact tgactaataa gtatataaag acggtaggta ttgattgtaa ttctgtaaat    1980 ctattctta aacttcttaa attctacttt tatagttagt ctttttta gttttaaaac    2040 accagaactt agtttcgaga acaatgaat caacaggata ttgaacaggt ggtgaaagcg    2100
gtactgctga aaatgcaaag cagtgacacg ccgtccgccg ccgttcatga gatgggcgtt    2160
ttcgcgtccc tggatgacgc cgttgcggca gccaaagtcg cccagcaagg gttaaaaagc    2220
gtggcaatgc gccagttagc cattgctgcc attcgtgaag caggcgaaaa acacgccaga    2280
gatttagcgg aacttgccgt cagtgaaacc ggcatggggc gcgttgaaga taaatttgca    2340
aaaaacgtcg ctcaggcgcg cggcacacca ggcgttgagt gcctctctcc gcaagtgctg    2400
actggcgaca acggcctgac cctaattgaa aacgcaccct ggggcgtggt ggcttcggtg    2460
acgccttcca ctaacccggc ggcaaccgta attaacaacg ccatcagcct gattgccgcg    2520
ggcaacagcg tcatttttgc cccgcatccg gcggcgaaaa agtctcccca gcgggcgatt    2580
acgctgctca accaggcgat tgttgccgca ggtgggccgg aaaacttact ggttactgtg    2640
gcaaatccgg atatcgaaac cgcgcaacgc ttgttcaagt ttccgggtat cggcctgctg    2700
gtggtaaccg gcggcgaagc ggtagtagaa gcggcgcgta acacaccaa taaacgtctg    2760 attgccgcag gcgctggcaa cccgccggta gtggtggatg aaaccgccga cctcgcccgt    2820
gccgctcagt ccatcgtcaa aggcgcttct ttcgataaca acatcatttg tgccgacgaa    2880
aaggtactga ttgttgttga tagcgtagcc gatgaactga tgcgtctgat ggaaggccag    2940
cacgcggtga aactgaccgc agaacaggcg cagcagctgc aaccggtgtt gctgaaaaat    3000
atcgacgagc gcggaaaagg caccgtcagc cgtgactggg ttggtcgcga cgcaggcaaa    3060 atcgcggcg caatcggcct taaagttccg caagaaacgc gcctgctgtt tgtggaaacc    3120
accgcagaac atccgtttgc cgtgactgaa ctgatgatgc cggtgttgcc gtcgtgcgc    3180
```

```
gtcgccaacg tggcggatgc cattgcgcta gcggtgaaac tggaaggcgg ttgccaccac   3240
acggcggcaa tgcactcgcg caacatcgaa aacatgaacc agatggcgaa tgctattgat   3300
accagcattt tcgttaagaa cggaccgtgc attgccgggc tggggctggg cggggaaggc   3360
tggaccacca tgaccatcac cacgccaacc ggtgaagggg taaccagcgc gcgtacgttt   3420
gtccgtctgc gtcgctgtgt attagtcgat gcgtttcgca ttgtttaacg gttctgctta   3480
tccttacgac gtgcctgact acgcctgaac ccgatgcaaa tgagacgatc gtctattcct   3540
ggtccggttt tctctgccct ctcttctatt cactttttt atactttata taaaattata   3600
taaatgacat aactgaaacg ccacacgtcc tctcctattc gttaacgcct gtctgtagcg   3660
ctgttactga agctgcgcaa gtagtttttt caccgtatag gccctctttt tctctctctt   3720
tctttctctc ccgcgctgat ctcttcttcg aaacacagag tgcaccatac cacctttca   3780 attcatcatt ttttttttat tcttttttt gatttcggtt tccttgaaat ttttttgatt   3840
cggtaatctc cgaacagaag gaagaacgaa ggaaggagca cagacttaga ttggtatata   3900
tacgcatatg tagtgttgaa gaaacatgaa attgcccagt attcttaacc caactgcaca   3960
gaacaaaaac ctccaggaaa cgaagataaa tcatgtcgaa agctacatat aaggaacgtg   4020
ctgctactca tcctagtcct gttgctgcca agctatttaa tatcatgcac gaaaagcaaa   4080
caaacttgtg tgcttcattg gatgttcgta ccaccaagga attactggag ttagttgaag   4140
cattaggtcc caaaatttgt ttactaaaaa cacatgtgga tatcttgact gattttcca   4200 tggagggcac agttaagccg ctaaaggcat tatccgccaa gtacaatttt ttactcttcg   4260
aagacagaaa atttgctgac attggtaata cagtcaaatt gcagtactct gcgggtgtat   4320
acagaatagc agaatgggca gacattacga atgcacacgg tgtggtgggc ccaggtattg   4380
ttagcggttt gaagcaggcg gcagaagaag taacaaagga acctagaggc cttttgatgt   4440
tagcagaatt gtcatgcaag ggctccctat ctactggaga atatactaag ggtactgttg   4500
acattgcgaa gagcgacaaa gattttgtta tcggctttat tgctcaaaga gacatgggtg   4560
gaagagatga aggttacgat tggttgatta tgacacccgg tgtgggttta gatgacaagg   4620
gagacgcatt gggtcaacag tatagaaccg tggatgatgt ggtctctaca ggatctgaca   4680
ttattattgt tggaagagga ctatttgcaa agggaaggga tgctaaggta gagggtgaac   4740
gttacagaaa agcaggctgg gaagcatatt tgagaagatg cggccagcaa aactaatcat   4800
gtaattagtt atgtcacgct tacattcacg ccctcccccc acatccgctc taaccgaaaa   4860
ggaaggagtt agacaacctg aagtctaggt ccctatttat ttttttatag ttatgttagt   4920
attaagaacg ttatttatat ttcaaatttt tcttttttt ctgtacagac gcgtgtacgc   4980
atgtaacatt atactgaaaa ccttgcttga aaggttttg gacgctcga aggctttaat   5040 ttgcgtctgt agcgctgtta ctgaagctgc gcaagtagtt ttttcaccgt ataggccctc   5100 ttttctctc tctttctttc tctcccgcgc tgatctcttc ttcgaaacat catgaataaa   5160
aagaaaaagg aaatcaagaa aaaaaagcca taatttatcc cacatttttt tttattgtcg   5220
ctgttcacac cgcataacga agatattggc tagctaacca gcttttgttc cctttagtga   5280
gggttaattt cgagcttggc gtaatcatgg tcatagctgt ttcctgtgtg aaattgttat   5340
ccgctcacaa ttccacacaa catacgagcc ggaagcataa agtgtaaagc ctggggtgcc   5400
taatgagtga gctaactcac attaattgcg ttgcgctcac tgcccgcttt ccagtcggga   5460
aacctgtcgt gccagctgca ttaatgaatc ggccaacgcg cggggagagg cggtttgcgt   5520
```

```
attgggcgct cttccgcttc ctcgctcact gactcgctgc gctcggtcgt tcggctgcgg      5580
cgagcggtat cagctcactc aaaggcggta atacggttat ccacagaatc aggggataac      5640
gcaggaaaga acatgtgagc aaaaggccag caaaaggcca ggaaccgtaa aaaggccgcg      5700
ttgctggcgt ttttccatag gctccgcccc cctgacgagc atcacaaaaa tcgacgctca      5760
agtcagaggt ggcgaaaccc gacaggacta taaagatacc aggcgtttcc ccctggaagc      5820
tccctcgtgc gctctcctgt tccgaccctg ccgcttaccg gatacctgtc cgcctttctc      5880
ccttcgggaa gcgtggcgct ttctcatagc tcacgctgta ggtatctcag ttcggtgtag      5940
gtcgttcgct ccaagctggg ctgtgtgcac gaaccccccg ttcagcccga ccgctgcgcc      6000
ttatccggta actatcgtct tgagtccaac ccggtaagac acgacttatc gccactggca      6060
gcagccactg gtaacaggat tagcagagcg aggtatgtag gcggtgctac agagttcttg      6120
aagtggtggc ctaactacgg ctacactaga aggacagtat ttggtatctg cgctctgctg      6180
aagccagtta ccttcggaaa aagagttggt agctcttgat ccggcaaaca aaccaccgct      6240
ggtagcggtg gtttttttgt ttgcaagcag cagattacgc gcagaaaaaa aggatctcaa      6300
gaagatcctt tgatctttc tacggggtct gacgctcagt ggaacgaaaa ctcacgttaa      6360
gggattttgg tcatgagatt atcaaaaagg atcttcacct agatcctttt aaattaaaaa      6420
tgaagtttta aatcaatcta agtatatat gagtaaactt ggtctgacat cagaagaact      6480
cgtcaagaag gcgatagaag gcgatgcgct gcgaatcggg agcggcgata ccgtaaagca      6540
cgaggaagcg gtcagcccat cgccgccaa gctcttcagc aatatcacgg gtagccaacg      6600
ctatgtcctg atagcggtcc gccacaccca gccggccaca gtcgatgaat ccagaaaagc      6660
ggccattttc caccatgata ttcggcaagc aggcatcgcc atgggtcacg acgagatcct      6720
cgccgtcggg catgctcgcc ttgagcctgg cgaacagttc ggctggcgcg agccctgat      6780 gctcttcgtc cagatcatcc tgatcgacaa gaccggcttc catccgagta cgtgctcgct      6840
cgatgcgatg tttcgcttgg tggtcgaatg gcaggtagc cggatcaagc gtatgcagcc      6900
gccgcattgc atcagccatg atggatactt tctcggcagg agcaaggtga gatgacagga      6960
gatcctgccc cggcacttcg cccaatagca gccagtccct tcccgcttca gtgacaacgt      7020
cgagcacagc tgcgcaagga acgcccgtcg tggccagcca cgatagccgc gctgcctcgt      7080
cttgcagttc attcagggca ccggacaggt cggtcttgac aaaaagaacc gggcgcccct      7140
gcgctgacag ccggaacacg gcggcatcag agcagccgat tgtctgttgt gcccagtcat      7200
agccgaatag cctctccacc caagcggccg gagaacctgc gtgcaatcca tcttgttcaa      7260
ttcgagtgca ttcaacatca gccatactct tccttttca atattattga agcatttatc      7320
agggttattg tctcatgagc ggatacatat ttgaatgtat ttagaaaaat aaacaaatag      7380
gggttccgcg cacatttccc cgaaaagtgc cac                                   7413
```

<210> SEQ ID NO 101
<211> LENGTH: 59
<212> TYPE: DNA
<213> ORGANISM: Artificial Sequence
<220> FEATURE:
<223> OTHER INFORMATION: primer

<400> SEQUENCE: 101

```
aatcttgtgc tattgcagtc ctctttata tacagtataa tacgactcac tatagggcg       59
```

<210> SEQ ID NO 102
<211> LENGTH: 60

```
<212> TYPE: DNA
<213> ORGANISM: Artificial Sequence
<220> FEATURE:
<223> OTHER INFORMATION: primer

<400> SEQUENCE: 102
atgcgaattg cgtaattcac ggcgataacg tagtattaat taaccctcac taaagggaac    60

<210> SEQ ID NO 103
<211> LENGTH: 19
<212> TYPE: DNA
<213> ORGANISM: Artificial Sequence
<220> FEATURE:
<223> OTHER INFORMATION: primer

<400> SEQUENCE: 103
gcccacaact tatcaagtg                                                  19

<210> SEQ ID NO 104
<211> LENGTH: 19
<212> TYPE: DNA
<213> ORGANISM: Artificial Sequence
<220> FEATURE:
<223> OTHER INFORMATION: primer

<400> SEQUENCE: 104
ttataagaca agcgcaggg                                                  19

<210> SEQ ID NO 105
<211> LENGTH: 19
<212> TYPE: DNA
<213> ORGANISM: Artificial Sequence
<220> FEATURE:
<223> OTHER INFORMATION: primer

<400> SEQUENCE: 105
gcccacaact tatcaagtg                                                  19

<210> SEQ ID NO 106
<211> LENGTH: 19
<212> TYPE: DNA
<213> ORGANISM: Artificial Sequence
<220> FEATURE:
<223> OTHER INFORMATION: primer

<400> SEQUENCE: 106
ttataagaca agcgcaggg                                                  19

<210> SEQ ID NO 107
<211> LENGTH: 52
<212> TYPE: DNA
<213> ORGANISM: Artificial Sequence
<220> FEATURE:
<223> OTHER INFORMATION: primer

<400> SEQUENCE: 107
aacactatat caatagaaac aatgtcagta aacccagaat ttatagccga tg             52

<210> SEQ ID NO 108
<211> LENGTH: 49
<212> TYPE: DNA
<213> ORGANISM: Artificial Sequence
<220> FEATURE:
<223> OTHER INFORMATION: primer

<400> SEQUENCE: 108
```
aggataagca gaaccgttac cagaagaata tcttgttctt ccttcttcg            49

<210> SEQ ID NO 109
<211> LENGTH: 79
<212> TYPE: DNA
<213> ORGANISM: Artificial Sequence
<220> FEATURE:
<223> OTHER INFORMATION: primer

<400> SEQUENCE: 109
aataagaagt ttggtaatat tcaattcgaa gtgttcagtc ttttacttct cttgttttaa    60
tacgactcac tatagggcg                                                79

<210> SEQ ID NO 110
<211> LENGTH: 79
<212> TYPE: DNA
<213> ORGANISM: Artificial Sequence
<220> FEATURE:
<223> OTHER INFORMATION: primer

<400> SEQUENCE: 110
atatgaaagt attttgtgta tatgacggaa agaaatgcag gttggtacat tacaacaatt    60
aaccctcact aaagggaac                                                79

<210> SEQ ID NO 111
<211> LENGTH: 22
<212> TYPE: DNA
<213> ORGANISM: Artificial Sequence
<220> FEATURE:
<223> OTHER INFORMATION: primer

<400> SEQUENCE: 111
tatgcatcca gcttctatat cg                                            22

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
ccttaggcat ttgcctagag                                               20

<210> SEQ ID NO 113
<211> LENGTH: 45
<212> TYPE: DNA
<213> ORGANISM: Artificial Sequence
<220> FEATURE:
<223> OTHER INFORMATION: primer

<400> SEQUENCE: 113
gtaccgggcc ccccctcgaa aaacgatggc tggtcaagtg ttgga                   45

<210> SEQ ID NO 114
<211> LENGTH: 43
<212> TYPE: DNA
<213> ORGANISM: Artificial Sequence
<220> FEATURE:
<223> OTHER INFORMATION: primer

<400> SEQUENCE: 114
accgcggtgg cggccgctct agttagaaca ggccatcgat ctc                     43

```
<210> SEQ ID NO 115
<211> LENGTH: 69
<212> TYPE: DNA
<213> ORGANISM: Artificial Sequence
<220> FEATURE:
<223> OTHER INFORMATION: primer

<400> SEQUENCE: 115
atgacacaga ctgataatcc tgtccccaac tgcggtttac tgcccgagca acggccagtg      60
aattgtaat                                                             69

<210> SEQ ID NO 116
<211> LENGTH: 70
<212> TYPE: DNA
<213> ORGANISM: Artificial Sequence
<220> FEATURE:
<223> OTHER INFORMATION: primer

<400> SEQUENCE: 116
ttaaattacc atagtgctaa tattttctag gcggtttctg aaatactcaa ctaaagggaa      60
caaaagctgg                                                            70

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
ggacagcaaa tttcgagaat                                                 20

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
gtattaggaa aagagaggct                                                 20

<210> SEQ ID NO 119
<211> LENGTH: 69
<212> TYPE: DNA
<213> ORGANISM: Artificial Sequence
<220> FEATURE:
<223> OTHER INFORMATION: primer

<400> SEQUENCE: 119
atgacacaga ctgataatcc tgtccccaac tgcggtttac tgcccgagcc cagtcacgac      60
gttgtaaaa                                                             69

<210> SEQ ID NO 120
<211> LENGTH: 70
<212> TYPE: DNA
<213> ORGANISM: Artificial Sequence
<220> FEATURE:
<223> OTHER INFORMATION: primer

<400> SEQUENCE: 120
ttaaattacc atagtgctaa tattttctag gcggtttctg aaatactcaa aggtttcccg      60
actggaaagc                                                            70
```

<210> SEQ ID NO 121
<211> LENGTH: 45
<212> TYPE: DNA
<213> ORGANISM: Artificial Sequence
<220> FEATURE:
<223> OTHER INFORMATION: primer

<400> SEQUENCE: 121
gtaccgggcc cccctcgaa aaacgatgcc ttacactcta tccga          45

<210> SEQ ID NO 122
<211> LENGTH: 44
<212> TYPE: DNA
<213> ORGANISM: Artificial Sequence
<220> FEATURE:
<223> OTHER INFORMATION: primer

<400> SEQUENCE: 122
accgcggtgg cggccgctct agttacacag ccaatgggta ttcg           44

<210> SEQ ID NO 123
<211> LENGTH: 45
<212> TYPE: DNA
<213> ORGANISM: Artificial Sequence
<220> FEATURE:
<223> OTHER INFORMATION: primer

<400> SEQUENCE: 123
gtaccgggcc cccctcgaa aaacgatgtc gaagcctggt cgtac          45

<210> SEQ ID NO 124
<211> LENGTH: 43
<212> TYPE: DNA
<213> ORGANISM: Artificial Sequence
<220> FEATURE:
<223> OTHER INFORMATION: primer

<400> SEQUENCE: 124
accgcggtgg cggccgctct agctattttt ctttagacag ttc            43

<210> SEQ ID NO 125
<211> LENGTH: 43
<212> TYPE: DNA
<213> ORGANISM: Artificial Sequence
<220> FEATURE:
<223> OTHER INFORMATION: primer

<400> SEQUENCE: 125
accgcggtgg cggccgctct agttatactg aaaaccttgc ttg            43

<210> SEQ ID NO 126
<211> LENGTH: 46
<212> TYPE: DNA
<213> ORGANISM: Artificial Sequence
<220> FEATURE:
<223> OTHER INFORMATION: primer

<400> SEQUENCE: 126
gtaccgggcc cccctcgaa aaacgatgaa aactgataga ttactg         46

<210> SEQ ID NO 127
<211> LENGTH: 45
<212> TYPE: DNA
<213> ORGANISM: Artificial Sequence
<220> FEATURE:
<223> OTHER INFORMATION: primer

<400> SEQUENCE: 127
accgcggtgg cggccgctct agttagattg caaaatgagc ctgac                    45

<210> SEQ ID NO 128
<211> LENGTH: 47
<212> TYPE: DNA
<213> ORGANISM: Artificial Sequence
<220> FEATURE:
<223> OTHER INFORMATION: primer

<400> SEQUENCE: 128
gtaccgggcc ccccctcgaa aaacgatgag ttcatcagca gatttcg                  47

<210> SEQ ID NO 129
<211> LENGTH: 44
<212> TYPE: DNA
<213> ORGANISM: Artificial Sequence
<220> FEATURE:
<223> OTHER INFORMATION: primer

<400> SEQUENCE: 129
accgcggtgg cggccgctct agttaatcat tatcagtctg tctc                     44

<210> SEQ ID NO 130
<211> LENGTH: 30
<212> TYPE: DNA
<213> ORGANISM: Artificial Sequence
<220> FEATURE:
<223> OTHER INFORMATION: primer

<400> SEQUENCE: 130
tagtggatcc atgacccacg aatcatcttc                                     30

<210> SEQ ID NO 131
<211> LENGTH: 28
<212> TYPE: DNA
<213> ORGANISM: Artificial Sequence
<220> FEATURE:
<223> OTHER INFORMATION: primer

<400> SEQUENCE: 131
ggtcgactta gatacccgcc tcaaagtc                                       28

<210> SEQ ID NO 132
<211> LENGTH: 28
<212> TYPE: DNA
<213> ORGANISM: Artificial Sequence
<220> FEATURE:
<223> OTHER INFORMATION: primer

<400> SEQUENCE: 132
tggagctcct ttcctctttt tattaacc                                       28

<210> SEQ ID NO 133
<211> LENGTH: 28
<212> TYPE: DNA
<213> ORGANISM: Artificial Sequence
<220> FEATURE:
<223> OTHER INFORMATION: primer

<400> SEQUENCE: 133
gttctagaat ttgttgtaaa aagtagat                                       28

<210> SEQ ID NO 134

<211> LENGTH: 798
<212> TYPE: DNA
<213> ORGANISM: Artificial Sequence
<220> FEATURE:
<223> OTHER INFORMATION: Synthetic PGK promoter

<400> SEQUENCE: 134

```
ctttcctctt tttattaacc ttaattttta ttttagattc ctgacttcaa ctcaagacgc      60
acagatatta taacatctgc ataataggca tttgcaagaa ttactcgtga gtaaggaaag     120
agtgaggaac tatcgcatac ctgcatttaa agatgccgat ttgggcgcga atcctttatt     180
ttggcttcac cctcatacta ttatcagggc cagaaaaagg aagtgtttcc ctccttcttg     240
aattgatgtt accctcataa agcacgtggc ctcttatcga gaagaaatt accgtcgctc      300
gtgatttgtt tgcaaaaaga acaaaactga aaaaacccag acacgctcga cttcctgtct     360
tcctattgat tgcagcttcc aatttcgtca cacaacaagg tcctagcgac ggctcacagg     420
ttttgtaaca agcaatcgaa ggttctggaa tggcgggaaa gggtttagta ccacatgcta     480
tgatgcccac tgtgatctcc agagcaaagt tcgttcgatc gtactgttac tctctctctt     540
tcaaacagaa ttgtccgaat cgtgtgacaa caacagcctg ttctcacaca ctcttttctt     600
ctaaccaagg gggtggttta gtttagtaga acctcgtgaa acttacattt acatatatat     660
aaacttgcat aaattggtca atgcaagaaa tacatatttg gtcttttcta attcgtagtt     720
tttcaagttc ttagatgctt tcttttctc tttttacag atcatcaagg aagtaattat       780
ctactttta caacaaat                                                    798
```

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135

```
cgaagagctc gcaaattaaa gccttcgagc                                       30
```

<210> SEQ ID NO 136
<211> LENGTH: 37
<212> TYPE: DNA
<213> ORGANISM: Artificial Sequence
<220> FEATURE:
<223> OTHER INFORMATION: primer

<400> SEQUENCE: 136

```
ttccagtcgg gaaacctatt taaactgtga ggacctt                               37
```

<210> SEQ ID NO 137
<211> LENGTH: 20
<212> TYPE: DNA
<213> ORGANISM: Artificial Sequence
<220> FEATURE:
<223> OTHER INFORMATION: primer

<400> SEQUENCE: 137

```
ttttagttta tgtatgtgtt                                                  20
```

<210> SEQ ID NO 138
<211> LENGTH: 20
<212> TYPE: DNA
<213> ORGANISM: Artificial Sequence
<220> FEATURE:
<223> OTHER INFORMATION: primer

```
<400> SEQUENCE: 138
ccagtcacga cgttgtaaaa                                                    20

<210> SEQ ID NO 139
<211> LENGTH: 38
<212> TYPE: DNA
<213> ORGANISM: Artificial Sequence
<220> FEATURE:
<223> OTHER INFORMATION: primer

<400> SEQUENCE: 139
ggtcctcaca gtttaaatag gtttcccgac tggaaagc                                38

<210> SEQ ID NO 140
<211> LENGTH: 1743
<212> TYPE: DNA
<213> ORGANISM: Artificial Sequence
<220> FEATURE:
<223> OTHER INFORMATION: Synthetic URA cassette

<400> SEQUENCE: 140
ccagtcacga cgttgtaaaa cgacggccag tgaattcgag ctcggtacct cgcgaatgca        60
tctagatatc ggatcccgac gagctgcacc gcggtggcgg ccgtatcttt acccatacg       120 atgttcctga ctatgcgggc tatccctatg acgtcccgga ctatgcagga tcctatccat      180
atgacgttcc agattacgct gctcagtcg gccgcctgag agtgcaccat accacagctt       240
ttcaattcaa ttcatcattt ttttttttatt cttttttttg atttcggttt ctttgaaatt     300
tttttgattc ggtaatctcc gaacagaagg aagaacgaag gaaggagcac agacttagat      360
tggtatatat acgcatatgt agtgttgaag aaacatgaaa ttgcccagta ttcttaaccc      420
aactgcacag aacaaaaacc tgcaggaaac gaagataaat catgtcgaaa gctacatata     480
aggaacgtgc tgctactcat cctagtcctg ttgctgccaa gctatttaat atcatgcacg     540
aaaagcaaac aaacttgtgt gcttcattgg atgttcgtac caccaaggaa ttactggagt     600
tagttgaagc attaggtccc aaaatttgtt tactaaaaac acatgtggat atcttgactg     660 attttttccat ggagggcaca gttaagccgc taaaggcatt atccgccaag tacaattttt    720
tactcttcga agacagaaaa tttgctgaca ttggtaatac agtcaaattg cagtactctg     780
cgggtgtata cagaatagca gaatgggcag acattacgaa tgcacacggt gtggtgggcc    840
caggtattgt tagcggtttg aagcaggcgg cagaagaagt aacaaaggaa cctagaggcc      900
ttttgatgtt agcagaattg tcatgcaagg ctccctatc tactggagaa tatactaagg     960
gtactgttga cattgcgaag agcgacaaag attttgttat cggctttatt gctcaaagag    1020
acatgggtgg aagagatgaa ggttacgatt ggttgattat gacacccggt gtgggtttag    1080
atgacaaggg agacgcattg ggtcaacagt atagaaccgt ggatgatgtg gtctctacag    1140
gatctgacat tattattgtt ggaagaggac tatttgcaaa gggaagggat gctaaggtag    1200
agggtgaacg ttacagaaaa gcaggctggg aagcatattt gagaagatgc ggccagcaaa    1260
actaaaaaac tgtattataa gtaaatgcat gtatactaaa ctcacaaatt agagcttcaa    1320
tttaattata tcagttatta ccctatgcgg tgtgaaatac cgcacagatg cgtaaggaga    1380
aaataccgca tcaggaaatt gtagcggccg cgaatttgag cttatctttt acccatacga    1440
tgttcctgac tatgcgggct atccctatga cgtcccggac tatgcaggat cctatccata    1500
tgacgttcca gattacgcta ctagcggggg gcccggtgac gggcccgtcg actgcagagg    1560
```

```
cctgcatgca agcttggcgt aatcatggtc atagctgttt cctgtgtgaa attgttatcc    1620
gctcacaatt ccacacaaca tacgagccgg aagcataaag tgtaaagcct ggggtgccta    1680
atgagtgagc taactcacat taattgcgtt gcgctcactg cccgctttcc agtcgggaaa    1740
cct                                                                  1743

<210> SEQ ID NO 141
<211> LENGTH: 2243
<212> TYPE: DNA
<213> ORGANISM: Artificial Sequence
<220> FEATURE:
<223> OTHER INFORMATION: Synthetic URA cassette + TPI promoter

<400> SEQUENCE: 141
ccagtcacga cgttgtaaaa cgacggccag tgaattcgag ctcggtacct cgcgaatgca      60
tctagatatc ggatcccgac gagctgcacc gcggtggcgg ccgtatcttt tacccatacg     120
atgttcctga ctatgcgggc tatccctatg acgtcccgga ctatgcagga tcctatccat     180
atgacgttcc agattacgct gctcagtgcg ccgcctgag agtgcaccat accacagctt      240
ttcaattcaa ttcatcattt tttttttatt cttttttttg atttcggttt ctttgaaatt     300
tttttgattc ggtaatctcc gaacagaagg aagaacgaag gaaggagcac agacttagat     360
tggtatatat acgcatatgt agtgttgaag aaacatgaaa ttgcccagta ttcttaaccc     420
aactgcacag aacaaaaacc tgcaggaaac gaagataaat catgtcgaaa gctacatata     480
aggaacgtgc tgctactcat cctagtcctg ttgctgccaa gctatttaat atcatgcacg     540
aaaagcaaac aaacttgtgt gcttcattgg atgttcgtac caccaaggaa ttactggagt     600
tagttgaagc attaggtccc aaaatttgtt tactaaaaac acatgtggat atcttgactg     660
atttttccat ggagggcaca gttaagccgc taaaggcatt atccgccaag tacaatttt      720 tactcttcga agacagaaaa tttgctgaca ttggtaatac agtcaaattg cagtactctg     780
cgggtgtata cagaatagca gaatgggcag acattacgaa tgcacacggt gtggtgggcc     840
caggtattgt tagcggtttg aagcaggcgg cagaagaagt aacaaaggaa cctagaggcc     900
ttttgatgtt agcagaattg tcatgcaagg ctccctatc tactggagaa tatactaagg     960
gtactgttga cattgcgaag agcgacaaag attttgttat cggctttatt gctcaaagag    1020
acatgggtgg aagagatgaa ggttacgatt ggttgattat gacacccggt gtgggtttag    1080
atgacaaggg agacgcattg ggtcaacagt atagaaccgt ggatgatgtg gtctctacag    1140
gatctgacat tattattgtt ggaagaggac tatttgcaaa gggaagggat gctaaggtag    1200
agggtgaacg ttacagaaaa gcaggctggg aagcatattt gagaagatgc ggccagcaaa    1260
actaaaaaac tgtattataa gtaaatgcat gtatactaaa ctcacaaatt agagcttcaa    1320
tttaattata tcagttatta ccctatgcgg tgtgaaatac cgcacagatg cgtaaggaga    1380
aaataccgca tcaggaaatt gtagcggccg cgaatttgag cttatctttt acccatacga    1440
tgttcctgac tatgcgggct atccctatga cgtcccggac tatgcaggat cctatccata    1500
tgacgttcca gattacgcta ctagcggggg gcccggtgac gggcccgtcg actgcagagg    1560
cctgcatgca agcttggcgt aatcatggtc atagctgttt cctgtgtgaa attgttatcc    1620
gctcacaatt ccacacaaca tacgagccgg aagcataaag tgtaaagcct ggggtgccta    1680
atgagtgagc taactcacat taattgcgtt gcgctcactg cccgctttcc agtcgggaaa    1740
cctatttaaa ctgtgaggac cttaatacat tcagacactt ctgcggtatc accctactta    1800
ttcccttcga gattatatct aggaacccat caggttggtg aagattacc cgttctaaga    1860
```

```
cttttcagct tcctctattg atgttacacc tggacacccc ttttctggca tccagttttt    1920
aatcttcagt ggcatgtgag attctccgaa attaattaaa gcaatcacac aattctctcg    1980
gataccacct cggttgaaac tgacaggtgg tttgttacgc atgctaatgc aaaggagcct    2040
atataccttt ggctcggctg ctgtaacagg aatataaag gcagcataa tttaggagtt     2100 tagtgaactt gcaacattta ctattttccc ttcttacgta aatattttc tttttaattc     2160 taaatcaatc ttttcaatt ttttgtttgt attcttttct tgcttaaatc tataactaca     2220
aaaaacacat acataaacta aaa                                            2243
```

<210> SEQ ID NO 142
<211> LENGTH: 70
<212> TYPE: DNA
<213> ORGANISM: Artificial Sequence
<220> FEATURE:
<223> OTHER INFORMATION: primer

<400> SEQUENCE: 142

```
tagttttgca cccgtgtaca taagcgtgaa atcaccacaa actgtgtgta ccagtcacga    60
cgttgtaaaa                                                           70
```

<210> SEQ ID NO 143
<211> LENGTH: 70
<212> TYPE: DNA
<213> ORGANISM: Artificial Sequence
<220> FEATURE:
<223> OTHER INFORMATION: primer

<400> SEQUENCE: 143

```
aagacagata tgacggtatt tttttcgaat ttgacggggc cttcactcat ttttagttta    60
tgtatgtgtt                                                           70
```

<210> SEQ ID NO 144
<211> LENGTH: 20
<212> TYPE: DNA
<213> ORGANISM: Artificial Sequence
<220> FEATURE:
<223> OTHER INFORMATION: primer

<400> SEQUENCE: 144

```
cctaccactc ggactacatc                                                20
```

<210> SEQ ID NO 145
<211> LENGTH: 20
<212> TYPE: DNA
<213> ORGANISM: Artificial Sequence
<220> FEATURE:
<223> OTHER INFORMATION: primer

<400> SEQUENCE: 145

```
caaataaggc gggaaaagtc                                                20
```

<210> SEQ ID NO 146
<211> LENGTH: 46
<212> TYPE: DNA
<213> ORGANISM: Artificial Sequence
<220> FEATURE:
<223> OTHER INFORMATION: primer

<400> SEQUENCE: 146

```
gtaccgggcc cccctcgaa aaacgatgcc acactcatat gactac                   46
```

```
<210> SEQ ID NO 147
<211> LENGTH: 43
<212> TYPE: DNA
<213> ORGANISM: Artificial Sequence
<220> FEATURE:
<223> OTHER INFORMATION: primer

<400> SEQUENCE: 147
accgcggtgg cggccgctct agttaaaaca gtctattgag tcc                43

<210> SEQ ID NO 148
<211> LENGTH: 44
<212> TYPE: DNA
<213> ORGANISM: Artificial Sequence
<220> FEATURE:
<223> OTHER INFORMATION: primer

<400> SEQUENCE: 148
gtaccgggcc ccccctcgaa aaacgatgac taaaatcttc gctt               44

<210> SEQ ID NO 149
<211> LENGTH: 42
<212> TYPE: DNA
<213> ORGANISM: Artificial Sequence
<220> FEATURE:
<223> OTHER INFORMATION: primer

<400> SEQUENCE: 149
accgcggtgg cggccgctct agttaaccga ccttaactgg ag                 42
```

GENETICALLY ENGINEERED YEAST CELL HAVING INCREASED NADPH PRODUCTION, METHOD OF INCREASING NADPH LEVEL IN YEAST CELL, METHOD OF PREPARING YEAST CELL, AND METHOD OF PRODUCING LACTATE USING YEAST CELL

CROSS-REFERENCE TO RELATED APPLICATION

This application claims the benefit of Korean Patent Application No. 10-2015-0069117, filed on May 18, 2015, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 204,791 Byte ASCII (Text) file named "722484_ST25.TXT-Revised" created on Apr. 1, 2016.

BACKGROUND

1. Field

The present disclosure relates to a genetically engineered yeast cell having increased NADPH production, a method of increasing a NADPH level in a yeast cell, a method of preparing the yeast cell, and a method of producing lactate using the yeast cell.

2. Description of the Related Art

Lactate is an organic acid widely used in a variety of industrial fields, including food, pharmaceutical, chemical, and electronic industries. Lactate is a colorless, odorless, water-soluble, low-volatile material. Lactate is also not toxic to the human body and is used as a flavoring agent, a sour taste agent, a preserving agent, or the like. Additionally, lactate is used as a source of polylactic acid (PLA) that is an environmentally friendly, biodegradable plastic known as an alternate polymeric material. Technically, PLA is a polyester-based resin obtained by ring-opening polymerization of a dimer lactide for polymerization. PLA may be variously processed into a film, a sheet, a fiber, an injection, etc. Thus, demands for PLA as a bioplastic have recently increased to broadly replace existing general petrochemical plastics, such as polyethylene (PE), polypropylene (PP), polyethylene terephthalate (PET), or polystyrene (PS). In addition, lactate includes both a hydroxyl group and a carboxyl group and thus is highly reactive. Accordingly, lactate is easily converted into an industrially important compound, such as lactate ester, acetaldehyde, or propyleneglycol and thus has received attention as an alternative chemical material of the next generation for use in the chemical industry.

Currently, lactate is produced by an industrially petrochemical synthesis process and a biotechnological fermentation process. The petrochemical synthesis process is performed by oxidizing ethylene derived from crude oil, preparing lactonitrile through addition of hydrogen cyanide after acetaldehyde, purifying by distillation, and hydrolyzing using hydrochloric acid or sulfuric acid. The biotechnological fermentation process is used to manufacture lactate from a reproducible carbon hydrate, such as starch, sucrose, maltose, glucose, fructose, or xylose, as a substrate. Therefore, a strain capable of efficiently producing lactate and a method of producing lactate using the strain are needed. To meet these needs, a method of producing lactate using a microorganism has been developed. However, homeostasis of microorganisms is an obstacle to mass-production of a single material. The present inventors have studied this problem, thereby completing the present invention.

SUMMARY

An aspect provides a yeast cell that is genetically engineered to have increased NADPH production.

Another aspect provides a method of increasing a NADPH level in a yeast cell.

Still another aspect provides a method of preparing the yeast cell that is genetically engineered to have increased NADPH production.

Still another aspect provides a method of producing lactate using the genetically engineered yeast cell.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
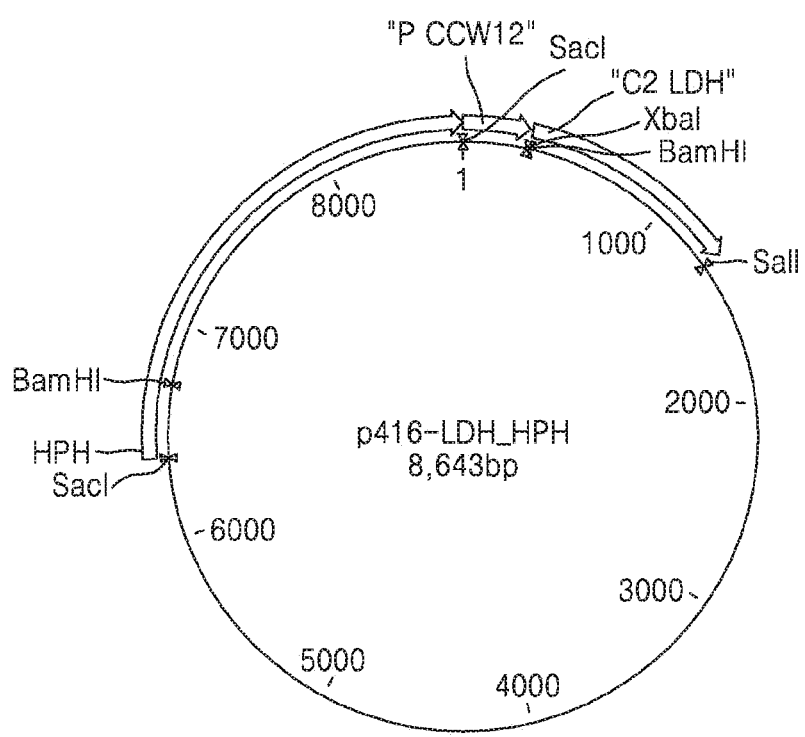
FIG. 1 is a cleavage map of a p416-ldh-HPH vector.

The term "increase in activity" or "increased activity", as used herein, may refer to a detectable increase in an activity of a cell, a protein, or an enzyme. The "increase in activity" or "increased activity" may also refer to an activity level of a modified (e.g., genetically engineered) cell, protein, or enzyme that is higher than that of a comparative cell, protein, or enzyme of the same type, such as a cell, protein, or enzyme that does not have a given genetic modification (e.g., original or "wild-type" cell, protein, or enzyme). "Cell activity" may refer to an activity of a particular protein or enzyme of a cell. For example, an activity of a modified or engineered cell, protein, or enzyme may be increased by about 5% or more, about 10% or more, about 15% or more, about 20% or more, about 30% or more, about 50% or more, about 60% or more, about 70% or more, or about 100% or more than an activity of a non-engineered cell, protein, or enzyme of the same type, i.e., a wild-type cell, protein, or enzyme. An activity of a particular protein or enzyme in a cell may be increased by about 5% or more, about 10% or more, about 15% or more, about 20% or more, about 30% or more, about 50% or more, about 60% or more, about 70% or more, or about 100% or more than an activity of the same protein or enzyme in a parent cell, e.g., a non-engineered cell or cell not having a particular genetic modification. A cell having an increased activity of a protein or an enzyme may be identified by using any method known in the art. The cell having the increased activity may have one or more genetic modifications for increasing the activity of the enzyme or polypeptide, compared to a cell lacking the one or more genetic modifications.

The term "genetic modification", as used herein, may refer to introduction of a polynucleotide encoding a polypeptide (e.g., an increase in a copy number of the gene), or substitution, addition, insertion, or deletion of one or nucleotides in a genetic material of a parent cell, or chemical mutation of a genetic material of a parent cell. The genetic modification may include such a change to a coding region of a polynucleotide that is heterologous, homologous, or both heterologous and homologous to a referenced species, or a functional fragment thereof. The genetic modification may also include modifications in non-coding regulatory regions that are capable of modifying expression of a gene or an operon, in which the non-coding regulatory regions include a 5'-non coding sequence and/or a 3'-non coding sequence."

The "increase in the copy number" may be caused by introduction or amplification of a gene, and may be achieved by genetically engineering a cell so that the cell is allowed to have a gene that does not exist in a non-engineered cell, or an increased number of copies of a gene as compared to a non-engineered cell. The introduction of the gene may be mediated by a vehicle such as a vector. The introduction may be a transient introduction in which the gene is not integrated into a genome, or an integration of the gene into the genome. The introduction may be performed, for example, by introducing a vector into the cell, in which the vector includes a polynucleotide encoding a target polypeptide, and then, replicating the vector in the cell, or by integrating the polynucleotide into the genome.

The term "gene" refers to a nucleic acid fragment capable of producing an expression product, for example, mRNA or protein, by any one of transcription and translation, and may include a coding region as well as regulatory sequences such as a 5'-non coding sequence or a 3'-non coding sequence.

The term "cell", "strain", or "microorganism" may be used interchangeably and may include a yeast, a bacterium, or a fungus.

The term "decrease in activity" or "decreased activity", as used herein, means that a cell has an activity of an enzyme or a polypeptide that is lower than the activity level in a parent cell without a particular genetic modification (e.g., a non-genetically engineered cell). Also, the "decrease in activity" or "decreased activity" means that an isolated enzyme or a polypeptide has an activity lower than that of an original or a wild-type enzyme or polypeptide. The decrease in activity or decreased activity encompasses no activity. For example, a modified (e.g., genetically engineered) cell or enzyme may have enzymatic activity of converting a substrate to a product that is decreased by about 20% or more, about 30% or more, about 40% or more, about 50% or more, about 55% or more, about 60% or more, about 70% or more, about 75% or more, about 80% or more, about 85% or more, about 90% or more, about 95% or more, or about 100%, as compared to that of a cell or enzyme that does not have the modification, i.e., a parent cell or a "wild-type" cell or enzyme. Decreased activity of an enzyme or a cell may be confirmed by any methods known in the art. The decrease in activity includes the case that an enzyme has no activity or decreased activity even though the enzyme is expressed, or the case that an enzyme-encoding gene is not expressed or expressed at a low level, compared to a cell having a non-modified gene, i.e., a parent cell or a wild-type cell.

The term "parent cell" refers to an original cell, for example, a non-genetically engineered cell of the same type as an engineered yeast cell. With respect to a particular genetic modification, the "parent cell" may be a cell that lacks the particular genetic modification, but is identical in all other respects. Thus, the parent cell may be a cell that is used as a starting material to produce a genetically engineered yeast cell having increased or decreased activity of a given protein, or increased or decreased production of a given product.

The term "parent cell" or "parent strain" may be used for a subject genetic modification. Since the parent cell may be identical to a subject cell, except the genetic modification, it may be a reference cell with respect to the genetic modification. The "genetic modification" means an artificial alteration in a constitution or structure of a genetic material of a cell. The parent cell may be a cell that does not have the corresponding genetic modification, for example, genetic modification of increasing the activity. The parent cell may be a parent yeast cell.

The term "wild-type" polypeptide or polynucleotide may be a polypeptide or polynucleotide having no particular genetic modification, and the genetic modification is to obtain a genetically engineered polypeptide or polynucleotide.

The term "disruption", as used herein, refers to a genetic modification to reduce expression of a referenced gene. The disruption includes a genetic manipulation whereby the referenced gene is not expressed (hereinafter, referred to as "inactivation" of a gene) or a genetic manipulation whereby the gene is expressed at a reduced level (hereinafter, referred to as "attenuation" of a gene). Disruption also encompasses inactivation by which no expression of a gene product occurs, or expression of only a non-functional product occurs. Disruption also encompasses attenuation by which the expression level of a functional product of a gene is reduced, but not necessarily eliminated. That is, the attenuation includes a reduction in the expression level of the functional product even though the entire expression of the gene might not be reduced, or might even be increased. Herein, the functional product of a gene refers to a product retaining a biochemical or physiological function (e.g., enzymatic activity) of the product (e.g., enzyme) of the gene of a parent cell or a wild-type cell. Thus, disruption includes functional disruption of the gene.

The disruption of a gene may be achieved by any suitable genetic manipulation such as homologous recombination, directed mutagenesis, or molecular evolution. If a cell includes a plurality of the same genes, or two or more different paralogs of a gene, one or more of the genes may be disrupted. For example, the genetic modification may be performed by transforming the cell with a vector containing a partial sequence of the gene, culturing the cell so that the gene is disrupted by homogonous recombination of the sequence with an endogenous gene of the cell, and then selecting cells, in which the homologous recombination occurred, using a selection marker.

The term "sequence identity" of a polypeptide or a polynucleotide, as used herein, refers to a degree of identity between amino acid residues or bases of sequences obtained after the sequences are aligned so as to best match in certain comparable regions. The sequence identity is a value that is measured by comparing two sequences in certain comparable regions via optimal alignment of the two sequences, in which portions of the sequences in the certain comparable regions may be added or deleted compared to reference sequences. A percentage of sequence identity may be calculated by, for example, comparing two optimally aligned sequences in the entire comparable regions, determining the number of locations in which the same amino acids or nucleic acids appear to obtain the number of matching locations, dividing the number of matching locations by the total number of locations in the comparable regions (that is, the size of a range), and multiplying a result of the division by 100 to obtain the percentage of the sequence identity. The percentage of the sequence identity may be determined using a known sequence comparison program, for example, BLASTN or BLASTP (NCBI), CLC Main Workbench (CLC bio) and MegAlign™ (DNASTAR Inc).

Various levels of sequence identity may be used to identify various types of polypeptides or polynucleotides having the same or similar functions or activities. For example, the sequence identity may include a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100%.

As used herein, the term "exogenous" means that a referenced molecule or a referenced activity is artificially introduced into a host cell. A molecule may be introduced, for example, by introducing a coding nucleic acid into a genetic material of the host, such as integration into a host chromosome, or as a non-chromosomal genetic material such as a plasmid. The term "exogenous", when used in reference to expression of a coding nucleic acid, refers to introduction of the coding nucleic acid in an expressible form into an individual. The term "exogenous", when used in reference to biosynthetic activity, refers to activity that is introduced into a host parent cell. The source may be, for example, a homologous or heterologous coding nucleic acid that expresses the referenced activity following introduction into the host parent cell. Therefore, the term "endogenous" refers to a referenced molecule or activity that is present in the host cell before genetic manipulation. Similarly, the term "endogenous", when used in reference to expression of a coding nucleic acid, refers to expression of a coding nucleic acid contained within an individual before genetic manipulation. The term "heterologous" refers to a molecule or activity derived from a source other than the referenced species, whereas "homologous" refers to a molecule or activity derived from the referenced species (e.g., the species of the host cell itself). Accordingly, exogenous expression of a coding nucleic acid may utilize either or both of heterologous and homologous coding nucleic acids.

The term "genetic engineering" or "genetically engineered", as used herein, refers to action of introducing one or more genetic modifications into a cell or a cell produced thereby.

The term "lactate", as used herein, includes "lactic acid" itself as well as a negative ion, a salt, solvate, or polymorph thereof, or a combination thereof. The salt may be, for example, an inorganic acid salt, an organic acid salt, or a metal salt. The inorganic acid salt may be hydrochloride, bromate, phosphate, sulfate or disulfate. The organic acid salt may be formate, acetate, propionate, lactate, oxalate, tartrate, malate, maleate, citrate, fumarate, besylate, camsylate, edisilate, trifluoroacetate, benzoate, gluconate, methanesulfonate, glycolate, succinate, 4-toluenesulfonate, galacturonate, embonate, glutamate or aspartate. The metal salt may be a calcium salt, a sodium salt, a magnesium salt, a strontium salt or a potassium salt.

An aspect provides a genetically engineered yeast cell having increased production of nicotinamide adenine dinucleotide phosphate, compared to a parent cell. The yeast cell may have increased lactate production compared to a parent cell.

Nicotinamide adenine dinucleotide phosphate (NADPH) is a cofactor involved in biosynthesis, for example, assimilation in a yeast cell. The genetically engineered yeast cell may have increased NADPH production in the yeast cell, compared to its parent cell.

The yeast cell may have a genetic modification that increases activity of ADE3, SHM2, MTD1, UTR1, YEF1, POS5, sPOS5, ZWF1, or a combination thereof, and/or may include exogenous gdp1, exogenous SthA, exogenous LDH mutant, or a combination thereof.

The yeast cell may be a genetically engineered yeast cell that has increased activity of ADE3, SHM2, MTD1, or a combination thereof, compared to its parent cell. The genetically engineered yeast cell is able to produce lactate. The yeast cell may include a gene encoding lactate dehydrogenase.

The ADE3 protein may be C-1-tetrahydrofolate synthase (C1-THF synthase). The ADE3 protein may be involved in 1-carbon metabolism. The metabolism may be involved in tetrahydrofolate interconversion. The ADE3 protein may be classified as EC 1.5.1.5, EC 3.5.4.9, or EC 6.3.4.3. The ADE3 protein may catalyze a reaction of 5,10-methylenetetrahydrofolate+$NADP^+$ ↔ 5,10-methenyltetrahydrofolate+NADPH. The ADE3 protein may also catalyze a reaction of 5,10-methenyltetrahydrofolate+$H_2O$ ↔ 10-formyltetrahydrofolate. The ADE3 protein may also catalyze a reaction of 10-formyltetrahydrofolate+ADP+phosphate ↔ tetrahydrofolate+ATP+formate. The ADE3 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 1. The ADE3 protein may have, for example, an NCBI reference sequence of NP_011720.3. A gene encoding the ADE3 protein may be a gene having a sequence identity of about 95% or higher with a polynucleotide sequence of SEQ ID NO: 2. The ade3 gene may have, for example, an NCBI reference sequence of NM_001181333.3.

The SHM2 protein may be serine hydroxymethyltransferase (SHMT). The SHM2 protein may be involved in one-carbon metabolism. The metabolism may be involved in tetrahydrofolate interconversion. The SHM2 protein may be glycine hydroxymethyltransferase or serine methylase. The SHM2 protein may be classified as EC 2.1.2.1. The SHM2 protein may catalyze a reaction of 5,10-methylenetetrahydrofolate+glycine+$H_2O$ ↔ tetrahydrofolate+L-serine. The SHM2 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 3. The SHM2 protein may have, for example, an NCBI reference sequence of NP_013159.1. A gene encoding the SHM2 protein may be a gene having a sequence identity of about 95% or higher with a polynucleotide sequence of SEQ ID NO: 4. The shm2 gene may have, for example, an NCBI reference sequence of NM_001181945.1.

The MTD1 protein may be methylenetetrahydrofolate dehydrogenase. The MTD1 protein may be an enzyme classified as EC 1.5.1.15. The MTD1 protein may catalyze a reaction of 5,10-methylenetetrahydrofolate+NAD+ ↔ 5,10-methenyltetrahydrofolate+NADH. The MTD1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 5. The MTD1 protein may have, for example, an NCBI reference sequence of NP_013006.3. A gene encoding the MTD1 protein may be a gene having a sequence identity of about 95% or higher with a polynucleotide sequence of SEQ ID NO: 6. The mtd1 gene may have, for example, an NCBI reference sequence of NM_001179870.3.

The yeast cell may be a genetically engineered yeast cell that has increased activity of UTR1, YEF1, POS5, or a combination thereof, compared to its parent cell. The yeast cell may include a genetic modification of increasing activity of UTR1, YEF1, POS5, or a combination thereof. The genetically engineered yeast cell is able to produce lactate. The yeast cell may include a gene encoding lactate dehydrogenase.

The UTR1 protein may be NAD(+) kinase. The UTR1 protein may be classified as EC 2.7.1.23. The UTR1 protein may be also referred to as unknown transcript 1 protein. The UTR1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 7. The UTR1 protein may have, for example, an NCBI reference sequence of NP_012583.1. A gene encoding the UTR1 protein may be a gene having a sequence identity of about 95% or higher with a polynucleotide sequence of SEQ ID NO: 8. The utr1 gene may have, for example, an NCBI reference sequence of NM_001181707.1.

The YEF1 protein may be ATP-NADH kinase YEF1. The YEF1 may be also referred to as YEL041W. The YEF1 protein may be classified as EC 2.7.1.86. The YEF1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 9. The YEF1 protein may have, for example, an NCBI reference sequence of NP_010873.1. A gene encoding the YEF1 protein may be a gene having a sequence identity of about 95% or higher with a polynucleotide sequence of SEQ ID NO: 10. The yef1 gene may have, for example, an NCBI reference sequence of NM_001178856.1.

The POS5 protein may be mitochondrial NADH kinase POS5. The POS5 protein may be classified as EC 2.7.1.86. The POS5 protein may catalyze NADPH synthesis in mitochondria. The POS5 may catalyze a reaction of ATP+NADH ↔ ADP+NADPH in mitochondria. The POS5 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 11. The POS5 protein may have, for example, an NCBI reference sequence of NP_015136.1. A gene encoding the POS5 protein may be a gene having a sequence identity of about 95% or higher with a polynucleotide sequence of SEQ ID NO: 12. The pos5 gene may have, for example, an NCBI reference sequence of NM_001184002.1.

The sPOS5 protein may be truncated NADH kinase POS5. The sPOS5 protein may be a protein prepared by removing a mitochondrial targeting sequence from POS5. The sPOS5 protein may be modified to be expressed in the cytoplasm. The sPOS5 protein may catalyze NADPH synthesis in the cytoplasm. The sPOS5 protein may catalyze a reaction of ATP+NADH ↔ ADP+NADPH in the cytoplasm. The sPOS5 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 13. A gene encoding the sPOS5 protein may be a gene having a sequence identity of about 95% or higher with a polynucleotide sequence of SEQ ID NO: 14.

The yeast cell may be genetically modified to have increased activity of GDP1, compared to its parent cell, and may have a genetic modification of increasing activity of GDP1. The yeast cell may include a gene encoding exogenous GDP1.

The GDP1 protein may be glyceraldehyde-3-phosphate dehydrogenase (GAPDH). The GAP1 may be classified as EC 1.2.1.12. The GAP1 protein may be NADP-dependent GAPDH. The exogenous GDP1 protein may be derived from *Kluyveromyces maxianus*. The GDP1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 15. A gene encoding the GDP1 protein may be a gene having a sequence identity of about 95% or higher with a polynucleotide sequence of SEQ ID NO: 16.

The yeast cell may be genetically modified to have increased activity of ZWF1, compared to its parent cell, and may have a genetic modification of increasing activity of ZWF1.

The ZWF1 protein may be glucose-6-phosphate1-dehydrogenase (G6PDH). The ZWF1 protein may be classified as EC 1.1.1.49. The ZWF1 protein may catalyze the rate-limiting step of the oxidative pentose-phosphate pathway, and may provide a reducing power by NADPH. The ZWF1 protein may catalyze a reaction of D-glucose 6-phosphate+NADP+ ↔ 6-phospho-D-glucono-1,5-lactone+NADPH.

The ZWF1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 17. The ZWF1 protein may have, for example, an NCBI reference sequence of NP_014158.1. A gene encoding the ZWF1 protein may be a gene having a sequence identity of about 95% or higher with a polynucleotide sequence of SEQ ID NO: 18. The zwf1 gene may have, for example, an NCBI reference sequence of NM_001183079.1.

The yeast cell may include a gene encoding an exogenous SthA protein. The SthA protein may be soluble pyridine nucleotide transhydrogenase. The SthA protein may be classified as EC 1.6.1.1. The SthA protein may be also referred to as STH. The SthA protein may be NAD(P)(+) transhydrogenase [B-specific]. The SthA may catalyze a reaction of NADH+NADP+ ↔ NAD++NADPH. The exogenous SthA may be derived from *Escherichia coli* (*E. coli*). The SthA protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 19. The SthA protein may have, for example, an NCBI reference sequence of NP_418397.2. A gene encoding the SthA protein may be a gene having a sequence identity of about 95% or higher with a polynucleotide sequence of SEQ ID NO: 20. The yeast cell may produce NADPH from NADH, and/or produce NADH from NADPH. The yeast cell may include an activity of interconversion between NADH and NADPH.

The yeast cell may further have a disruption of a gene encoding a polypeptide that converts acetaldehyde to ethanol. The polypeptide may be an enzyme that catalyzes conversion of acetaldehyde to ethanol. The polypeptide may be classified as EC. 1.1.1.1. The polypeptide may be an enzyme that catalyzes conversion of acetaldehyde to ethanol using conversion of NADH to NAD$^+$. The polypeptide may be alcohol dehydrogenase (ADH), and may be ADH1, ADH2, ADH3, ADH4, ADH5, or ADH6. The polypeptide converting acetaldehyde to ethanol is the same as described above.

The yeast cell may further have a disruption of a gene encoding a polypeptide that converts dihydroxyacetone phosphate (DHAP) to glycerol-3-phosphate. The polypeptide converting dihydroxyacetone phosphate (DHAP) to glycerol-3-phosphate is the same as described above.

The yeast cell including the gene encoding the exogenous SthA protein; and a disruption of the gene encoding the polypeptide converting acetaldehyde to ethanol, a disruption of the gene encoding the polypeptide converting dihydroxyacetone phosphate (DHAP) to glycerol-3-phosphate, or a combination thereof may have an increased NADPH-producing activity, compared to its parent cell. NADH increased in the yeast cell due to inactivation of the polypeptide converting acetaldehyde to ethanol by conversion of NADH to NAD$^+$, the polypeptide converting dihydroxyacetone phosphate (DHAP) to glycerol-3-phosphate, or a combination thereof is involved in the conversion of NADH+ NADP$^+$ to NAD$^+$+NADPH in a reaction which is catalyzed by the SthA protein, whereby the yeast cell has the increased NADPH-producing activity.

The yeast cell may include a mutant of lactate dehydrogenase of *Lactobacillus delbrueckii*. The mutant may be a mutant of LDH derived from *Lactobacillus delbrueckii* subsp. *Bulgaricus*(Lb). The mutant may be D176A of LDH derived from wild-type *Lactobacillus delbrueckii* subsp. *Bulgaricus*(Lb). The mutant may have an amino acid sequence of SEQ ID NO: 21. A gene encoding the mutant may have a polynucleotide sequence of SEQ ID NO: 22.

The yeast cell including the mutant may further have an increased activity of ZWF1 protein, and may further include a genetic modification of increasing activity of the ZWF1 protein.

The yeast cell may have a modification of an expression regulatory sequence of the gene encoding an above-referenced expression product. The expression regulatory sequence of the gene may be a promoter or terminator for expression of the gene. The expression regulatory sequence may be a sequence encoding a motif which may influence the expression of the gene. The motif may be, for example, a secondary structure-stabilizing motif, an RNA destabilizing motif, a splice-activating motif, a polyadenylation motif, an adenine-rich sequence, or an endonuclease recognition site.

The promoter may be an exogenous promoter that is operably linked to the gene encoding the expression product. The promoter may be a constitutive promoter. The promoter may be about 50%, 60%, 70%, 80%, 90%, 95%, or 95% or higher homologous to a promoter that is native to a yeast gene. The promoter may be about 50%, 60%, 70%, 80%, 90%, 95%, or 95% or higher homologous to a promoter for a gene that is native to the host cell. The promoter may be a promoter that is about 80%, 85%, 90% or 95% homologous to covalently linked Cell Wall protein 12 (CCW12), pyruvate decarboxylase (PDC) such as PDC1, phosphoglycerate kinase (PGK) such as PGK1, transcription elongation factor (TEF) such as TEF-1 and TEF-2, glyceraldehyde-3-phosphate dehydrogenase such as TDH1, TDH2, TDH3, or GPD1, triose phosphate isomerase (TPI1), purine-cytosine permease (PCPL3), alcohol dehydrogenase (ADH1), L-(+)-lactate-cytochrome c oxidoreductase(CYB) such as CYB2, xylose reductase (XR), xylitol dehydrogenase (XDH), CYC (cytochrome c), ADH, Histone H3 (e.g., HHT1 or HHT2) promoter, and a promoter derived from the gene selected from the group consisting of combinations thereof. The promoters of CYC (cytochrome c), TEF (transcription elongation factor), GPD, ADH, CCW12, HHT2, TPI, and PGK genes may have a nucleotide sequence of SEQ ID NOS: 53, 54, 55, 56, 57, 58, 59, and 134, respectively.

The terminator may be about 50%, 60%, 70%, 80%, 90%, 95%, or 95% or higher homologous to a terminator that is native to a yeast gene. The terminator may be at least about 50%, 60%, 70%, 80%, 90%, 95%, or 95% or higher homologous to a terminator for a gene that is native to the host cell. The terminator may be selected from the group consisting of terminators of PGK1 (phosphoglycerate kinase 1), CYC1 (cytochrome c 1), GAL1 (galactokinase 1), and TPS1 (trehalose-6-phosphate synthase 1) genes. The CYC1 terminator may have a nucleotide sequence of SEQ ID NO: 60. The vector may further include a selection marker.

Further, the yeast cell may have an increase in the copy number of the gene encoding the expression product. The yeast cell may include an exogenous gene encoding the expression product. The exogenous gene may be properly regulated by an exogenous promoter operably linked to the gene. The promoter is the same as described above.

The yeast cell may belong to the genus *Saccharomyces*, *Kluyveromyces*, *Candida*, *Pichia*, *Issatchenkia*, *Debaryomyces*, *Zygosaccharomyces*, *Shizosaccharomyces*, or *Saccharomycopsis*. The genus *Saccharomyces* may be, for example, *Saccharomyces cerevisiae* (*S. cerevisiae*), *Saccharomyces bayanus* (*S. bayanus*), *Saccharomyces boulardii* (*S. boulardii*), *Saccharomyces bulderi* (*S. bulderi*), *Saccharomyces cariocanus* (*S. cariocanus*), *Saccharomyces cariocus* (*S. cariocus*), *Saccharomyces chevalieri* (*S. chevalieri*), *Saccharomyces dairenensis* (*S. dairenensis*), *Saccharomyces ellipsoideus* (*S. ellipsoideus*), *Saccharomyces eubayanus* (*S. eubayanus*), *Saccharomyces exiguus* (*S. exiguus*), *Saccharomyces florentinus* (*S. florentinus*), *Saccharomyces kluyveri* (*S. kluyveri*), *Saccharomyces martiniae* (*S. martiniae*), *Saccharomyces monacensis* (*S. monacensis*), *Saccharomyces norbensis* (*S. norbensis*), *Saccharomyces paradoxus* (*S. paradoxus*), *Saccharomyces pastorianus* (*S. pastorianus*), *Saccharomyces spencerorum* (*S. spencerorum*), *Saccharomyces turicensis* (*S. turicensis*), *Saccharomyces unisporus* (*S. unisporus*), *Saccharomyces uvarum* (*S. uvarum*), or *Saccharomyces zonatus* (*S. zonatus*).

The yeast cell may have a lactate-producing ability. The yeast cell may have an activity of a polypeptide converting pyruvate into lactate. The yeast cell may include a gene encoding the polypeptide converting pyruvate into lactate. The gene may be an exogenous gene. The yeast cell may have the increased activity of the polypeptide converting pyruvate into lactate. The polypeptide converting pyruvate into lactate may be an enzyme that catalyzes conversion of pyruvate into lactate, and may be lactate dehydrogenase (LDH). The lactate dehydrogenase may be a NAD(P)-dependent enzyme. Further, the lactate dehydrogenase may be stereo-specific.

The gene encoding the lactate dehydrogenase may be derived from a bacterium, a yeast, a fungus, a mammal, or a reptile. The gene may be a polynucleotide encoding LDH derived from one or more selected from the group consisting of the genus *Lactobacillus* such as *L. delbrueckii* subsp. *bulgaicus* and *L. bulgaricus*, *L. johnsonii*, *L. plantarum*, *Pelodiscus sinensis japonicus*, *Ornithorhynchus anatinus*, *Tursiops truncatus*, *Rattus norvegicus*, *Xenopus laevis*, and

*Bos Taurus*. The LDH is an enzyme producing D-lactate, which is classified as EC 1.1.1.28 or an enzyme producing L-lactate, which is classified as EC 1.1.1.27. The D-lactate dehydrogenase (D-LDH) may be an enzyme classified as EC 1.1.1.28. The D-LDH may be referred to as D-specific 2-hydroxyacid dehydrogenase. The D-LDH may be an enzyme that catalyzes conversion of pyruvate and NADH into (R)-lactate and NAD$^+$. The D-LDH may have a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 23. A gene encoding the D-LDH may have a sequence identity of about 60% or higher, about 70% or higher, about 80% or higher, about 90% or higher, about 95% or higher, about 96% or higher, about 97% or higher, about 98% or higher, or about 99% or higher with a polynucleotide sequence of SEQ ID NO: 24.

The L-lactate dehydrogenase (L-LDH) may be an enzyme classified as EC 1.1.1.27. The L-LDH may be referred to as L-specific 2-hydroxyacid dehydrogenase. The L-LDH may be an enzyme that catalyzes conversion of pyruvate and NADH into (S)-lactate and NAD$^+$. The L-LDH may have a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 25, 26, 27, 28, or 29. A gene encoding the L-LDH may have a sequence identity of about 60% or higher, about 70% or higher, about 80% or higher, about 90% or higher, about 95% or higher, about 96% or higher, about 97% or higher, about 98% or higher, or about 99% or higher with a polynucleotide sequence of SEQ ID NO: 30.

The gene encoding lactate dehydrogenase may be included in a vector. The vector may include a replication origin, a promoter, a polynucleotide encoding lactate dehydrogenase, and a terminator. The replication origin may include a yeast autonomous replication sequence (ARS). The yeast ARS may be stabilized by a yeast centrometric sequence (CEN). The promoter is the same as described above. The terminator is the same as described above. The polynucleotide encoding lactate dehydrogenase may be included in a particular locus of a genome of a yeast cell. When the polynucleotide encoding lactate dehydrogenase functions to produce an active protein in a cell, the polynucleotide is considered to be "functional" within the cell.

The yeast cell may include one copy of the lactate dehydrogenase-encoding polynucleotide or multiple copies of the lactate dehydrogenase-encoding polynucleotide, for example, 2 to 10 copies. The yeast cell may include, for example, 1 to 8, 1 to 7, 1 to 6, 1 to 5, 1 to 4, or 1 to 3 copies of the lactate dehydrogenase-encoding polynucleotide. If the yeast cell includes multiple lactate dehydrogenase-encoding polynucleotides, each of the polynucleotide may include copies of the same polynucleotide or copies of polynucleotides encoding two or more different lactate dehydrogenases. The multiple copies of the polynucleotide encoding exogenous lactate dehydrogenase may be included in the same locus or multiple loci in a genome of a host cell, and a promoter or terminator of each copy may be the same as or different from each other.

The yeast cell may further have a genetic modification that decreases an activity of a polypeptide converting pyruvate to acetaldehyde, a polypeptide converting dihydroxyacetone phosphate (DHAP) to glycerol-3-phosphate, a polypeptide converting acetaldehyde to ethanol, a polypeptide converting acetaldehyde to acetate or a combination thereof, compared to the parent cell.

The yeast cell may have a disruption of a gene encoding the polypeptide that converts pyruvate to acetaldehyde. The polypeptide that converts pyruvate to acetaldehyde may be an enzyme that catalyzes conversion of pyruvate to acetaldehyde and is classified as EC 4.1.1.1. The polypeptide that converts pyruvate to acetaldehyde may be, for example, pyruvate decarboxylase (PDC). PDC may be, for example, PDC1, PDC5, or PDC6. The polypeptide that converts pyruvate to acetaldehyde may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 31 or 33. The gene encoding the polypeptide that converts pyruvate to acetaldehyde may have a polynucleotide sequence encoding an amino acid sequence having a sequence identity of about 95% or higher with an amino acid sequence of SEQ ID NO: 31 or 33, or a polynucleotide sequence of SEQ ID NO: 32 or 34. The gene may be pdc1, pdc5, or pdc6.

The yeast cell may have a disruption of a gene encoding the polypeptide that converts dihydroxyacetone phosphate (DHAP) to glycerol-3-phosphate. The polypeptide may be classified as EC 1.1.1.8, EC 1.1.5.3, or EC 1.1.1.94. The polypeptide may be glycerol-3-phosphate dehydrogenase (GPD). GPD may be, for example, GPD1, GPD2, or GPD3. The yeast cell may have a disruption of a gene encoding GPD1, GPD2, GPD3, or a combination thereof. GPD1 may be cytosolic glycerol-3-phosphate dehydrogenase, and may be an enzyme that catalyzes reduction of DHAP to glycerol-3-phosphate using oxidation of NADH or NADP to NAD$^+$ or NADP$^+$. GPD2 may be glycerol-3-phosphate dehydrogenase (quinone). GPD3 may be glycerol-3-phosphate dehydrogenase (NAD(P)$^+$). GPD may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 35. A gene (gpd gene) encoding GPD may have a polynucleotide sequence encoding an amino acid sequence having a sequence identity of about 95% or higher with an amino acid sequence of SEQ ID NO: 35, or a polynucleotide sequence of SEQ ID NO: 36.

The yeast cell may have a disruption of a gene encoding the polypeptide that converts lactate to pyruvate. The polypeptide may be classified as EC. 1.1.2.4 or EC 1.1.2.3.

The polypeptide classified as EC. 1.1.2.4 may be D-lactate ferricytochrome C oxidoreductase. The D-lactate ferricytochrome C oxidoreductase may be also referred to as D-lactate dehydrogenase (DLD). The polypeptide may be DLD1, DLD2, or DLD3. The polypeptide may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 37. The gene encoding the polypeptide may have a polynucleotide sequence encoding an amino acid sequence having a sequence identity of about 95% or higher with the amino acid sequence of SEQ ID NO: 37. For example, the gene may have a polynucleotide sequence of SEQ ID NO: 38.

The polypeptide classified as EC. 1.1.2.3 may be L-lactate cytochrome-c oxidoreductase (CYB2), and also referred to as CYB2A or CYB2B. CYB2 may be a cytochrome c-dependent enzyme. CYB2 may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 39. The gene encoding the polypeptide that converts lactate to pyruvate may have a polynucleotide sequence encoding an amino acid sequence having a sequence identity of about 95% or higher with the amino acid sequence of SEQ ID NO: 39, or a polynucleotide sequence of SEQ ID NO: 40.

The yeast cell may have a disruption of a gene encoding the polypeptide that converts acetaldehyde to ethanol. The polypeptide may be an enzyme that catalyzes conversion of acetaldehyde to ethanol. The polypeptide may be classified as EC. 1.1.1.1. The polypeptide may be an enzyme that catalyzes conversion of acetaldehyde to ethanol using conversion of NADH to NAD+. The polypeptide may be alcohol dehydrogenase (ADH). ADH may be, for example, Adh1, Adh2, Adh3, Adh4, Adh5, or Adh6. The polypeptide may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 41 or 43. The gene encoding the polypeptide may have a polynucleotide sequence encoding an amino acid sequence having a sequence identity of about 95% or higher with the amino acid sequence of SEQ ID NO: 41 or 43 or a polynucleotide sequence of SEQ ID NO: 42 or 44. The gene may be, for example, adh1, adh2, adh3, adh4, adh5, or adh6.

The yeast cell may have a disruption of a gene encoding the polypeptide that converts acetaldehyde to acetate. The polypeptide may be an enzyme that catalyzes conversion of acetaldehyde to acetate. The polypeptide may be classified as EC. 1.2.1.4. The polypeptide may be activated by $Mg^{2+}$ and specific to NADP. This enzyme may be involved in production of acetate. Cytosolic acetyl-CoA may be synthesized from the produced acetate. The polypeptide may be aldehyde dehydrogenase (ALD). ALD may be, for example, ALD6. The polypeptide may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 45. The gene encoding the polypeptide may have a polynucleotide sequence encoding an amino acid sequence having a sequence identity of about 95% or higher with the amino acid sequence of SEQ ID NO: 45 or a polynucleotide sequence of SEQ ID NO: 46. The gene may be, for example, ald6.

The yeast cell may further have an increased activity of an enzyme that catalyzes conversion of acetaldehyde to acetyl-CoA, compared to the parent cell.

The enzyme that catalyzes conversion of acetaldehyde to acetyl-CoA may be acylating acetaldehyde dehydrogenase (A-ALD) that is classified as EC 1.2.1.10. One type of the enzyme that catalyzes conversion of acetaldehyde to acetyl-CoA may be a part of a bifunctional aldolase-dehydrogenase complex associated with 4-hydroxy-2-ketovalerate catabolism. The bifunctional enzyme catalyzes final two steps of a meta-cleavage pathway of catechol, which is an intermediate in various bacterial species in decomposition of phenol, toluene, naphthalene, biphenyl, and other aromatic compounds. First, 4-hydroxy-2-ketovalerate is converted to pyruvate and acetaldehyde by 4-hydroxy-2-ketovalerate aldolase, and then, acetaldehyde is converted to acetyl-CoA by A-ALD. The type of A-ALD may be, for example, DmpF of *Pseudomonas* sp. CF600 (Genbank No: CAA43226). MhpF protein of *Escherichia coli* is a homologue with respect to DmpF. Another type of the enzyme that catalyzes conversion of acetaldehyde to acetyl-CoA is a protein that catalyzes a reversible conversion between strictly or facultative anaerobic microorganism-derived acetyl-CoA and acetaldehyde, and does not have alcohol dehydrogenase activity. Examples of this type of protein may be found in *Clostridium kluyveri*. A-ALD is annotated to the genome of *Clostridium kluyveri* DSM 555 (Genbank No: EDK33116). Homologous protein AcdH was confirmed in the genome of *Lactobacillus plantarum* (Genbank No: NP_784141). Another example of this type of protein is the gene product of *Clostridium beijerinckii* NRRL B593. An example of A-ALD is *Escherichia coli*-derived MhpF or a functional homologue thereof, for example, *Escherichia coli* and *S. typhimurium*-derived EutE (for example, an EutE gene having a nucleotide sequence of SEQ ID NO: 48 and an EutE protein having an amino acid sequence of SEQ ID NO: 47), or *Pseudomonas* sp. CF600-derived dmpF. A-ALD may be $NAD(P)^+$ dependent. A-ALD may have an activity to catalyze the following reaction:

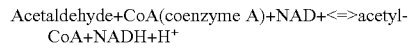

Acetaldehyde+CoA(coenzyme A)+NAD+<=>acetyl-CoA+NADH+H+

A-ALD may be an A-ALD capable of being expressed without formation of a complex with other proteins. The yeast cell might not include, for example, an exogenous enzyme classified as EC 4.1.3.39 or a gene thereof.

The yeast cell may include an exogenous gene encoding an enzyme that catalyzes conversion of acetaldehyde to acetyl-CoA. The A-ALD exogenous gene may be expressed in the yeast cell in an amount sufficient to increase an activity of the enzyme catalyzing the conversion of acetaldehyde to acetyl-CoA, compared to the parent cell. The A-ALD exogenous gene may code for an amino acid sequence that has a sequence identity of 95% or more with an amino acid sequence of SEQ ID NO: 47. The A-ALD exogenous gene may have a sequence identity of about 95% or higher with a nucleotide sequence of SEQ ID NO: 48. SEQ ID NO: 48 is a nucleotide sequence of *Escherichia coli*-derived A-ALD gene.

The yeast cell may further have an increased activity of radiation sensitivity complementing kinase (RCK), compared to the parent cell. The radiation sensitivity complementing kinase may be serine/threonine-protein kinase. The kinase may be an enzyme classified as EC 2.7.11.1. The radiation sensitivity complementing kinase may be RCK1 or RCK2. The radiation sensitivity complementing kinase may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 45 or 47. For example, RCK1 and RCK2 may have an amino acid sequence of SEQ ID NOS: 49 and 51, respectively. The radiation sensitivity complementing kinase may have a polynucleotide sequence encoding a protein having a sequence identity of about 95% or higher with SEQ ID NO: 49 or 51 or a polynucleotide sequence of SEQ ID NO: 50 or SEQ ID NO: 52. For example, rck1 and rck2 genes may have a polynucleotide sequence of SEQ ID NOS: 50 and 52, respectively.

The yeast cell may be a yeast cell that has increased activity of ADE3, SHM2, MTD1, UTR1, YEF1, POS5, sPOS5, zwf1, or a combination thereof, compared to its parent cell; a disruption of the gene encoding the polypeptide that converts pyruvate to acetaldehyde, the gene encoding the polypeptide that converts lactate to pyruvate, the gene encoding the polypeptide that converts dihydroxyacetone phosphate (DHAP) to glycerol-3-phosphate, the gene encoding the polypeptide that converts pyruvate to D-lactate, the gene encoding the polypeptide that converts acetaldehyde to ethanol, the gene encoding the polypeptide that converts acetaldehyde to acetate, or a combination thereof; the gene encoding the polypeptide that converts pyruvate to lactate, the gene encoding the polypeptide that converts acetaldehyde to acetyl-CoA, and an increased activity of radiation sensitivity complementing kinase. The yeast cell may be *Saccharomyces cerevisiae*.

The yeast cell may be a yeast cell that has the gene of exogenous gdp1, exogenous SthA, exogenous LDH mutant, or a combination thereof; a disruption of the gene encoding the polypeptide that converts pyruvate to acetaldehyde, the gene encoding the polypeptide that converts lactate to pyruvate, the gene encoding the polypeptide that converts dihydroxyacetone phosphate (DHAP) to glycerol-3-phosphate, the gene encoding the polypeptide that converts pyruvate to D-lactate, the gene encoding the polypeptide that converts acetaldehyde to ethanol, the gene encoding the polypeptide that converts acetaldehyde to acetate, or a combination thereof; the gene encoding the polypeptide that converts pyruvate to lactate, the polypeptide that converts acetaldehyde to acetyl-CoA, and an increased activity of radiation sensitivity complementing kinase. The yeast cell may be *Saccharomyces cerevisiae*.

The yeast cell may have a decreased activity of a pathway of preventing a flow of a metabolite to lactate. Further, the yeast cell may have an increased activity of a pathway of facilitating or helping a flow of a metabolite to lactate.

Another aspect provides a method of increasing a NADPH level in a yeast cell. The method may be a method of preparing a yeast cell having increased lactate production compared to a parent cell. The method may include overexpressing ade3, shm2, mtd1, utr1, yef1, POS5, sPOS5, zwf of the yeast cell, or a combination thereof. The method may include introducing the exogenous gdp1, exogenous SthA gene, or exogenous ldh mutant into the yeast cell.

Still another aspect provides a method of preparing a yeast cell producing lactate, including overexpressing ade3, shm2, mtd1, utr1, yef1, POS5, sPOS5, zwf, or a combination thereof in the yeast cell or introducing exogenous gdp1, exogenous SthA gene, exogenous ldh mutant into the yeast; and introducing the gene encoding the polypeptide that converts pyruvate to lactate. All aspects of the method, and genetic modifications used in accordance therewith to affect overexpression or introduction of genes and genetic material, are as described with respect to the genetically engineered yeast cell.

The method of preparing the yeast cell producing lactate may include overexpressing ade3, shm2, mtd1, utr1, yef1, POS5, sPOS5, zwf, or a combination thereof in the yeast cell, or introducing exogenous gdp1, exogenous SthA gene, exogenous ldh mutant into the yeast cell. In this regard, the "yeast cell", "ade3", "shm2", "mtd1", "utr1", "yef1", "POS5", "sPOS5", "zwf", "gdp1", "SthA", and "ldh mutant" are the same as described above.

The overexpression may be overexpression of a protein encoded by ade3, shm2, mtd1, utr1, yef1, POS5, sPOS5, zwf, or a combination thereof. The overexpression means that the yeast cell overexpressing a gene of ade3, shm2, mtd1, utr1, yef1, POS5, sPOS5, zwf, or a combination thereof produces a protein encoded thereby which has the enzymatic activity at a higher or much higher normal level under the same conditions than its parent cell. The overexpression also means that the yeast cell produces mRNA encoding the protein at a higher or much higher normal level under the same conditions than its parent cell. Therefore, overexpression of the protein may be determined by measuring an inactivation level of the enzyme in the host cell using a suitable enzymatic analysis. The overexpressing may be performed to cause a genetic modification of increasing the activity.

The method of preparing the yeast cell producing lactate may include introducing a gene encoding a polypeptide that converts pyruvate to lactate. In this regard, the "polypeptide that converts pyruvate to lactate" and the "gene encoding the polypeptide that converts pyruvate to lactate" are the same as described above. The introduction of the gene may be mediated by a vehicle such as a vector. The introduction may be a transient introduction in which the gene is not integrated into a genome, or an integration of the gene into the genome. The introduction may be performed, for example, by introducing a vector into the cell, in which the vector includes a polynucleotide encoding a target polypeptide, and then, replicating the vector in the cell, or by integrating the polynucleotide into the genome.

Further, the method of preparing the yeast cell producing lactate may further include disrupting the gene encoding the polypeptide that converts pyruvate to acetaldehyde, the gene encoding the polypeptide that converts dihydroxyacetone phosphate (DHAP) to glycerol-3-phosphate, the gene encoding the polypeptide that converts lactate to pyruvate, the gene encoding the polypeptide that converts acetaldehyde to ethanol, the gene encoding the polypeptide that converts acetaldehyde to acetate, or a combination thereof. In this regard, the "polypeptide that converts pyruvate to acetaldehyde", "gene encoding the polypeptide that converts pyruvate to acetaldehyde", "polypeptide that converts dihydroxyacetone phosphate (DHAP) to glycerol-3-phosphate", "gene encoding the polypeptide that converts dihydroxyacetone phosphate (DHAP) to glycerol-3-phosphate", "polypeptide that converts lactate to pyruvate", "gene encoding the polypeptide that converts lactate to pyruvate", "polypeptide that converts acetaldehyde to ethanol", "gene encoding the polypeptide that converts acetaldehyde to ethanol", "polypeptide that converts acetaldehyde to acetate", "gene encoding the polypeptide that converts acetaldehyde to acetate", and "disruption" are the same as described above.

Further, the method of preparing the yeast cell producing lactate may further include introducing the gene encoding the polypeptide that converts pyruvate to lactate, the gene encoding the polypeptide that converts acetaldehyde to acetyl-CoA, and overexpressing radiation sensitivity complementing kinase. The "polypeptide that converts pyruvate to lactate", "gene encoding the polypeptide that converts pyruvate to lactate", "polypeptide that converts acetaldehyde to acetyl-CoA" and "radiation sensitivity complementing kinase" are the same as described above.

Still another aspect provides a method of producing lactate, including culturing the yeast cell. The yeast cell is the same as described above.

The culturing may be performed in a medium containing a carbon source, for example, glucose. The medium used for culturing the yeast cell may be any general medium that is suitable for host cell growth, such as a minimal or complex medium containing proper supplements. The suitable medium may be commercially available or prepared by a known preparation method. The medium used for the culturing may be a medium that satisfies the requirements of a particular yeast cell. The medium may be a medium selected from the group consisting of a carbon source, a nitrogen source, a salt, trace elements and combinations thereof.

The culturing conditions may be properly controlled in order to obtain lactate from the genetically engineered yeast cell. For proliferation, the cell may be cultured under aerobic conditions. Thereafter, the cell may be cultured under microaerobic conditions or anaerobic conditions in order to produce lactate. The term "anaerobic conditions" means oxygen deficient conditions. The term "microaerobic conditions", when used in reference to culture or growth conditions, means that a concentration of dissolved oxygen (DO) in a medium is more than 0% and less than about 10% of saturation for DO in a liquid medium. The microaerobic conditions also include growing or resting cells in a liquid medium or on a solid agar plate inside a sealed chamber which is maintained with an atmosphere of less than 1% oxygen. The percentage of oxygen may be maintained by, for example, sparging the culture with an $N_2/CO_2$ mixture or other suitable non-oxygen gas. The oxygen conditions include maintaining the concentration of DO at 0% to 10%, for example, 0 to 8%, 0 to 6%, 0 to 4%, or 0 to 2%.

The term "culture conditions" means conditions for culturing the yeast cell. Such culture conditions may include, for example, a carbon source, a nitrogen source, or an oxygen condition utilized by the yeast cell. The carbon source that may be utilized by the yeast cell may include monosaccharides, disaccharides, or polysaccharides. The carbon source may be glucose, fructose, mannose, or galactose. The nitrogen source that may be utilized by the yeast cell may be an organic nitrogen compound or an inorganic nitrogen compound. The nitrogen source may be exemplified by amino acids, amides, amines, nitrates, or ammonium salts.

The method of producing lactate may further include recovering lactate from the culture (e.g., from the culture medium).

Recovery of lactate from the culture may be performed by isolation using a general method known in the art. Such isolation method may be centrifugation, filtration, ion chromatography, or crystallization. For example, the culture is centrifuged at a low speed to remove biomass, and a resulting supernatant is subjected to ion chromatography for isolation.

According to the yeast cell that is genetically engineered to have increased NADPH production, a NADPH level may be increased in the yeast cell.

According to the method of increasing the NADPH level in the yeast cell, the NADPH level may be increased in the yeast cell.

According to the method of preparing the yeast cell that is genetically engineered to have increased NADPH production, the NADPH level may be increased in the yeast cell.

According to the method of producing lactate, lactate may be efficiently produced.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to the exemplary embodiments. However, the exemplary embodiments described herein should be considered in a descriptive sense only and not for purposes of limitation.

EXAMPLE 1

Preparation of D-Lactate-Producing Strain

To prepare Saccharomyces cerevisiae CEN.PK2-1D wild-type strain (MATαura3-52; trp1-289; leu2-3,112; his3Δ1; MAL2-8C; SUC2, EUROSCARF accession number: 30000B) as a lactate-producing strain, a lactate-producing strain having the following genetic modification is prepared.

1. Preparation of S. cerevisiae CEN.PK2-1D(Δ pdc1::ldh)

1.1. Preparation of Vector for pdc1 Deletion and ldh Introduction

To block a pathway of converting pyruvate to ethanol via acetaldehyde in Saccharomyces cerevisiae CEN.PK2-1 D, a pyruvate decarboxylase 1 (pyruvate decarboxylase1: pdc1)-encoding gene is deleted. To delete the pdc1 gene and express LbLdh at the same time, the pdc1 gene is replaced with 'ldh cassette' so as to delete the pdc1 gene. Unless otherwise specified, the "cassette" refers to a unit sequence capable of expressing a protein, in which a promoter, a coding sequence, and a terminator are operably linked to the unit sequence.

In detail, to prepare an 'ldh cassette'-containing vector, a CCW12 promoter sequence (SEQ ID NO: 57) which is obtained by PCR using genomic DNA of Saccharomyces cerevisiae as a template and a primer set of SEQ ID NOS: 61 and 62 as primers, and 'ldh gene (SEQ ID NO: 30)' are digested with SacI/XbaI and BamHI/SalI, respectively and ligated to a pRS416 vector (ATCC87521™) which is digested with the same enzymes. The pRS416 vector is a yeast centromere shuttle plasmid having a T7 promoter, an ampicillin resistance in bacteria and a URA3 cassette in yeast as a selection marker, and restriction enzyme cloning sites.

Figure 2:
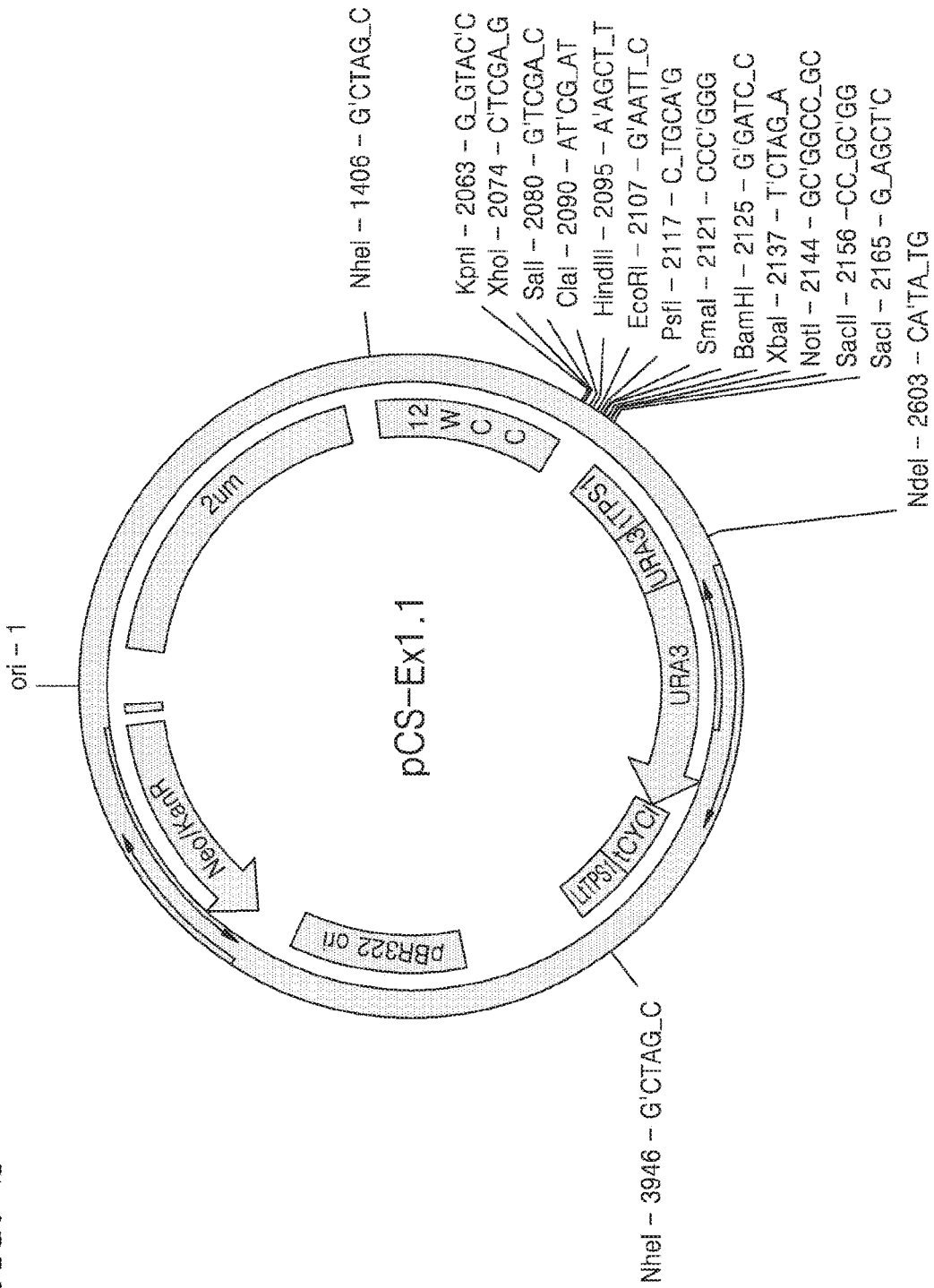
FIG. 2 illustrates a pCS-Ex1.1 vector.

Next, PCR is performed using a pCEP4 plasmid (Invitrogen, Cat. no. V044-50) as a template and a primer set of SEQ ID NOS: 63 and 64 as primers to amplify an "HPH cassette" sequence (SEQ ID NO: 65). The amplified "HPH cassette" and the pRS416 vector are digested with SacI enzyme, respectively and ligated to each other so as to prepare a p416-ldh-HPH vector containing a structure of operably linking the 'ldh cassette' and the "HPH cassette". FIG. 2 shows a cleavage map of the p416-ldh-HPH vector. In FIG. 2, "P CCW12" and "C2 LDH" indicate the CCW12 promoter and LDH orf, respectively. The pCEP4 plasmid is an episomal mammalian expression vector that uses the cytomegalovirus (CMV) immediate early enhancer/promoter for high level transcription of recombinant genes inserted into the multiple cloning site. pCEP4 has a hygromycin B resistance gene for stable selection in transfected cells. Here, the 'ldh cassette' represents a region that allows the ldh gene to be expressed, because it contains the ldh gene and its regulatory region. Transcription of the ldh gene is allowed in the presence of the CCW12 promoter. Further, the 'HPH (hygromycin B phosphotransferase) cassette' represents a region that allows the hygromycin B resistance gene to be expressed, because it contains the hygromycin B resistance gene and its regulatory region.

A pdc1 deletion vector is prepared by PCR using p416-ldh-HPH as a template and a primer set of SEQ ID NOS: 66 and 67 as primers. ldh gene fragment and pUC57-Ura3HA vector (DNA2.0 Inc.; SEQ ID NO: 68) are digested with SacI, respectively and ligated to each other so as to prepare pUC-uraHA-ldh. From this vector, a pdc1 deletion cassette is amplified by PCR using a primer set of SEQ ID NOS: 69 and 70 having a homologous sequence with the pdc1 gene.

1.2. S. Preparation of cerevisiae CEN.PK2-1D(Δ pdc1::ldh)

The pdc1 deletion cassette prepared in 1.1 is introduced into *Saccharomyces cerevisiae* (CEN.PK2-1D, EUROSCARF accession number: 30000B). Introduction of the pdc1 deletion cassette is performed by general heat shock transformation. After transformation, cells are cultured in a uracil dropout medium to replace pdc1 ORF on the chromosome with the cassette.

To examine the pdc1 deletion in the resulting cells, PCR is performed using the genome of the cell as a template and a primer set of SEQ ID NOS: 71 and 72 to confirm pdc1 gene deletion and ldh gene introduction. As a result, *S. cerevisiae* CEN.PK2-1D(Δ pdc1::$P_{ccw12}$-Lbldh) is identified.

2. Preparation of *S. cerevisiae* CEN.PK2-1D(Δ pdc1::ldh, Δ gpd1::ldh)

2.1. Preparation of Vector for gpd1 Deletion

To block a pathway of converting dihydroxyacetone phosphate (DHAP) to glycerol-3-phosphate in *S. cerevisiae* CEN.PK2-1D(Δ pdc1::ldh) prepared in 1 of Example 2, a glycerol-3-phosphate dehydrogenase(gpd1)-encoding gene is deleted.

In detail, PCR is performed using pUC-uraHA-ldh prepared in 1.1 of Example 2 as a template and gpd1 homologous recombination sequences of SEQ ID NOS: 73 and 74 as primers so as to prepare a gpd1 deletion cassette.

2.2. Preparation of *S. cerevisiae* CEN.PK2-1D(Δ pdc1::ldh, Δ gpd1::ldh)

The gpd1 deletion cassette prepared in 2.1 is introduced into *S. cerevisiae* CEN.PK2-1D(Δ pdc1::ldh) prepared in 1 of Example 2. Introduction is performed by general heat shock transformation. After transformation, cells are cultured in a uracil dropout medium to replace gdp1 ORF on the chromosome with the cassette.

To examine the gpd1 deletion in the resulting cells, PCR is performed using the genome of the cell as a template and a primer set of SEQ ID NOS: 75 and 76 to confirm gpd1 gene deletion. As a result, *S. cerevisiae* CEN.PK2-1D(Δ pdc1::ldh, Δ gpd1::ldh) is identified.

3. Preparation of *S. cerevisiae* CEN.PK2-1D(Δ pdc1::ldh, Δ gpd1::ldh, Δ dld1::ldh)

3.1. Preparation of Vector for dld1 Deletion

To block a pathway of converting d-lactate to pyruvate in *S. cerevisiae* CEN.PK2-1D(Δ pdc1::ldh, Δ gpd1:ldh) prepared in 2 of Example 2, a dld1 gene is deleted.

In detail, PCR is performed using pUC-uraHA-ldh prepared in 1.1 of Example 2 as a template and dld1 homologous recombination sequences of SEQ ID NOS: 77 and 78 as primers so as to prepare a dld1 deletion cassette.

3.2. Preparation of *S. cerevisiae* CEN.PK2-1D(Δ pdc1::ldh, Δ gpd1::ldh, Δ dld1::ldh)

The dld1 deletion cassette prepared in 3.1 is introduced into *S. cerevisiae* CEN.PK2-1D(Δ pdc1::ldh, Δ gpd1:ldh). Introduction is performed by general heat shock transformation. After transformation, cells are cultured in a uracil dropout medium to replace dld1 ORF on the chromosome with the cassette.

To examine the dld1 deletion in the resulting cells, PCR is performed using the genome of the cell as a template and a primer set of SEQ ID NOS: 79 and 80 to confirm dld1 gene deletion. As a result, *S. cerevisiae* CEN.PK2-1D(Δ pdc1::ldh, Δ gpd1:ldh, Δ dld1:ldh) is identified.

4. Preparation of *S. cerevisiae* CEN.PK2-1D(Δ pdc1::ldh, Δ gpd1::ldh, Δ dld1::ldh, Δ pdc6::ldh)

4.1. Preparation of pdc6 Gene Deletion Cassette

PCR is performed using genomic DNA of *S. cerevisiae* CEN.PK2-1D as a template and a primer set of SEQ ID NOS: 81 and 82 as primers to amplify an HHT2 gene promoter. An amplification product of the HHT2 gene promoter (SEQ ID NO: 58) and the prepared ldh gene (SEQ ID NO: 30) (DNA2.0 Inc., USA) are cleaved with SacI/XbaI and BamHI/SalI, respectively and then ligated to the pRS416 vector (ATCC87521™) which has been cleaved with the same enzymes.

The "HPH cassette" and the pRS416 vector containing the HHT2 gene promoter are cleaved with SacI enzyme, respectively and ligated to each other so as to prepare a p416-ldh-HPH vector. Δ pdc6 deletion cassette is prepared by PCR using the p416-ldh-HPH vector as a template and a primer set of SEQ ID NOS: 83 and 84 as primers.

4.2. Preparation of *S. cerevisiae* CEN.PK2-1D(Δ pdc1::ldh, Δ gpd1::ldh, Δ dld1::ldh, Δ pdc6::ldh)

To replace the pdc6 gene with the ldh gene in *S. cerevisiae* CEN.PK2-1D, the "pdc6 deletion cassette" prepared in 4.1 is introduced into *S. cerevisiae* CEN.PK2-1D (Δ pdc1::ldh, Δ gpd1:ldh, Δ dld1::ldh) by heat shock transformation, and cultured in an YPD medium (Yeast extract 1 (w/v) %, peptone 1 (w/v) %, and glucose 2 (w/v) %) containing 200 ug/mL of hygromycin at 30° C. for 3 days for replacement of the chromosomal pdc6 gene with the ldh gene, thereby preparing *S. cerevisiae* CEN.PK2-1D (Δ pdc1::ldh, Δ gpd1: ldh, Δ dld1::ldh, Δ gpd6::ldh) strain. To examine the pdc6 deletion in the resulting strain, PCR is performed using the genome of the cell as a template and a primer set of SEQ ID NOS: 85 and 86 as primers to confirm pdc6 gene deletion.

5. Preparation of *S. cerevisiae* CEN.PK2-1D(Δ pdc1::ldh, Δ gpd1::ldh, Δ dld1::ldh, Δ pdc6::ldh, Δ adh1)

An adh1 gene deletion cassette is amplified by PCR using a deletion vector pUC57-ura3HA as a template and a primer set of SEQ ID NOS: 87 and 88 as primers.

To delete the adh1 gene in *S. cerevisiae* CEN.PK2-1D(Δ pdc1::ldh, Δ gpd1::ldh, Δ dld1::ldh, Δ pdc6::ldh) strain, the prepared "adh1 deletion cassette" is introduced into the strain by heat shock transformation. After heat shock, the strain is cultured in a minimal ura-drop out medium as a selection marker at 30° C. for 3 days to delete adh1 gene on the chromosome. For genotyping of the prepared strain, PCR is performed using a genome of the prepared strain as a template and a primer set of SEQ ID NOS: 89 and 90 to examine deletion of the adh1 gene. As a result, *S. cerevisiae* CEN.PK2-1D (Δ pdc1::ldh, Δ gpd1:ldh, Δ dld1::ldh, Δ pdc6::ldh, Δ adh1) strain is identified.

6. Preparation of *S. cerevisiae* CEN.PK2-1D (Δ pdc1::ldh, Δ gpd1::ldh, Δ dld1::ldh, Δ pdc6::ldh, Δ adh1, Δ ald6:: EcEutE)

6.1. Preparation and Introduction of Vector for ald6 Deletion

An acetaldehyde dehydrogenase 6 (ald6) gene deletion cassette is amplified by PCR using a deletion vector pUC57-ura3HA as a template and a primer set of SEQ ID NOS: 91 and 92 as primers. The sequences of SEQ ID NOS: 91 and 92 include a region which is substituted for the ald6 gene by recombination with a homologous sequence of a chromosome of *S. cerevisiae*.

6.2. Preparation of S. cerevisiae CEN.PK2-1D(Δ pdc1::ldh, Δ cyb2::ldh, Δ gpd1::ldh, Δ adh1, Δ ald6) Strain To delete the ald6 gene in S. cerevisiae CEN.PK2-1D(Δ pdc1::ldh, Δ gpd1:ldh, Δ dld1::ldh, Δ pdc6::ldh, Δ adh1) strain, the "ald6 deletion cassette" prepared in 6.1 is introduced into the strain by heat shock transformation. After heat shock, the strain is cultured in a minimal ura-drop out medium as a selection marker at 30° C. for 3 days to delete ald6 gene on the chromosome. For genotyping of the prepared strain, PCR is performed using a genome of the prepared strain as a template and a primer set of SEQ ID NOS: 93 and 94 to examine deletion of the ald6 gene.

As a result, S. cerevisiae CEN.PK2-1D (Δ pdc1::ldh, Δ gpd1:ldh, Δ dld1::ldh, Δ pdc6::ldh, Δ adh1, Δ ald6) strain is identified.

6.3. Preparation of Yeast Dual Function Overexpression Vector, pCS-Ex1

PCR is performed using a pRS426GPD vector which is widely used as a yeast overexpression vector and a primer set of SEQ ID NO: 95 and SEQ ID NO: 96 to obtain a DNA fragment of 689 bp (GPD promoter). This DNA fragment is cloned into a KpnI-treated pCtB1 vector (Genbank Accession Number KJ922019) using an In-fusion kit (Clonetech, cat. 639650), and introduced into an E. coli cloning strain, TOP10 strain (Invitrogen, cat. C4040-06) by a general method. After introduction, the strain is plated on an LB agar plate (Bacto Tryptone 10 g/L, Yeast Extract 5 g/L, NaCl 10 g/L, and Bacto Agar 15 g/L) containing 50 ug/ml of kanamycin, followed by incubation. From colonies formed, plasmid DNAs are isolated, and plasmids having the same sequence as SEQ ID NO: 97 are examined. As a result, a yeast dual function overexpression vector, pCS-Ex1 is identified. Here, the dual function includes a gene expression after genomic integration of a gene and a gene expression on a vector.

6.4. Preparation of Yeast Dual Function E. coli eutE Gene Overexpression Vector

PCR is performed using genomic DNA of E. coli MG1655 strain and a primer combination of SEQ ID NOS: 98 and 99 so as to obtain a DNA fragment of 1447 bp, that is, EutE gene. This DNA fragment is cloned into a pCS-Ex1 vector which is treated with KpnI and SacI, using an In-fusion kit (Clonetech cat. 639650), and introduced into an E. coli cloning strain, TOP10 strain (Invitrogen, cat. C4040-06) by a general method. After introduction, the strain is plated on an LB agar plate containing 50 ug/ml of kanamycin, followed by incubation. From colonies formed, plasmid DNAs are isolated, and plasmids having the same sequence as SEQ ID NO: 100 are examined. As a result, a yeast dual function E. coli eutE gene overexpression vector, MD1040 is identified.

6.5. Preparation of E. coli eutE Gene-Overexpressing Yeast

From the prepared MD1040 vector, a DNA fragment of 3985 bp is obtained by PCR using a primer combination of SEQ ID NOS: 101 and 102. This fragment is introduced into S. cerevisiae CEN.PK2-1D (Δ pdc1::ldh, Δ gpd1:ldh, Δ dld1::ldh, Δ pdc6::ldh, Δ adh1, Δ ald6) by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, colonies which are confirmed to have a DNA fragment of 4,357 bp by PCR using a primer combination of SEQ ID NOS: 103 and 104 are selected. From genomic DNA of a native strain, a DNA fragment of 2,300 bp is obtained by PCR using a primer combination of SEQ ID NOS: 98 and 99.

The obtained clones are inoculated in an YPD medium (Bacto Peptone 20 g/L, Yeast Extract 10 g/L, and D-glucose 20 g/L), and cultured at 30° C. under shaking at 230 rpm, and then plated on a counter-selection medium containing 5-FOA (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, Uracil 0.1 g/L, D-glucose 20 g/L, 5-fluoroorotic acid (5-FOA) 1 g/L, and Bacto Agar 20 g/L). After 3 days, from colonies formed, colonies which are confirmed to have a DNA fragment of 2,963 bp by PCR using a primer combination of SEQ ID NOS: 105 and 106 are selected.

As a result, S. cerevisiae CEN.PK2-1D (Δ pdc1::ldh, Δ gpd1:ldh, Δ dld1::ldh, Δ pdc6::ldh, Δ adh1, Δ ald6::EcEutE) is identified.

7. Preparation of S. cerevisiae CEN.PK2-1D(Δ pdc1::ldh, Δ gpd1::ldh, Δ dld1::ldh, Δ pdc6::ldh, Δ adh1, Δ ald6::EcEutE, Δ adh5::rck1)

7.1. Preparation of Yeast Dual Function E. coli rck1 Gene Overexpression Vector

PCR is performed using genomic DNA of Saccharomyces cerevisiae and a primer combination of SEQ ID NOS: 107 and 108 so as to obtain a RCK1 gene. This DNA fragment is cloned into a pCS-Ex1 vector which is treated with KpnI and SacI, using an In-fusion kit (Clonetech cat. 639650), and introduced into an E. coli cloning strain, TOP10 strain (Invitrogen, cat. C4040-06) by a general method. After introduction, the strain is plated on an LB agar plate containing 50 ug/ml of kanamycin, followed by incubation. From colonies formed, plasmid DNAs are isolated, and plasmids having the same sequence as RCK1 are examined. As a result, a yeast dual function E. coli RCK1 gene overexpression vector, MD1167 is identified.

7.2. Preparation of RCK1 Gene-Overexpressing Yeast

From the prepared MD1167 vector, a cassette fragment for RCK1 introduction is obtained by PCR using a primer combination of SEQ ID NOS: 109 and 110. This fragment is introduced into S. cerevisiae CEN.PK2-1D Δ pdc1::ldh, Δ gpd1:ldh, Δ dld1::ldh, Δ pdc6::ldh, Δ adh1, Δ ald6) by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having an insertion of a RCK1 gene at ADL6 position is confirmed using a primer combination of SEQ ID NOS: 106 and 107.

The obtained clones are inoculated in an YPD medium (Bacto Peptone 20 g/L, Yeast Extract 10 g/L, and D-glucose 20 g/L), and cultured at 30° C. under shaking at 230 rpm, and then plated on a counter-selection medium containing 5-FOA (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, Uracil 0.1 g/L, D-glucose 20 g/L, 5-fluoroorotic acid (5-FOA) 1 g/L, and Bacto Agar 20 g/L). After 3 days, from colonies formed, a strain having a deletion of URA3 gene is confirmed by PCR using a primer combination of SEQ ID NOS: 111 and 112. As a result, S. cerevisiae CEN.PK2-1D (Δ pdc1::ldh, Δ gpd1:ldh, Δ dld1::ldh, Δ pdc6::ldh, Δ adh1, Δ ald6::RCK1) (hereinafter, referred to as 'SP3027') is identified.

EXAMPLE 2

Preparation of C1 Pathway-Increased Lactate-Producing Strain

1. Preparation of ade3, shm2, or mtd1-Overexpressing Strain (1) Preparation of SP3027 Δ NDT1::P$_{ccw12}$-ADE3 Strain To prepare a vector containing a 'ADE3 cassette', a sequence containing a coding region of ADE3 (SEQ ID NO: 2) is amplified from genomic DNA of *Saccharomyces cerevisiae* CEN.PK2-1D strain by PCR using a primer set of SEQ ID NOS: 113 and 114 as primers. The resulting product is cloned into a pCS-Ex1.1 vector treated with XhoI and XbaI using an In-fusion kit (Clonetech, cat. 639650), so as to obtain a pCCW12-ADE3 vector which is a vector overexpressing the yeast ADE3 gene. The ADE3 gene in this vector is transcribed under a CCW12 promoter. FIG. 2 illustrates the pCS-Ex1.1 vector.

A cassette fragment for ADE3 introduction is amplified from the prepared pCCW12-ADE3 vector by PCR using a primer combination of SEQ ID NOS: 115 and 116 having a homologous sequence with the NDT1 gene. This ADE3 cassette fragment is introduced into *Saccharomyces cerevisiae* SP3027 strain. Introduction of the ADE3 cassette is performed by general heat shock transformation. After transformation, cells are cultured in a uracil dropout medium to replace NDT1 ORF on the chromosome with the cassette.

To examine the ADE3 introduction in the resulting cells, PCR is performed using the genome of the cell as a template and a primer set of SEQ ID NOS: 117 and 118 to confirm ndt1 gene deletion and ade3 gene introduction. As a result, SP3027(Δ ndt1::ade3) is identified.

Further, a cassette for ndt1 gene deletion is amplified by PCR using a deletion vector pUC57-ura3HA as a template and a primer set of SEQ ID NOS: 119 and 120 as primers.

To delete the ndt1 gene from *S. cerevisiae* CEN.PK2-1D SP3027 strain, the prepared "ndt1 deletion cassette" is introduced into the strain by heat shock transformation. After transformation, cells are cultured in a minimal uradrop out medium as a selection marker at 30° C. for 3 days to delete ndt1 gene on the chromosome. For genotyping of the prepared strain, PCR is performed using a genome of the prepared strain as a template and a primer set of SEQ ID NOS: 117 and 118 to examine deletion of the ndt1 gene. As a result, *S. cerevisiae* CEN.PK2-1D SP3027(Δ ndt1) strain is identified.

(2) Preparation of SP3027 Δ NDT1::P$_{gpd}$-SHM2 Strain

To prepare a vector containing a 'SHM2 cassette', a sequence containing a coding region of SHM2 (SEQ ID NO: 4) is amplified from genomic DNA of *Saccharomyces cerevisiae* CEN.PK2-1D strain by PCR using a primer set of SEQ ID NOS: 121 and 122 as primers. The resulting product is cloned into a pCS-Ex1 vector treated with XhoI and XbaI using an In-fusion kit (Clonetech, cat. 639650), so as to obtain a pGPD-SHM2 vector which is a vector overexpressing the yeast SHM2 gene. The SHM2 gene in this vector is transcribed under a GPD promoter.

A cassette fragment for SHM2 introduction is amplified from the prepared pGPD-SHM2 vector by PCR using a primer combination of SEQ ID NOS: 115 and 116 having a homologous sequence with the NDT1 gene. This SHM2 cassette fragment is introduced into *Saccharomyces cerevisiae* SP3027 strain. Introduction of the SHM2 cassette is performed by general heat shock transformation. After transformation, cells are cultured in a uracil dropout medium to replace NDT1 ORF on the chromosome with the cassette.

To examine the SHM2 introduction in the resulting cells, PCR is performed using the genome of the cell as a template and a primer set of SEQ ID NOS: 117 and 118 to confirm ndt1 gene deletion and SHM2 gene introduction. As a result, SP3027(Δ ndt1::shm2) is identified.

(3) Preparation of SP3027 Δ NDT1::P$_{gpd}$-MTD1 Strain

To prepare a vector containing a 'MTD1 cassette', a sequence containing a coding region of MTD1 (SEQ ID NO: 6) is amplified from genomic DNA of *Saccharomyces cerevisiae* CEN.PK2-1D strain by PCR using a primer set of SEQ ID NOS: 123 and 124 as primers. The resulting product is cloned into a pCS-Ex1 vector treated with XhoI and XbaI using an In-fusion kit (Clonetech, cat. 639650), so as to obtain a pGPD-MTD1 vector which is a vector overexpressing the yeast MTD1 gene. The MTD1 gene in this vector is transcribed under a GPD promoter.

A cassette fragment for MTD1 introduction is amplified from the prepared pGPD-MTD1 vector by PCR using a primer combination of SEQ ID NOS: 115 and 116 having a homologous sequence with the NDT1 gene. This MTD1 cassette fragment is introduced into *Saccharomyces cerevisiae* SP3027 strain. Introduction of the MTD1 cassette is performed by general heat shock transformation. After transformation, cells are cultured in a uracil dropout medium to replace NDT1 ORF on the chromosome with the cassette.

To examine the MTD1 introduction in the resulting cells, PCR is performed using the genome of the cell as a template and a primer set of SEQ ID NOS: 117 and 118 to confirm ndt1 gene deletion and mtd1 gene introduction. As a result, SP3027(Δ ndt1::mtd1) is identified.

2. Lactate Production and Cell Growth of ade3, shm2, or mtd1-Overexpressing Strain The transformed yeast cells thus prepared are inoculated in 20 ml of YPD media containing 60 g/L of glucose at an OD600 value of 1, and cultured under microaerobic conditions at 36° C. under shaking at 90 rpm for about 48 hours. During culture, cell growth is determined by measuring the OD600 value using a spectrophotometer. Concentrations of the produced lactate, residual ethanol, and residual glucose are analyzed by HPLC (High performance liquid chromatography).

As a result, cell growth, that is, OD600 value of the culture, and glucose consumption, concentrations of the produced lactate and ethanol are given in Table 1 below.

TABLE 1

| Strain | Glucose consumption (g/L) | OD$_{600}$ | Lactate (g/L) | Lactate yield (%) | Ethanol (g/L) | Ethanol yield (%) |
|---|---|---|---|---|---|---|
| SP3027 | 26.88 | 2.70 | 19.59 | 72.90 | 1.06 | 3.94 |
| SP3027 (Δ ndt1) | 27.07 | 2.89 | 19.47 | 71.95 | 1.19 | 4.38 |
| SP3027(Δ ndt1::ade3) | 28.94 | 3.34 | 22.55 | 77.92 | 1.441.44 | 4.98 |
| SP3027(Δ ndt1::shm2) | 29.39 | 3.21 | 22.64 | 77.01 | 1.411.41 | 4.79 |
| SP3027(Δ ndt1::mtd1) | 29.10 | 2.90 | 23.06 | 79.24 | 1.481.48 | 5.09 |

As shown in Table 1, the ade3-overexpressing strain shows increased glucose consumption, cell growth, and lactate and ethanol productions, compared to a control group. The shm2-overexpressing strain also shows increased glucose consumption, cell growth, and lactate and ethanol productions, compared to the control group. The mtd1-overexpressing strain also shows increased glucose consumption, cell growth, and lactate and ethanol productions, compared to the control group.

EXAMPLE 3

Preparation of NADH Kinase-Increased Lactate-Producing Strain

1. Preparation of UTR1, YEF1, sPOS5, or POS5-Overexpressing Strain (1) Preparation of SP3027 Δ NDT1::$P_{HHT2}$-UTR1 Strain To prepare a vector containing a 'UTR1 cassette', a sequence containing a coding region of UTR1 (SEQ ID NO: 8) is amplified from genomic DNA of Saccharomyces cerevisiae CEN.PK2-1D strain by PCR using a primer set of SEQ ID NOS: 125 and 126 as primers. The resulting product is cloned into a pCS-Ex1.9 vector treated with XhoI and XbaI using an In-fusion kit (Clonetech, cat. 639650), so as to obtain a pHHT2-UTR1 vector which is a vector overexpressing the yeast UTR1 gene. The UTR1 gene in this vector is transcribed under an HHT2 promoter.

A cassette fragment for UTR1 introduction is amplified from the prepared pHHT2-UTR1 vector by PCR using a primer combination of SEQ ID NOS: 115 and 116 having a homologous sequence with the NDT1 gene. This UTR1 cassette fragment is introduced into Saccharomyces cerevisiae SP3027 strain. Introduction of the UTR1 cassette is performed by general heat shock transformation. After transformation, cells are cultured in a uracil dropout medium to replace NDT1 ORF on the chromosome with the cassette.

To examine the UTR1 introduction in the resulting cells, PCR is performed using the genome of the cell as a template and a primer set of SEQ ID NOS: 117 and 118 to confirm ndt1 gene deletion and UTR1 gene introduction. As a result, SP3027(Δ ndt1::utr1) is identified.

(2) Preparation of SP3027 Δ NDT1::$P_{HHT2}$-YEF1 Strain

To prepare a vector containing a 'YEF1 cassette', a sequence containing a coding region of YEF1 (SEQ ID NO: 10) is amplified from genomic DNA of Saccharomyces cerevisiae CEN.PK2-1D strain by PCR using a primer set of SEQ ID NOS: 126 and 127 as primers. The resulting product is cloned into a pCS-Ex1.9 vector treated with XhoI and XbaI using an In-fusion kit (Clonetech, cat. 639650), so as to obtain a pHHT2-YEF1 vector which is a vector overexpressing the yeast YEF1 gene. The YEF1 gene in this vector is transcribed under an HHT2 promoter.

A cassette fragment for YEF1 introduction is amplified from the prepared pHHT2-YEF1 vector by PCR using a primer combination of SEQ ID NOS: 115 and 116 having a homologous sequence with the NDT1 gene. This YEF1 cassette fragment is introduced into Saccharomyces cerevisiae SP3027 strain. Introduction of the YEF1 cassette is performed by general heat shock transformation. After transformation, cells are cultured in a uracil dropout medium to replace NDT1 ORF on the chromosome with the cassette.

To examine the YEF1 introduction in the resulting cells, PCR is performed using the genome of the cell as a template and a primer set of SEQ ID NOS: 117 and 118 to confirm ndt1 gene deletion and YEF1 gene introduction. As a result, SP3027(Δ ndt1::yef1) is identified.

(3) Preparation of SP3027 Δ NDT1::$P_{HHT2}$-sPOS5 Strain

To prepare a vector containing a 'sPOS5 cassette', a sequence containing a coding region of sPOS5 (SEQ ID NO: 14) is amplified from genomic DNA of Saccharomyces cerevisiae CEN.PK2-1D strain by PCR using a primer set of SEQ ID NOS: 128 and 129 as primers. The resulting product is cloned into a pCS-Ex1.9 vector treated with XhoI and XbaI using an In-fusion kit (Clonetech, cat. 639650), so as to obtain a pHHT2-sPOS5 vector which is a vector overexpressing the yeast sPOS5 gene. The sequence containing a coding region of sPOS5 is prepared by removing 132 bp of 5'-mitochondrial targeting sequence and adding atg in the POS5 gene sequence of SEQ ID NO: 12. The mitochondrial targeting sequence is predicted using MITOPROT (M. G. Claros et al., Eur. J. Biochem. 241, 779-786 (1996)). MITOPROT is available in http://ihg.gsf.de/ihg/mitoprot.html. The sPOS5 gene in this vector is transcribed under an HHT2 promoter.

A cassette fragment for sPOS5 introduction is amplified from the prepared pHHT2-sPOS5 vector by PCR using a primer combination of SEQ ID NOS: 115 and 116 having a homologous sequence with the NDT1 gene. This sPOS5 cassette fragment is introduced into Saccharomyces cerevisiae SP3027 strain. Introduction of the sPOS5 cassette is performed by general heat shock transformation. After transformation, cells are cultured in a uracil dropout medium to replace NDT1 ORF on the chromosome with the cassette.

To examine the sPOS5 introduction in the resulting cells, PCR is performed using the genome of the cell as a template and a primer set of SEQ ID NOS: 117 and 118 to confirm ndt1 gene deletion and sPOS5 gene introduction. As a result, SP3027(Δ ndt1::sPOS5) is identified.

(4) Preparation of SP3027 Δ NDT1::$P_{HHT2}$-POS5 Strain

To prepare a vector containing a 'POS5 cassette', a sequence containing a coding region of POS5 (SEQ ID NO: 12) is amplified from genomic DNA of Saccharomyces cerevisiae CEN.PK2-1D strain by PCR using a primer set of SEQ ID NOS: 128 and 129 as primers. The resulting product is cloned into a pCS-Ex1.9 vector treated with XhoI and XbaI using an In-fusion kit (Clonetech, cat. 639650), so as to obtain a pHHT2-POS5 vector which is a vector overexpressing the yeast POS5 gene. The POS5 gene in this vector is transcribed under an HHT2 promoter.

A cassette fragment for POS5 introduction is amplified from the prepared pHHT2-POS5 vector by PCR using a primer combination of SEQ ID NOS: 115 and 116 having a homologous sequence with the NDT1 gene. This POS5 cassette fragment is introduced into Saccharomyces cerevisiae SP3027 strain. Introduction of the POS5 cassette is performed by general heat shock transformation. After transformation, cells are cultured in a uracil dropout medium to replace NDT1 ORF on the chromosome with the cassette.

To examine the POS5 introduction in the resulting cells, PCR is performed using the genome of the cell as a template and a primer set of SEQ ID NOS: 117 and 118 to confirm ndt1 gene deletion and POS5 gene introduction. As a result, SP3027(Δ ndt1::POS5) is identified.

2. LA Production and Cell Growth of UTR1, YEF1, sPOS5, or POS5-Overexpressing Strain The transformed yeast cells thus prepared are inoculated in 20 ml of YPD media containing 60 g/L of glucose at an OD600 value of 1, and cultured under microaerobic conditions at 36° C. under shaking at 90 rpm for about 48 hours. During culture, cell growth is determined by measuring the OD600 value using a spectrophotometer. Concentrations of the produced lactate, residual ethanol, and residual glucose are analyzed by HPLC (High performance liquid chromatography).

As a result, cell growth, that is, OD600 value of the culture, and glucose consumption, concentrations of the produced lactate and ethanol are given in Table 2 below.

TABLE 2

| Strain | Glucose consumption (g/L) | OD$_{600}$ | Lactate (g/L) | Lactate yield (%) | Ethanol (g/L) | Ethanol yield (%) |
|---|---|---|---|---|---|---|
| SP3027 | 27.30 | 2.86 | 22.28 | 81.59 | 1.49 | 5.47 |
| SP3027 (Δ ndt1) | 27.61 | 2.88 | 22.23 | 80.51 | 1.53 | 5.53 |
| SP3027(Δ ndt1::utr1) | 32.08 | 3.52 | 26.29 | 81.95 | 1.96 | 6.10 |
| SP3027(Δ ndt1::yef1) | 31.57 | 3.19 | 26.20 | 82.99 | 1.75 | 5.56 |
| SP3027(Δ ndt1::sPOS5) | 31.73 | 3.20 | 26.38 | 83.13 | 1.75 | 5.50 |
| SP3027(Δ ndt1::POS5) | 30.43 | 3.35 | 24.61 | 80.86 | 1.81 | 5.95 |

As shown in Table 2, the urt1-overexpressing strain shows increased glucose consumption, cell growth, and lactate and ethanol productions, compared to a control group. The yef1-overexpressing strain also shows increased glucose consumption, cell growth, and lactate and ethanol productions, compared to the control group. The sPOS5-overexpressing strain also shows increased glucose consumption, cell growth, and lactate and ethanol productions, compared to the control group. The POS5-overexpressing strain also shows increased glucose consumption, cell growth, and lactate and ethanol productions, compared to the control group.

EXAMPLE 4

Preparation of NADP-Dependent GAPDH-Introduced Lactate-Producing Strain

1. Preparation of Introduced Strain

A gene encoding GDP1 of SEQ ID NO: 16 is amplified by PCR using gDNA of *Kluyveromyces marxianus* as a template and a primer set of SEQ ID NOS: 130 and 131 as primers.

To prepare a vector containing a 'gdp1 cassette', a PGK promoter sequence (SEQ ID NO: 134) obtained by PCR using genomic DNA of *Saccharomyces cerevisiae* as a template and a primer set of SEQ ID NOS: 132 and 133 as primers and 'gdp1 gene (SEQ ID NO: 2)' are digested with SacI/XbaI and BamHI/SalI, respectively and then ligated to a pRS416 vector (ATCC87521) digested with the same enzymes so as to prepare a pRS416-pPGK-GDP1 vector. The gdp1 gene in this vector is transcribed under a PGK promoter.

A gdp1 gene fragment obtained by PCR using pRS416-pPGK-GDP1 as a template and a primer set of SEQ ID NOS: 132 and 135 as primers, and a pUC57-Ura3HA vector (DNA2.0 Inc.; SEQ ID NO: 68) are digested with SacI, respectively and then ligated to each other so as to prepare pUC-uraHA-gdp1. From this vector, a gdp1 cassette is amplified by PCR using primers of SEQ ID NOS: 119 and 120 having a homologous sequence with the ndt1 gene.

The gdp1 cassette thus prepared is introduced into *Saccharomyces cerevisiae* SP3027 strain. Introduction of the gdp1 cassette is performed by general heat shock transformation. After transformation, cells are cultured in a uracil dropout medium to replace ndt1 ORF on the chromosome with the cassette. To examine the gdp1 introduction in the resulting cells, PCR is performed using the genome of the cell as a template and a primer set of SEQ ID NOS: 117 and 118 to confirm gdp1 gene deletion and ade3 gene introduction. As a result, SP3027(Δ ndt1:: gdp1) is identified.

2. LA Production and Cell Growth of NADP-Dependent GAPDH-Introduced Strain

The transformed yeast cells thus prepared are inoculated in 20 ml of YPD media containing 60 g/L of glucose at an OD600 value of 1, and cultured under microaerobic conditions at 36° C. under shaking at 90 rpm for about 48 hours. During culture, cell growth is determined by measuring the OD600 value using a spectrophotometer. Concentrations of the produced lactate, residual ethanol, and residual glucose are analyzed by HPLC (High performance liquid chromatography).

As a result, cell growth, that is, OD600 value of the culture, and glucose consumption, concentrations of the produced lactate and ethanol are given in Table 3 below.

TABLE 3

| Strain | Glucose consumption (g/L) | OD$_{600}$ | Lactate (g/L) | Lactate yield (%) | Ethanol (g/L) | Ethanol yield (%) |
|---|---|---|---|---|---|---|
| SP3027 | 24.90 ± 0.67 | 2.46 ± 0.12 | 21.02 ± 0.38 | 84.43 ± 0.76 | 1.57 ± 0.07 | 6.30 ± 0.14 |
| SP3027 (Δ ndt1) | 25.15 ± 0.51 | 2.74 ± 0.25 | 21.27 ± 1.24 | 84.56 ± 3.24 | 1.54 ± 0.02 | 6.14 ± 0.19 |
| SP3027 (Δ ndt1::gdp1) | 27.41 ± 0.31 | 3.26 ± 0.16 | 23.43 ± 0.16 | 85.49 ± 0.53 | 1.26 ± 0.06 | 4.59 ± 0.18 |

As shown in Table 3, the strain introduced with gdp1 derived from *K. maxianus* shows increased glucose consumption, cell growth, and lactate and ethanol productions, compared to a control group.

EXAMPLE 5

Preparation of Pentose Phosphate Pathway-Increased Lactate-Producing Strain

1. Preparation of zwf1-Overexpressing Strain

A gene encoding a TPI promoter (PTPI) of SEQ ID NO: 59 is amplified by PCR using genomic DNA of *Saccharomyces cerevisiae* CEN.PK2-1D strain as a template and a primer set of SEQ ID NOS: 136 and 137 as primers. Further, a URA cassette of SEQ ID NO: 140 is amplified by PCR using a pUC57-Ura3HA vector (DNA2.0 Inc.; SEQ ID NO: 68) as a template and a primer set of SEQ ID NOS: 138 and 139 as primers. The 'URA cassette' refers to a region that directs URA3 gene expression because it includes URA3 gene and its regulatory sequence.

To prepare a DNA fragment of SEQ ID NO: 141 containing the URA cassette and TPI promoter, the obtained URA cassette and TPI promoter are mixed and ligated using an In-fusion kit (Clonetech, cat. 639650). Next, a ZWF1 promoter substitution cassette is amplified by PCR using this DNA fragment (SEQ ID NO: 141) as a template and primers of SEQ ID NOS: 142 and 143 having a homologous sequence with a promoter region of ZWF1 gene.

The ZWF1 promoter substitution cassette thus prepared is introduced into *Saccharomyces cerevisiae* SP3027 strain. Introduction of the ZWF1 promoter substitution cassette is performed by general heat shock transformation. After transformation, cells are cultured in a uracil dropout medium.

To examine the ZWF1 promoter substitution in the resulting cells, PCR is performed using the genome of the cell as a template and a primer set of SEQ ID NOS: 144 and 145 to confirm ZWF1 promoter substitution. As a result, SP3027 (zwf1+) is identified. The zwf1 gene in the strain is transcribed under a TPI1 promoter.

2. LA Production and Cell Growth of zwf1-Overexpressing Strain

The transformed yeast cells thus prepared are inoculated in 20 ml of YPD media containing 60 g/L of glucose at an OD600 value of 1, and cultured under microaerobic conditions at 36° C. under shaking at 90 rpm for about 48 hours. During culture, cell growth is determined by measuring the OD600 value using a spectrophotometer. Concentrations of the produced lactate, residual ethanol, and residual glucose are analyzed by HPLC (High performance liquid chromatography).

As a result, cell growth, that is, OD600 value of the culture, and glucose consumption, concentrations of the produced lactate and ethanol are given in Table 4 below.

TABLE 4

| Strain | Glucose consumption (g/L) | $OD_{600}$ | Lactate (g/L) | Lactate yield (%) | Ethanol (g/L) | Ethanol yield (%) |
|---|---|---|---|---|---|---|
| SP3027 | 30.46 ± 1.25 | 03.74 ± 0.17 | 24.27 ± 1.00 | 79.69 ± 0.01 | 2.25 ± 0.09 | 7.40 ± 0.01 |
| SP3027 (zwf1+) | 36.92 ± 0.11 | 4.47 ± 0.07 | 29.77 ± 0.04 | 80.63 ± 0.12 | 3.07 ± 0.05 | 8.32 ± 0.15 |

As shown in Table 4, the zwf1-overexpressing strain shows increased glucose consumption, cell growth, and lactate and ethanol productions, compared to a control group.

EXAMPLE 6

Preparation of Transhydrogenase-Introduced Lactate-Producing Strain

1. Preparation of *E. coli*-Derived SthA Gene-Introduced Strain

*E. coli*-derived sthA gene (SEQ ID NO: 20) is synthesized (DNA 2.0 Inc., USA), and subjected to PCR using primers of SEQ ID NOS: 146 and 147 so as to amplify the sthA-encoding gene.

To prepare a vector containing a 'sthA cassette', the amplified sthA gene is cloned into a pCS-Ex1.1 vector treated with XhoI and XbaI using an In-fusion kit (Clonetech, cat. 639650), so as to obtain a pCCW12-sthA vector which is a vector overexpressing the *E. coli* sthA gene. The sthA gene in this vector is transcribed under a CCW12 promoter.

A cassette fragment for sthA introduction is amplified from the prepared pCCW12-sthA vector by PCR using a primer combination of SEQ ID NOS: 115 and 116 having a homologous sequence with the NDT1 gene. This sthA cassette fragment is introduced into *Saccharomyces cerevisiae* SP3027 strain. Introduction of the sthA cassette is performed by general heat shock transformation. After transformation, cells are cultured in a uracil dropout medium to replace NDT1 ORF on the chromosome with the cassette.

To examine the sthA introduction in the resulting cells, PCR is performed using the genome of the cell as a template and a primer set of SEQ ID NOS: 117 and 118 to confirm ndt1 gene deletion and sthA gene introduction. As a result, SP3027(Δ ndt1::sthA) is identified.

2. LA Production and Cell Growth of *E. coli*-Derived SthA Gene-Introduced Strain The transformed yeast cells thus prepared are inoculated in 20 ml of YPD media containing 60 g/L of glucose at an OD600 value of 1, and cultured under microaerobic conditions at 36° C. under shaking at 90 rpm for about 48 hours. During culture, cell growth is determined by measuring the OD600 value using a spectrophotometer. Concentrations of the produced lactate, residual ethanol, and residual glucose are analyzed by HPLC (High performance liquid chromatography).

As a result, cell growth, that is, OD600 value of the culture, and glucose consumption, concentrations of the produced lactate and ethanol are given in Table 5 below.

TABLE 5

| Strain | Glucose consumption (g/L) | $OD_{600}$ | Lactate (g/L) | Lactate yield (%) | Ethanol (g/L) | Ethanol yield (%) |
|---|---|---|---|---|---|---|
| SP3027 | 27.30 | 2.86 | 22.28 | 81.59 | 1.49 | 5.47 |
| SP3027 (Δ ndt1) | 27.61 | 2.88 | 22.23 | 80.51 | 1.53 | 5.53 |
| SP3027 (Δ ndt1::SthA) | 30.58 | 3.24 | 24.79 | 81.09 | 1.53 | 5.00 |

As shown in Table 5, the sthA-overexpressing strain shows increased glucose consumption, cell growth, and lactate production, compared to a control group.

EXAMPLE 7

Preparation of Lactate-Producing Strain Introduced with LDH Enzyme Using Both NADH and NADPH 1. Preparation of Strain Introduced with *L. delbrueckii* subsp. *Bulgaricus*-Derived LDH Mutant A gene encoding ldh is amplified by PCR using gDNA of *L. delbrueckii* subsp. *Bulgaricus* as a template and a primer set of SEQ ID NOS: 148 and 149 as primers. A gene encoding a lactate dehydrogenase mutant (hereinafter, referred to as 'LbLDH(D176A)') is obtained by site direct mutagenesis using the obtained wild-type lactate dehydrogenase gene (SEQ ID NO: 24) as a template. The gene encoding the mutant is D176A having a polynucleotide sequence of SEQ ID NO: 22.

To prepare a vector containing a 'LbLDH(D176A) cassette', an LbLDH(D176A) gene amplified using primers of SEQ ID NOS: 188 and 189 is cloned into a pCS-Ex1.1 vector treated with XhoI and XbaI using an In-fusion kit (Clonetech, cat. 639650), so as to obtain a pCCW12-LbLDH (D176A) vector which is a vector overexpressing the E. coli sthA gene. The LbLDH(D176A) gene in this vector is transcribed under a CCW12 promoter.

A cassette fragment for LbLDH(D176A) introduction is amplified from the prepared pCCW12-sthA vector by PCR using a primer combination of SEQ ID NOS: 115 and 116 having a homologous sequence with the NDT1 gene. This LbLDH(D176A) cassette fragment is introduced into *Saccharomyces cerevisiae* SP3027(zwf1+) strain. Introduction of the LbLDH(D176A) cassette is performed by general heat shock transformation. After transformation, cells are cultured in a uracil dropout medium to replace NDT1 ORF on the chromosome with the cassette.

To examine the LbLDH(D176A) introduction in the resulting cells, PCR is performed using the genome of the cell as a template and a primer set of SEQ ID NOS: 117 and 118 to confirm ndt1 gene deletion and LbLDH(D176A) gene introduction. As a result, SP3027(zwf1+, Δ ndt1::LbLDH (D176A)) is identified. A wild-type LbLDH-introduced SP3027(zwf1+, Δ ndt1::LbLDHwt) is also prepared in the same manner.

2. LA Production and Cell Growth of Strain Introduced with *L. delbrueckii* subsp. *Bulgaricus*-Derived LDH Mutant The transformed yeast cells thus prepared are inoculated in 20 ml of YPD media containing 60 g/L of glucose at an OD600 value of 1, and cultured under microaerobic conditions at 36° C. under shaking at 90 rpm for about 48 hours. During culture, cell growth is determined by measuring the OD600 value using a spectrophotometer. Concentrations of the produced lactate, residual ethanol, and residual glucose are analyzed by HPLC (High performance liquid chromatography).

As a result, cell growth, that is, OD600 value of the culture, and glucose consumption, concentrations of the produced lactate and ethanol are given in Table 6 below.

TABLE 6

| Strain | Glucose consumption (g/L) | $OD_{600}$ | Lactate (g/L) | Lactate yield (%) | Ethanol (g/L) | Ethanol yield (%) |
|---|---|---|---|---|---|---|
| SP3027 (zwf1+) | 45.89 | 3.17 | 37.90 | 82.60 | 2.13 | 4.63 |
| SP3027 (zwf1+, Δ ndt1::LbLDHwt) | 46.17 | 3.17 | 39.61 | 85.80 | 2.06 | 4.47 |
| SP3027 (zwf1+, Δ ndt1::LbLDH (D176A)) | 42.93 | 2.82 | 40.25 | 93.74 | 1.74 | 4.06 |

As shown in Table 6, the strain introduced with the LbLDH(D176A)-encoding gene shows increased glucose consumption, cell growth, and lactate and ethanol productions, compared to a control group.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered yeast cell, wherein the genetically engineered yeast cell comprises:
   a genetic modification that increases the activity of ZWF1 as compared to a parent yeast cell without the genetic modification;
   and an exogenous polynucleotide encoding a polypeptide that converts pyruvate to lactate;
   wherein the yeast cell has increased lactate production compared to a parent cell.

2. The genetically engineered yeast cell of claim 1, wherein the genetic modification that increases the activity of ZWF1 comprises:
   an increase in the copy number of a zwf1 gene, as compared to a parent yeast cell; and/or
   a modification of an expression regulatory sequence of a zwf1 gene.

3. The genetically engineered yeast cell of claim 1, wherein the ZWF1 and the polypeptide that converts pyruvate to lactate comprise the amino acid sequences of SEQ ID NO: 17, and 21, respectively.

4. The genetically engineered yeast cell of claim 1, wherein the yeast cell belongs to the genus *Saccharomyces, Kluyveromyces, Candida, Pichia, Issatchenkia, Debaryomyces, Zygosaccharomyces, Shizosaccharomyces*, or *Saccharomycopsis*.

5. A method of increasing the level of lactate in a yeast cell, the method comprising
   overexpressing zwf,
   and introducing into the yeast cell an exogenous polynucleotide encoding a gene encoding a polypeptide that converts pyruvate to lactate.

6. The method of claim 5, wherein the yeast cell is *Saccharomyces cerevisiae*.

7. A method of producing lactate, the method comprising culturing the genetically engineered yeast cell of claim 4 so as to produce lactate.

8. The method of claim 7, further comprising recovering lactate from the culture.

* * * * *